US012605122B2

(12) United States Patent
Freeman et al.

(10) Patent No.: US 12,605,122 B2
(45) Date of Patent: Apr. 21, 2026

(54) DEVICE AND METHOD FOR CLINICAL EVALUATION

(71) Applicant: Respiratory Motion, Inc., Watertown, MA (US)

(72) Inventors: Jenny E. Freeman, Weston, MA (US); Ziad Elghazzawi, Newton, MA (US); Jasmin Imsirovic, Cambridge, MA (US)

(73) Assignee: Respiratory Motion, Inc., St. Louis, MO (US)

( * ) Notice: Subject to any disclaimer, the term of this patent is extended or adjusted under 35 U.S.C. 154(b) by 968 days.

(21) Appl. No.: 16/895,969

(22) Filed: Jun. 8, 2020

(65) Prior Publication Data

US 2020/0383647 A1     Dec. 10, 2020

Related U.S. Application Data

(60) Provisional application No. 62/858,898, filed on Jun. 7, 2019.

(51) Int. Cl.
*A61B 5/00*         (2006.01)
*A61B 5/0205*       (2006.01)
(Continued)

(52) U.S. Cl.
CPC .......... *A61B 5/746* (2013.01); *A61B 5/02055* (2013.01); *A61B 5/1455* (2013.01);
(Continued)

(58) Field of Classification Search
CPC ... A61B 5/746; A61B 5/02055; A61B 5/1455; A61B 5/208; A61B 5/4824; A61B 5/4833; A61B 5/4842; A61B 5/4848; A61B 5/7264; A61B 5/021; A61B 5/0245; A61B 5/0809; A61B 5/0816; A61B 5/091; A61B 2560/0228; A61B 5/0205; A61B 5/6823
See application file for complete search history.

(56)                References Cited

U.S. PATENT DOCUMENTS 3,433,217  A     3/1969   Rieke et al.
3,690,143  A     9/1972   Day et al.
(Continued)

FOREIGN PATENT DOCUMENTS

CN          1034665        8/1989
CN          101496767      2/2009
(Continued)

OTHER PUBLICATIONS

"Multi-Parameter Alert supports hospital sepsis protocol." Product News Network : NA. Thomas Industrial Netw ork, Inc. (Apr. 4, 2016) (Year: 2016).*
(Continued)

*Primary Examiner* — Linh Giang Le
(74) *Attorney, Agent, or Firm* — Remenick PLLC

(57)                ABSTRACT

Systems and methods of evaluating a patient comprise the steps of obtaining temporal data of the patient after an event, monitoring a plurality of patient parameters, compiling patient data based on the temporal data and patient parameters, determining a state or change in state of the patient based on the compiled patient data, and alerting medical staff of the state or change in state.

34 Claims, 31 Drawing Sheets

(51) Int. Cl.

| | |
|---|---|
| *A61B 5/1455* | (2006.01) |
| *A61B 5/20* | (2006.01) |
| *A61B 5/021* | (2006.01) |
| *A61B 5/0245* | (2006.01) |
| *A61B 5/08* | (2006.01) |
| *A61B 5/085* | (2006.01) |
| *A61B 5/091* | (2006.01) |

(52) U.S. Cl.

CPC ............ *A61B 5/208* (2013.01); *A61B 5/4824* (2013.01); *A61B 5/4833* (2013.01); *A61B 5/4842* (2013.01); *A61B 5/4848* (2013.01); *A61B 5/7264* (2013.01); *A61B 5/021* (2013.01); *A61B 5/0245* (2013.01); *A61B 5/0816* (2013.01); *A61B 5/086* (2025.01); *A61B 5/091* (2013.01); *A61B 2560/0228* (2013.01)

(56) References Cited

U.S. PATENT DOCUMENTS

| | | | |
|---|---|---|---|
| 3,742,936 | A | 7/1973 | Blanie et al. |
| 4,036,217 | A | 7/1977 | Ito et al. |
| 5,058,583 | A | 10/1991 | Geddes et al. |
| 5,469,859 | A | 11/1995 | Tsoglin et al. |
| 5,735,284 | A | 4/1998 | Tsoglin et al. |
| 6,168,568 | B1 | 1/2001 | Gavriely |
| 6,173,198 | B1 | 1/2001 | Schulze et al. |
| 6,286,806 | B1 | 9/2001 | Corcoran |
| 6,366,803 | B1 | 4/2002 | Fee |
| 6,402,969 | B1 | 6/2002 | Rodgers et al. |
| 6,809,462 | B2 | 10/2004 | Pelrine et al. |
| 6,976,963 | B2 | 12/2005 | Clift |
| 7,196,317 | B1 | 3/2007 | Meissner, II et al. |
| 7,361,146 | B1 | 4/2008 | Bharmi et al. |
| 7,530,956 | B2 | 5/2009 | Lewicke et al. |
| 8,096,962 | B2 | 1/2012 | Palazzolo et al. |
| 8,306,611 | B2 | 11/2012 | Granov et al. |
| 10,702,166 | B1 * | 7/2020 | Freeman .............. A61B 5/0803 |
| 2002/0032383 | A1 | 3/2002 | Weil et al. |
| 2004/0071337 | A1 | 4/2004 | Jeung et al. |
| 2004/0123667 | A1 | 7/2004 | McGrath |
| 2005/0033198 | A1 | 2/2005 | Kehyayan et al. |
| 2005/0090753 | A1 | 4/2005 | Goor et al. |
| 2005/0107719 | A1 | 5/2005 | Arad (Abbound) |
| 2005/0113702 | A1 | 5/2005 | Salla et al. |
| 2006/0058600 | A1 | 3/2006 | Eichler |
| 2006/0241506 | A1 | 10/2006 | Melker et al. |
| 2006/0241513 | A1 | 10/2006 | Hatlestad et al. |
| 2007/0010764 | A1 | 1/2007 | Palazzolo et al. |
| 2007/0276300 | A1 | 11/2007 | Olson et al. |
| 2008/0312565 | A1 | 12/2008 | Celik-Butler et al. |
| 2009/0062672 | A1 | 3/2009 | Sly et al. |
| 2009/0149748 | A1 | 6/2009 | Lenhardt et al. |
| 2009/0227849 | A1 | 9/2009 | Goor et al. |
| 2009/0264789 | A1 | 10/2009 | Molnar et al. |
| 2009/0326253 | A1 | 12/2009 | Iding et al. |
| 2009/0326353 | A1 | 12/2009 | Watson et al. |
| 2010/0049071 | A1 | 2/2010 | Goor et al. |
| 2010/0152600 | A1 | 6/2010 | Droitcour et al. |
| 2010/0228166 | A1 | 9/2010 | Centen |
| 2010/0241181 | A1 | 9/2010 | Savage et al. |
| 2011/0077497 | A1 | 3/2011 | Oster et al. |
| 2011/0245712 | A1 | 10/2011 | Patterson et al. |
| 2011/0288609 | A1 * | 11/2011 | Tehrani .............. A61N 1/3601 607/42 |
| 2011/0306850 | A1 | 12/2011 | Hatlestad et al. |
| 2012/0041279 | A1 | 2/2012 | Freeman et al. |
| 2012/0136221 | A1 | 5/2012 | Kilien et al. |
| 2012/0165883 | A1 | 6/2012 | Kalgren et al. |
| 2013/0187941 | A1 | 7/2013 | Noon |
| 2013/0296823 | A1 | 11/2013 | Melker et al. |
| 2014/0073895 | A1 | 3/2014 | Freeman et al. |
| 2015/0106020 | A1 | 4/2015 | Chung et al. |
| 2018/0098739 | A1 | 4/2018 | Freeman et al. |
| 2019/0008467 | A1 * | 1/2019 | Averina .............. G16H 70/60 |
| 2019/0125214 | A1 * | 5/2019 | Addison .............. A61B 5/363 |

FOREIGN PATENT DOCUMENTS

| | | | |
|---|---|---|---|
| CN | 106571094 A * | 4/2017 | |
| EP | 1302217 | 4/2003 | |
| EP | 2008581 | 12/2008 | |
| EP | 2018825 | 1/2009 | |
| JP | 200070370 | 3/2000 | |
| JP | 2007203041 | 8/2007 | |
| JP | 2009240752 | 10/2009 | |
| WO | WO0033733 | 6/2000 | |
| WO | WO2006006871 | 7/2004 | |
| WO | WO2007064682 | 6/2007 | |
| WO | WO2007147505 | 12/2007 | |
| WO | WO2008130549 | 10/2008 | |
| WO | WO2009035965 | 3/2009 | |
| WO | WO2009036312 | 3/2009 | |
| WO | WO2010059049 | 5/2010 | |

OTHER PUBLICATIONS

U.S. Appl. No. 12/677,216, Freeman et al.
U.S. Appl. No. 13/210,360, Freeman et al.
U.S. Appl. No. 13/554,346, Freeman et al.
U.S. Appl. No. 14/021,939, Freeman et al.
Zulkarneev R Kh. Et al., A Hardware-Software System for Volumetric Calibration of Impedance Pneumograms, Biomedical Engineering, vol. 35, No. 1, 2001, pp. 48-51.
Pajic, et al, Model-driven safety analysis of closed-loop medical systems, IEEE Trans Industr Inform. vol. 10, pp. 1-35, p. 4, para. 1-2, Oct. 28, 2013.
PCT Search Report and Written Description for PCT/US2020/036677 dated Oct. 16, 2020.

\* cited by examiner

RVM
MEASUREMENT

VOLUME (L)

INTEGRATED
RVM
ELECTRODE

FACE
MASK

RVM
ELECTRODE

RVM
ELECTRODE

RVM
ELECTRODE

FACE
MASK

RVM
ELECTRODE

DEVICE AND METHOD FOR CLINICAL EVALUATION

REFERENCE TO RELATED APPLICATIONS

This application claims priority to U.S. Provisional Application No. 62/858,898, filed Jun. 7, 2019, entitled "DEVICE AND METHOD FOR CLINICAL EVALUATION," and hereby specifically and entirely incorporated by reference.

BACKGROUND OF THE INVENTION

1. Field of the Invention

The invention is a system and a method that diagnoses and/or stratifies patients by taking in data from various physiological parameters, demographics, clinical events, treatments, lab test results using supervised and unsupervised learning techniques including but not limited to machine learning, Bayesian inference networks, expert systems, principal component analysis, fractal analysis, statistical techniques, heuristic analysis, deep temporal continuous and discontinuous clustering that integrates dimensionality reduction and temporal clustering into a single end-to-end learning framework, maximum margin temporal clustering, fuzzy logic, and neural networks.

2. Description of the Background

Physiological monitors provide information that can be used by doctors to directly diagnose patients or as part of an integrated approach to generate physiological scores that indicate patient deterioration. Physiological scores, such as the Mortality Probability Model (MPM), the Acute Physiology and Chronic Health Education (APACHE), the Simplified Acute Physiological Score (SAPS) and the Therapeutic Intervention Scoring System (TISS) have shown significant improvements in patient outcomes. Monitoring sick patients by using physiological scores and vital signs in their early stages of illness, even prior to organ failure or shock, improves outcomes. Close monitoring of patients allows for recognition of patient degeneration and the administration of the appropriate therapy.

Early Warning Systems

An array of early warning scores (EWS) are used by doctors to warn of impending patient deterioration including the modified early warning score (MEWS), pediatric early warning score (PEWS), modified early obstetric warning score (MEOWS), and national early warning score (NEWS). Implementing EWS as part of a protocol for patient care has improved overall outcomes, however, these methods do not accurately predict patient outcomes in approximately 15% of ICU patients. Furthermore, the sensitivity and specificity of such scores may be worse for patients in a respiratory intensive care unit, which provide care in hospitals with large number of patients with acute respiratory failure. This may be in part due to the limited predictive power of respiratory rate in early diagnosis of respiratory complications. It has been shown that the rate of breathing has poor sensitivity and specificity of predicting low minute ventilation, which is the product of tidal volume and respiratory rate and is the fundamental measure of ventilation. Until recently minute ventilation has been difficult to measure, particularly in non-intubated patients.

While EWS present a general warning of patient deterioration, other scores are used to aid or confirm a more specific diagnosis, such as sepsis. Several scores have been used as part of sepsis protocols including the Systemic Inflammatory Response Syndrome (SIRS), Sequential Organ Failure Assessment (SOFA), and its more feasible counterpart called quick SOFA (qSOFA). These scores take into account various physiological parameters available from monitoring devices or clinical observation (temperature, heart rate, respiratory rate, blood pressure, mental status, suspicion of infection), and lab tests (white blood cell count, platelet count, bilirubin, creatinine). Notably, these scores only consider respiratory rate, while ignoring tidal volume, despite the correlation between ventilation and increased metabolic demand experienced in sepsis.

Tradeoffs between accuracy, timeliness, and feasibility have been made in selecting parameters to calculate such scores. While lab tests can provide information to increase accuracy of scores, they are not always timely or feasible. More importantly the reporting frequency of physiological parameters influence the timeliness with which scores can be calculated. For example, vital signs may only be taken every 4 hours on patients on the hospital floor, thus the physiological score can only be updated at the same frequency. Even in the ICU, only some patient undergo continuous monitoring that lends itself to more frequent score calculation. Furthermore, continuous monitoring has been shown to have issues with false alarms and both patient and staff compliance.

Monitoring Ventilation

Previously, direct monitoring of ventilation was limited to intubated patients confined to the ICU or OR. Non-invasive continuous monitoring of minute ventilation has recently been made feasible by advances in a bio-impedance based Respiratory Volume Monitor (RVM). By providing continuous, real-time measurements of not only rate of breathing, but also depth of breathing, ventilation measurements may be incorporated into new physiological scores and warning systems for predicting adverse outcomes such as respiratory depression, respiratory failure, sepsis, congestive heart failure, COPD exacerbations, asthma attacks, etc. The low false alarm rate associated with the RVM allows for continuous monitoring and more frequent calculation of physiological scores utilizing respiratory metrics, particularly tidal volume and minute ventilation. Earlier methods of monitoring ventilation, including pulse oximetry, capnography, and respiratory rate counting, have been shown to be delayed indicators of respiratory compromise, and furthermore have been prone to false alarms.

Shortcomings of Current Monitoring Methods—False Alarms

Current monitoring methods can alert medical staff of patient deterioration, but are also prone to false alarms, which limit the efficacy of monitoring equipment. In fact, the vast majority of alarms (87%) reported by monitors in the ICU are false positive alarms. Excessive alarms result in alarm fatigue for medical staff, which can lead to behavior that decreases patient safety. For example, medical professionals may ignore alarms in an attempt to decrease alarm fatigue. It has been reported that less than 1% of alarms lead to changes in patient care. Likewise, 78% of clinicians disable alarms entirely, which places patients at greater risk of a missed event.

The problem of alarm fatigue has been recognized by the Joint Commission, which made improved alarm management a goal in its safety initiative. Despite the new emphasis on alarms, programs to improve alarm safety have had little success and alarm fatigue persists.

Part of the problem of excessive alarms are the thresholds used to signal an alarm event. Studies have shown that decreasing alarm thresholds can result in a decrease of false alarms. For example, pulse oximetry can alarm for hypoxia at a threshold of 90%, but significantly lower false alarm rates were measured using 85% or 80% as thresholds. While a lower threshold may result in fewer false positive alarms, it increases the chance of false negatives. Given that hypoxia is already a late indicator of changes in ventilation, further delays in alarms caused by lower thresholds can put patients at greater risk of undetected respiratory compromise.

The majority of physiologic monitors are designed to alarm based on alarm thresholds, and may have no indication of the quality of the signal used to trigger the alarm or the context of the alarm. Despite most alarms being false positives, monitors have no ability to qualify alarms after they have occurred and sounded. Therefore, it may be useful to have a system to identify alarms from physiologic monitors and label them as "true" or "false" positives, or conversely, as "false" negatives in the absence of alarms that occurred during a missed event. Such a system could decrease alarm fatigue by either cancelling alarms or limiting the frequency with which medical staff are required to respond to alarms deemed to be false positives, either in real time or retrospectively. Furthermore, the system could improve early warning systems and diagnosis algorithms by qualifying alarms with the appropriate contextual data including: physiologic data from other monitors, temporal information regarding events and spatial information about the patient.

Yet another concern with physiologic monitoring and early warning systems has been the lack of temporal context to the measurements used. For example, the accuracy of the physiologic measurements is known to change with time, but this is generally not considered in the thresholds used to detect alarms.

Physiological Monitoring—History and Evolution

Patient monitoring is essential because it provides warning to patient deterioration and allows for the opportunity of early intervention, greatly improving patient outcomes. For example, modern monitoring devices can detect abnormal heart rhythms, blood oxygen saturation, and body temperature, which can alert clinicians of a deterioration that would otherwise go unnoticed.

The earliest records of patient monitoring reveal that ancient Egyptians were aware of the correlation between peripheral pulse and the heart beat as early as 1550 BC. Three millennia passed before the next significant advancement in monitoring was made, with Galileo using a pendulum to measure pulse rate. In 1887, Waller determined that he could passively record electrical activity across the chest by using electrodes and correlated the signal to activity from the heart. Waller's discovery paved the way for the use of electrical signals as a method to measure physiological signals. However, it would still take time before scientists recognized the advantages of monitoring a physiological signal in a clinical environment.

In 1925, MacKenzie emphasized the importance of continuous recording and monitoring of physiological signals such as the pulse rate and blood pressure. He specifically stressed that the graphical representation of these signals is important in the assessment of a patient's condition. In the 1960s, with the advent of computers, patient monitors improved with the addition of a real-time graphical display of multiple vital signs being recorded simultaneously. Alarms were also incorporated into monitors and were triggered when signals, such as a pulse rate or blood pressure, reached a certain threshold.

The first patient monitors were used on patients during surgery. As patient outcomes were shown to improve, monitoring of vital signs spread to other areas of the hospital such as the intensive care unit and the emergency department. For instance, pulse oximetry was first widely used in operating rooms as a method to continuously measure a patient's oxygenation non-invasively. Pulse oximetry quickly became the standard of care for the administration of general anesthetic and subsequently spread to other parts of the hospital, including the recovery room and intensive care units.

The Growing Need for Improved Patient Monitoring

The number of critically ill patients presenting to the emergency department is increasing at a great rate, and these patients require close monitoring. It has been estimated that between 1-8% of patients in the emergency department require a critical care procedure to be performed, such as a cardiovascular procedure or a thoracic and respiratory procedure (mechanical ventilation, catheter insertion, arterial cannulation).

Physiological scores, such as the Mortality Probability Model (MPM), the Acute Physiology and Chronic Health Education (APACHE), the Simplified Acute Physiological Score (SAPS) and the Therapeutic Intervention Scoring System (TISS) have shown significant improvements in patient outcomes. Monitoring sick patients by using physiological scores and vital signs in their early stages of illness, even prior to organ failure or shock, improves outcomes. Close monitoring of patients allows for recognition of patient degeneration and the administration of the appropriate therapy.

However, current scoring methods do not accurately predict patient outcomes in approximately 15% of ICU patients, and it may be worse for patients in a respiratory intensive care unit, which provide care in hospitals with large number of patients with acute respiratory failure. Furthermore, differences in currently monitored vital signs such as blood oxygenation occur late in the progression of respiratory or circulatory compromise. Often the earliest sign of patient degradation is a change in a patient's breathing effort or respiratory pattern.

Respiratory rate is recognized as a vital indicator of patient health and is used to assess patient status. However, respiratory rate alone fails to indicate important physiological changes, such as changes in respiratory volumes. Metrics derived from continuous volume measurements have been shown to have great potential for determining patient status in a wide range of clinical applications. However, there are currently no adequate systems that can accurately and conveniently determine respiratory volumes, which motivates the need for a non-invasive respiratory monitor that can trace changes in breath volume.

Shortcomings of Current Methods

Currently, a patient's respiratory status is monitored with methods such as spirometry and end tidal $CO_2$ measurements. These methods are often inconvenient to use and inaccurate. While end tidal $CO_2$ monitoring is useful during anesthesia and in the evaluation of intubated patients in a variety of environments, it is inaccurate for non-ventilated patients. The spirometer and pneumotachometer are limited in their measurements are highly dependent on patient effort and proper coaching by the clinician. Effective training and quality assurance are a necessity for successful spirometry. However, these two prerequisites are not necessarily enforced in clinical practice like they are in research studies and pulmonary function labs. Therefore quality assurance is essential to prevent misleading results.

Spirometry is the most commonly performed pulmonary function test. The spirometer and pneumotachometer can give a direct measurement of respiratory volume. It involves assessing a patient's breathing patterns by measuring the volume or the flow of air as it enters and leaves the patient's body. Spirometry procedures and maneuvers are standardized by the American Thoracic Society (ATS) and the European Respiratory Society (ERS). Spirometry can provide important metrics for evaluating respiratory health and diagnosing respiratory pathologies. The major drawback of mainstream spirometers is that they require the patient to breathe through a tube so that the volume and/or flow rate of his breath can be measured. Breathing through the apparatus introduces resistance to the flow of breath and changes the patient's breathing pattern. Thus it is impossible to use these devices to accurately measure a patient's normal breathing. Breathing through the apparatus requires a conscious, compliant patient. Also, in order to record the metrics suggested by the ATS and ERS, patients must undergo taxing breathing maneuvers, which excludes most elderly, neonatal, and COPD patients from being able to undergo such an examination. The outcomes of the procedures are also highly variable dependent on patient effort and coaching, and operator skill and experience. The ATS also recommends extensive training for healthcare professionals who practice spirometry. Also, many physicians do not have the skills needed to accurately interpret the data gained from pulmonary function tests. According to the American Thoracic Society, the largest source of intrasubject variability is improper performance of test. Therefore much of the intrapatient and interpatient variability in pulmonary function testing is produced by human error. Impedance-based respiratory monitoring fills an important void because current spirometry measurements are unable to provide continuous measurements because of the requirement for patient cooperation and breathing through a tube. Therefore there is a need for a device that provides near-real-time information over extended periods of time (vs. spirometry tests which last a minute or less) in non-intubated patients that can show changes in respiration related to a provocative test or therapeutic intervention.

In order to acquire acceptable spirometry measurements, as dictated by ATS standards, healthcare professionals must have extensive training and take refresher courses. A group showed that the amount of acceptable spirometry measurements was significantly greater for those who did a training workshop (41% vs. 17%). Even with acceptable spirometry measurements, the interpretations of the data by primary physicians were deemed as incorrect 50% of the time by pulmonologists. However, it was noted that aid from computer algorithms showed improvement in interpreting spirograms when adequate spirometry measurements were collected.

Rigorous training is needed for primary care clinics to acquire acceptable spirometry measurements and make accurate interpretations. However, resources to train a large number of people and enforce satisfactory quality assurance are unreasonable and inefficient. Even in a dedicated research setting, technician performance falls over time.

In addition to human error due to the patient and healthcare provider, spirometry contains systematic errors that ruin breathing variability measurements. Useful measurements of breath by breath patterns and variability have been shown to be compounded by airway attachments such as a facemask or mouthpiece. Also, the discomfort and inconvenience involved during measurement with these devices prevents them from being used for routine measurements or as long-term monitors. Other less intrusive techniques such as thermistors or strain gauges have been used to predict changes in volume, but these methods provide poor information on respiratory volume. Respiratory belts have also shown promise in measuring respiration volume, but groups have shown that they are less accurate and have a greater variability than measurements from impedance pneumography. Therefore, a system that can measure volume for long periods of time with minimal patient and clinician interaction is needed.

Pulmonary Function Testing and Preoperative, Postoperative Care

Preoperative care is centered on identifying what patient characteristics may put the patient at risk during an operation and minimizing those risks. Medical history, smoking history, age, and other parameters dictate the steps taken in preoperative care. Specifically, elderly patients and patients with pulmonary diseases may be at risk for respiratory complications when placed under a ventilator for surgery. In order to clear these patients for surgery, pulmonary function tests such as spirometry are performed which give the more information to determine whether the patient can utilize the ventilator. Chest x-rays may also be taken. However, these tests cannot be replicated mid-surgery, or in narcotized patients or those who cannot or will not cooperate. Testing may be uncomfortable in a postoperative setting and disruptive to patient recovery.

End Tidal $CO_2$ and Patient Monitoring

End tidal $CO_2$ is another useful metric for determining pulmonary state of a patient. The value is presented as a percentage or partial pressure and is measured continuously using a capnograph monitor, which may be coupled with other patient monitoring devices. These instruments produce a capnogram, which represents a waveform of $CO_2$ concentration. Capnography compares carbon dioxide concentrations within expired air and arterial blood. The capnogram is then analyzed to diagnose problems with respiration such as hyperventilation and hypoventilation. Trends in end tidal $CO_2$ are particularly useful for evaluating ventilator performance and identifying drug activity, technical problems with intubation, and airway obstruction. The American Society of Anesthesiologists (ASA) mandates that end-tidal $CO_2$ be monitored any time an endotracheal tube or laryngeal mask is used, and is also highly encouraged for any treatment that involves general anesthesia. Capnography has also been proven to be more useful than pulse oximetry for monitoring of patient ventilation. Unfortunately, it is generally inaccurate and difficult to implement in the non-ventilated patient, and other complementary respiratory monitoring methods would have great utility.

Echocardiograms

Fenichel et al. determined that respiratory motion can cause interference with echocardiograms if it is not controlled for. Respiratory motion can block anterior echoes through pulmonary expansion and it chances the angle of incidence of the transducer ray relative to the heart. These effects on the echocardiography signal can decrease the accuracy of measurements recorded or inferred from echocardiograms. Combining echocardiography with accurate measurement of the respiratory cycle can allow an imaging device to compensate for respiratory motion.

Impedance Pneumography

Impedance pneumography is a simple method that can yield respiratory volume tracings without impeding airflow, does not require contact with the airstream, and does not restrict body movements. Furthermore, it may be able to make measurements that reflect functional residual capacity of the lungs.

While attempting to measure cardiac activity, Atzler and Lehmann noted transthoracic electrical impedance changed with respiration. They regarded the respiratory impedance changes as artifacts and asked the patients to stop breathing while measurements were made. In 1940, while also studying cardiac impedance, Nyboer noticed the same respiratory impedance artifact in his measurement. He confirmed the origin of the artifact by being the first person to relate changes in transthoracic impedance to changes in volume using a spirometer by simultaneously recording both. Goldensohn and Zablow took impedance pneumography a step further by being the first investigators to quantitatively relate respired volume and transthoracic impedance. They reported difficulty in separating the cardiac signal artifacts and also noted artifacts during body movements. However, after comparing the impedance changes and respired volume changes by a least squares regression, they importantly determined that the two are linearly related. Other groups have confirmed the linear relationship between transthoracic impedance changes and respiratory breaths and have found that approximately 90% of the spirometric signal can be explained by the thoracic impedance signal. While the relationship has been shown to be linear, many groups found the calibration constants for intrapatient and interpatient to be highly variable between trials. These differences in calibration constants can be attributed to a variety of physiological and electrode characteristics, which must be taken into account.

Transthoracic Impedance Theory

Electrical impedance is a complex quantity defined as the sum of the resistance (R), the real component, and the reactance (X), the imaginary component ($Z=R+jX=-Z-^{j\Theta}$). It is used as the measurement of opposition to an alternating current. Mathematically, impedance is measured by the following equation, which is analogous to Ohm's law:

$$Z=V/I \quad (1)$$

Where voltage=V, current=I, and impedance=Z. An object that conducts electricity with unknown impedance can be determined from a simple circuit. Applying a known alternating current across the object while simultaneously measuring the voltage across it and using equation (1) yields the impedance. The thorax represents a volume conductor, and because of that, the laws governing ionic conductors can be applied. In addition, the movement of organs and the enlargement of the thoracic cage during breathing create a change in conductivity, which can be measured. Impedance across the thorax can be measured by introducing a known current and measuring the change in voltage across the thorax with electrodes.

Origins of the Transthoracic Impedance Signal

The tissue layers that makeup the thorax and the abdomen, all influence the measurement of transthoracic impedance. Each tissue has a different conductivity that influences the direction of current flow between electrodes. Beginning with the outermost layer, the surface of the body is covered by skin, which presents a high resistivity but is only about 1 mm thick. Under the skin is a layer of fat, which also has a high resistivity. However, the thickness of this layer is highly variable and depends on body location and the body type of the subject. Moving posterior to anterior, below the layer of skin and fat are the postural muscles, which are anisotropic. They have a low resistivity in the longitudinal direction but a high resistivity in all other directions, which leads to a tendency to conduct current in a direction that is parallel to the skin. Below the muscle are the ribs, which, as bone, are highly insulating. Therefore, current through the thorax can only flow between bones. Once current reaches the lungs, it is hypothesized that current travels through the blood, which has one of the lowest resistances of any body tissue. Aeration of the lungs changes the size of the lung and the pathway of current flow, and manifests itself as a change in resistance or impedance that can be measured.

Due to the anisotropic properties of the tissues, radial current flow through the chest is much less than would be expected. Much of the current goes around the chest rather than through it. As a result, impedance changes come from changes in thoracic circumference, changes in lung size, and movement of the diaphragm-liver mass. Measurements at lower thoracic levels are attributed to movement of the diaphragm and liver, and at higher thoracic levels they are attributed to aeration and expansion of the lungs. Therefore, the impedance signal is the sum of the change from the expansion and aeration of the lungs and the movement of the diaphragm-liver mass. Both the abdominal and thoracic components are needed in order to observe a normal respiratory signal. In addition, the different origins of impedance changes in the upper and lower thorax could explain why greater linearity is observed at higher thoracic levels.

Influences of Electrode Placement

Transthoracic impedance is measured with electrodes attached to the patient's skin. Geddes et al. determined that the electrode stimulation frequency should not be below 20 kHz because of physiological tissue considerations. It is a matter of safety and eliminating interference from bioelectric events. In addition, impedance measurements of a subject were found to differ depending on subject position, including sitting, supine, and standing. It was shown that for a given change in volume, laying supine yielded the greatest signal amplitude and lowest signal to noise during respiration.

Another potential signal artifact comes from subject movements, which may move electrodes and disturb calibrations. Furthermore, electrode movements may be more prevalent in obese and elderly patients, which may require repetitive lead recalibration during periods of long-term monitoring. Because of the calibration variability between trials, some have suggested that calibration should be performed for each individual for a given subject posture and electrode placement. However, a group was able to show that careful intrapatient electrode placement can reduce impedance differences between measurements to around 1%.

Despite having the same electrode placements, calibration constants and signal amplitudes for individuals of different sizes showed variability. It was determined that the change in impedance for a given change in volume is the largest for thin-chested people and smaller for people who are more amply sized. These observed differences may be due to the greater amount of resistive tissue, such as adipose tissue and muscle, between the electrodes and lungs in larger subjects, yielding an overall smaller percent change in impedance for a given change in volume for larger subjects. On the other hand, it is noticeable that in children the cardiac component of the impedance trace is greater than in adults. This may be due to greater fat deposition around the heart in adults than in children, which serves to shield the heart from being incorporated into the impedance measurement.

Electrodes attached to the mid-axillary line at the level of the sixth rib yielded the maximum impedance change during respiration. However, the greatest linearity between the two variables was attained by placing the electrodes higher on the thorax. Despite the high degree of linearity reported, large standard deviations of impedance changes during respiration have been reported. However, the variability observed in impedance measurements is comparable to those seen in measurements of other vital signs, such as blood pressure. Groups have shown that impedance pneumography methods are sufficiently accurate for clinical purposes. Furthermore, in the 40 years since these studies, electrode materials and signal processing of the impedance measurements have greatly improved, yielding even more reliable measurements. Digital signal processing allows for the near instantaneous filtering and smoothing of real-time impedance measurements, which allows for the minimization of artifacts and noise. More recently, respiratory impedance has been used successfully in long-term patient monitoring. As long as the electrodes remain relatively unmoved, the relationship of change in impedance to change in volume is stable for long periods of time.

Active Acoustic System

The most common use of acoustics in relationship to the lungs is to evaluate sounds that originate in the lungs acquired by the use of a stethoscope. One frequently overlooked property of lung tissue is its ability to act as an acoustic filter. It attenuates various frequencies of sound that pass through them to different extents. There is a relationship between the level of attenuation and the amount of air in the lungs. Motion of the chest wall also results in frequency shift of acoustic signals passing through the thorax.

Potential for Detecting Abnormalities

Many useful indicators, such as the forced vital capacity (FVC) and forced expiratory volume in one second ($FEV_1$), can be extracted from monitoring the volume trace of a patient's respiration with impedance pneumography. The FVC and FEV1 are two benchmark indicators typically measured by a spirometer and are used to diagnose and monitor diseases such as COPD, asthma, and emphysema. In addition to monitoring the respiration, impedance pneumography can also simultaneously record the electrocardiogram from the same electrodes.

Breath-to-Breath Variability

Calculations such as breath to breath variability, coefficient of variance, standard deviation, and symmetry of a tidal volume histogram have been shown to be dependent on age and respiratory health. Compared to normal subjects it has been shown that some of these parameters, particularly coefficient of variance, are significantly different in patients with tuberculosis, pneumonitis, emphysema, and asthma. Furthermore, it has been noted in the literature that impedance measurements were satisfactory as long as the electrodes did not move on the patient. In general, it has been determined by many groups that healthy subjects show greater variability in breathing patterns than subjects in a pulmonary disease state.

The nonlinear analysis of respiratory waveforms has been used in a wide array of applications. In examining the regularity of nonlinear, physiologic data, studies have shown that within pulmonary disease states, patients exhibit a decrease in breath-to-breath complexity. This decrease in complexity has been demonstrated within chronic obstructive pulmonary disease, restrictive lung disease, and within patients that fail extubation from mechanical ventilation. Reduced variability has also been determined to be a result of sedation and analgesia. In broad terms, normal patients have greater breath to breath variability than those afflicted by some form of pulmonary disease or compromise.

The respiratory pattern is nonlinear, like any physiologic data, as it is influenced by a multitude of regulatory agents within the body. Within the analysis of breath-to-breath variability, various entropy metrics are used to measure the amount of irregularity and reproducibility within the signal. These metrics can be used within the analysis of RVM tidal volume tracings in assessing not only breath-to-breath changes, but intrabreath variability, as well as magnitude, periodicity, and spatial location of the curve.

Universal calibration of the system based off standardized patient characteristic data (Crapo) allows for the creation of a complexity index, and comparison of a single patient to what is defined as a normal level of complexity. This index would be used to aid clinicians in determining the appropriate time to extubate, determining the severity of cardiopulmonary disease, and also within the assessment of therapeutics. This index would be independent of the method in which data is collected, whether through an impedance based device, accelerometers, a ventilator, or an imaging device. The system could also be calibrated to a specific patient and focus on intra-subject variability while detecting rapid changes within any of the respiratory parameters.

Nonlinear Analysis of Interbreath Intervals

In addition to variability metrics, some groups have found that nonlinear analysis of instantaneous interbreath intervals are highly correlated to the success of weaning from a mechanical ventilator. These metrics are useful indicators of pulmonary health and can assist in clinical decisions. The inability for a patient to separate from a mechanical ventilator occurs in approximately 20% of patients and current methods to predict successful separation are poor and add little to a physician's decision. In a study with 33 subjects under mechanical ventilation for greater than 24 hours, it was found that 24 subjects were successfully weaned from ventilation while 8 subjects failed (data from one subject was removed). The reasons of failure were cited as hypoxia in five subjects, and tachypnea, hypercapnia, and upper airway edema for the remaining three, all of which are diseases that can be potentially identified by an impedance pneumography system. The primary finding in this study was that the nonlinear analysis of instantaneous breath intervals for those who failed to separate from the mechanical ventilator was significantly more regular than those who separated successfully. Furthermore, it was shown that the respiratory rate did not differ between the two groups. The metrics derived from nonlinear analysis of impedance pneumography measurements can successfully predict patient outcomes. In addition, these metrics have been shown to be robust and did not significantly change when artifacts such as coughing were introduced.

Detection of Decreased Ventilation States

The respiratory trace produced by impedance pneumography as well as the average impedance of a subject can indicate states of decreased ventilation or changes in fluid volume in the thorax. This type of monitoring would be useful for the care of anesthetized patients. Respiratory monitoring with impedance pneumography in anaesthetized or immobile patients is shown to be accurate and reliable for long periods, especially during the critical period in the recovery room after surgery. Investigators have determined that fluid in the thorax or lungs can lead to measurable changes in impedance, which can be used to determine common problems for patients in the recovery room such as pulmonary edema or pneumonia.

In addition to measuring changes in fluid volume in the thorax, changes in tidal volume and upper airway resistance are immediately apparent in impedance measurements.

Investigators found that endotracheal clamping of anaesthetized patients still produced a diminished impedance signal despite the patient's effort to breathe, thereby giving a correct indication of ventilation. It has also been shown that impedance measurements provide quantitative assessment of the ventilation of each lung. Differences in impedance measurements were observed in patients with unilateral pulmonary lesions, with a pair of electrodes on the injured side of the thorax producing a less pronounced signal than the normal side.

Respiratory Monitors

While certain contact probes record respiratory rate, to date, no device or method has been specifically devised to record or to analyze respiratory patterns or variability, to correlate respiratory patterns or variability with physiologic condition or viability, or to use respiratory patterns or variability to predict impending collapse. Heart rate variability algorithms only report on variations in heart rate, beat-to-beat. It is desirable to use respiratory rate variability algorithms to incorporate variability in respiratory intensity, rate, and location of respiratory motion. Marked abnormalities in respiration as noted by changes in intensity, in rate, in localization of respiratory effort, or in variability of any of these parameters provide an early warning of respiratory or cardiovascular failure and may present an opportunity for early intervention. Development of a device to record these changes and creation of algorithms that correlate these respiratory changes with severity of illness or injury would provide not only a useful battlefield tool, but also one of importance in the hospital critical care setting to help evaluate and treat critically ill patients. Use in the clinic or home setting could be of use to less critically ill patients that nonetheless would benefit from such monitoring. For example, respiratory rate drops and respirations become "shallow" if a patient is overly narcotized. Respiratory rate and respiratory effort rise with stiff lungs and poor air exchange due to pulmonary edema or other reasons for loss of pulmonary compliance. However, the implications of the rate, which is the only parameter objectively monitored is frequently not identified soon enough to best treat the patient. A system that could provide a real time, quantitative assessment of work of breathing and analyze the trend of respiratory rate, intensity, localization, or variability in any or all of these parameters is needed for early diagnosis and intervention as well as therapeutic monitoring. Such a system is needed to judge the depth of anesthesia, or the adequacy or overdose of narcotic or other pain relieving medications.

PCA and Feedback Controls

Patient Controlled Analgesia (PCA) is a method of post-operative pain control that includes patient feedback. The administration of opiates can suppress respiration, heart rate, and blood pressure, hence the need for careful and close monitoring. The system comprises a computerized pump that contains pain medication that can be pumped into the patient's IV line. Generally, in addition to a constant dose of pain medication, the patient may press a button to receive care in the form of additional medication. However, patients are discouraged from pressing the button if they are getting too drowsy as this may prevent therapy for quicker recovery. There are also safeguards in place that limit the amount of medication given to a patient in a given amount of time to prevent overdose. Pulse oximeters, respiratory rate and capnograph monitors may be used to warn of respiratory depression caused by pain medication and cut off the PCA dose, but each has serious limitations regarding at least accuracy, validity, and implementation.

Breathing Assistance Devices

Chronic obstructive pulmonary disease ("COPD"), emphysema, and other ailments have an effect of lowering the ability for the patient to provide efficient exchange of air and provide adequate respiration. COPD is a lung disease that makes it hard to breathe. It is caused by damage to the lungs over many years, usually from smoking. COPD is often a mix of two diseases: chronic bronchitis and emphysema. In chronic bronchitis, the airways that carry air to the lungs get inflamed and make a lot of mucus. This can narrow or block the airways, making it hard for you to breathe. In a healthy person, the tiny air sacs in the lungs are like balloons. As a person breathes in and out, the air sacs get bigger and smaller to move air through the lungs. However, with emphysema, these air sacs are damaged and lose their stretch. Less air gets in and out of the lungs, which causes shortness of breath. COPD patients often have difficulty getting enough oxygenation and/or CO2 removal and their breathing can be difficult and labored.

Cystic fibrosis ("CF"), also known as mucoviscidosis, is a genetic disorder that affects mostly the lungs but also the pancreas, liver, kidneys and intestine. Long-term issues include difficulty breathing and coughing up sputum as a result of frequent lung infections. Other symptoms include sinus infections, poor growth, fatty stool, clubbing of the finger and toes, and infertility in males among others.

There are numerous therapies used to help alleviate the symptoms of COPD, CF, emphysema, and other breathing problems. For example, the patient may wear a High-Frequency Chest Wall Oscillation ("HFCWO") vest or oscillator. The HFCWO vest is an inflatable vest attached to a machine that vibrates it at high frequency. The vest vibrates the chest to loosen and thin mucus. Alternatively, a patient may us a continuous positive airway pressure ("CPAP") or bilevel positive airway pressure ("BiPAP") device to provide mild air pressure on a continuous basis to keep the airways continuously open in a patient who is able to breathe spontaneously on his or her own. Other mechanical ventilation therapies include, but are not limited to cough assist systems, oxygen therapy, suction therapy, CHFO ("Continuous High Frequency Oscillation"), ventilators, medicated aerosol delivery systems, and other non-invasive ventilation methods.

Each of these therapeutic methods has a common drawback, there is no way of knowing how much air is actually getting into the lungs. Some therapies use air pressure feedback to time effective oxygen therapy. This can be inaccurate and is not a direct measurement of oxygen ventilation. Furthermore, therapies using masks can be inaccurate due to leakage and problems associated with mask placement. Additionally, kinking and malfunctions in the pneumatic airway circuits can provide and inaccurate measure of the amount of air which is getting into the lungs.

SUMMARY OF THE INVENTION

The present invention overcomes the problems and disadvantages associated with current automated physiological scoring systems by incorporating non-invasive respiratory measurements to improve diagnosis and patient stratification.

A preferred embodiment of the invention is directed to a method of evaluating a patient. The method comprises the steps of obtaining temporal data of the patient after an event, monitoring a plurality of patient parameters, compiling patient data based on the temporal data and patient parameters, determining a state or change in state of the patient based on the compiled patient data, and alerting medical staff of the state or change in state.

In a preferred embodiment, the temporal data is used for diagnosing and/or stratifying the patient based on the state of the patient and alerting medical staff of a diagnosis and/or stratification. Preferably, the temporal data is used to qualify or weigh the data used in making the determination of patient state or in making a determination of a diagnosis and/or a stratification determination based on at least one of the amount of time after the event or the length of time elapsed monitoring the patient. An event is preferably at least one of a surgery, medication administration, intubation, extubation, lab tests, and a medical procedures, and patient care action. Preferably, the parameters are at least one of physiological parameters, demographics, location, clinical events, treatments, physical state, and lab test results. In a preferred embodiment, the patient parameters are obtained from sensors or inputs that measure Minute ventilation (MV) and/or % of predicted MV, Tidal volume (TV), Respiratory rate (RR), Ventilation flow-volume relationship, Peripheral blood oxygen saturation (SpO2), Mixed venous oxygen saturation (SvO2), End-tidal carbon dioxide (EtCO2), Sublingual and/or transcutaneous CO2, temperature, Cardiac Output (CO), Cardiac index, Perfusion, Blood pressure (BP), Heart Rate (HR), Electrocardiogram (ECG), Renal fluid volumes and rates, Pain level scores and locations, Medication information, Patient location, Present and prior patient diagnoses and stratification of risk based on different clinical evaluation techniques, Temporal and ratiometric relationships of parameter measurements with respect to patient locations, Variation and rate of variation thereof, or Temporal and ratiometric relationships thereof.

Preferably, the diagnosing and/or stratifying of the patient is based on at least one of supervised and unsupervised learning techniques, machine learning, Bayesian inference networks, expert systems, principal component analysis, support vector machines, time series forecasting and analysis, fractal analysis, statistical techniques, heuristic algorithms, deep temporal continuous and discontinuous clustering that integrates dimensionality reduction and temporal clustering into a single end-to-end learning framework, maximum margin temporal clustering, fuzzy logic, and neural networks. In a preferred embodiment, the diagnosis and/or stratifications are compared to a database of historic diagnosis and/or stratifications. Preferably, feedback from caregivers is updated in the database for future diagnosis and/or stratifications. Preferably the patient parameters include independent measurements of tidal volume (TV) and respiratory rate (RR) of the patient. The TV and RR are preferably indicative of a patient's status.

Another embodiment of the invention is directed to a system of evaluating a patient, comprising a processor adapted to obtain temporal data of the patient after an event, a plurality of input devices in communication with the processor adapted to monitor a plurality of patient parameters. Wherein the processor compiles patient data including the temporal data and patient parameters, determines a state or change in state of the patient based on the compiled patient data, and alerts medical staff of the state or change in state.

In a preferred embodiment, the temporal data is used for diagnosing and/or stratifying the patient based on the state of the patient and alerting medical staff of a diagnosis and/or stratification. Preferably, the temporal data is used to qualify or weigh the data used in making the determination of patient state or in making a determination of a diagnosis and/or a stratification determination based on at least one of the amount of time after the event or the length of time elapsed monitoring the patient. An event is preferably at least one of a surgery, medication administration, intubation, extubation, lab tests, and a medical procedures, and patient care action. The parameters are preferably at least one of physiological parameters, demographics, location, clinical events, treatments, physical state, and lab test results. Preferably, the parameters are obtained from sensors or inputs that measure Minute ventilation (MV) and/or % of predicted MV, Tidal volume (TV), Respiratory rate (RR), Ventilation flow-volume relationship, Peripheral blood oxygen saturation (SpO2), Mixed venous oxygen saturation (SvO2), End-tidal carbon dioxide (EtCO2), Sublingual and/or transcutaneous CO2, temperature, Cardiac Output (CO), Cardiac index, Perfusion, Blood pressure (BP), Heart Rate (HR), Electrocardiogram (ECG), Renal fluid volumes and rates, Pain level scores and locations, Medication information, Patient location, Present and prior patient diagnoses and stratification of risk based on different clinical evaluation techniques, Temporal and ratiometric relationships of parameter measurements with respect to patient locations, Variation and rate of variation thereof, or Temporal and ratiometric relationships thereof.

In a preferred embodiment, the diagnosing and/or stratifying of the patient is based on at least one of supervised and unsupervised learning techniques, machine learning, Bayesian inference networks, expert systems, principal component analysis, support vector machines, time series forecasting and analysis, fractal analysis, statistical techniques, heuristic algorithms, deep temporal continuous and discontinuous clustering that integrates dimensionality reduction and temporal clustering into a single end-to-end learning framework, maximum margin temporal clustering, fuzzy logic, and neural networks. Preferably, the diagnosis and/or stratifications are compared to a database of historic diagnosis and/or stratifications. In a preferred embodiment, feedback from caregivers is updated in the database for future diagnosis and/or stratifications. Preferably, the patient parameters include independent measurements of tidal volume (TV) and respiratory rate (RR) of the patient. The TV and RR are preferably indicative of a patient's status.

Another embodiment is directed to a method for evaluating a patient. The method comprises the steps of: obtaining tidal volume (TV) and respiratory rate (RR) of the patient, and diagnosing the patient based on independent measurements of TV and RR.

Preferably, the TV and RR are obtained from the same sensor. The sensor is preferably a respiratory impedance sensor. The method preferably further comprises providing an alert if the TV or RR is outside a predetermined range. Preferably, the TV and RR are independent variables. The method is preferably used to evaluate a rapid shallow breathing index. Preferably, the TV and RR are indicative of a patient's status.

Another embodiment of the invention is directed towards a system for evaluating a patient. The system comprises a sensor adapted to obtain tidal volume (TV) and respiratory rate (RR) of the patient, and a processor adapted to diagnose the patient based on independent measurements of TV and RR.

In a preferred embodiment, TV and RR are obtained from the same sensor. Preferably, at least one sensor is a respiratory impedance sensor. The processor preferably provides an alert if TV or RR is outside a predetermined range. Preferably, the TV and RR are independent variables. In a preferred embodiment, the system is used to evaluate a rapid shallow breathing index. Preferably, the TV and RR are indicative of a patient's status.

Another embodiment of the invention is directed towards a method of evaluating a patient. The method comprises the steps of obtaining temporal data of the patient after an event, determining a state or change in state of the patient based on the temporal data, and alerting medical staff of the state or change in state.

In a preferred embodiment, the temporal data is used for diagnosing and/or stratifying the patient based on the state of the patient and alerting medical staff of a diagnosis and/or stratification. Preferably, the temporal data is used to weight the diagnosis and/or stratification determination based on at least one of the amount of time after the event or the length of time elapsed monitoring the patient. A event is preferably at least one of a surgery, medication administration, intubation, extubation, lab tests, and a medical procedures, and patient care action.

Preferably, the diagnosing and/or stratifying of the patient is based on at least one of supervised and unsupervised learning techniques, machine learning, Bayesian inference networks, expert systems, principal component analysis, support vector machines, time series forecasting and analysis, fractal analysis, statistical techniques, heuristic algorithms, deep temporal continuous and discontinuous clustering that integrates dimensionality reduction and temporal clustering into a single end-to-end learning framework, maximum margin temporal clustering, fuzzy logic, and neural networks. In a preferred embodiment, the diagnosis and/or stratifications are compared to a database of historic diagnosis and/or stratifications. Preferably, feedback from caregivers is updated in the database for future diagnosis and/or stratifications.

Another embodiment of the invention is directed to a system of evaluating a patient. The system comprises a processor adapted to: obtain temporal data of the patient after an event, determine a state or change of state of the patient the temporal data, and alert medical staff of the state or change in state.

In a preferred embodiment, the temporal data is used for diagnosing and/or stratifying the patient based on the state of the patient and alerting medical staff of a diagnosis and/or stratification. Preferably, the temporal data is used to weight the diagnosis and/or stratification determination based on at least one of the amount of time after the event or the length of time elapsed monitoring the patient. Preferably, an event is at least one of a surgery, medication administration, intubation, extubation, lab tests, and a medical procedures, and patient care action.

The diagnosing and/or stratifying of the patient is preferably based on at least one of supervised and unsupervised learning techniques, machine learning, Bayesian inference networks, expert systems, principal component analysis, support vector machines, time series forecasting and analysis, fractal analysis, statistical techniques, heuristic algorithms, deep temporal continuous and discontinuous clustering that integrates dimensionality reduction and temporal clustering into a single end-to-end learning framework, maximum margin temporal clustering, fuzzy logic, and neural networks. Preferably, the diagnosis and/or stratifications are compared to a database of historic diagnosis and/or stratifications. Feedback from caregivers is preferably updated in the database for future diagnosis and/or stratifications.

Other embodiments and advantages of the invention are set forth in part in the description, which follows, and in part, may be obvious from this description, or may be learned from the practice of the invention.

DESCRIPTION OF THE FIGURES

The invention is described in greater detail by way of example only and with reference to the attached drawings, in which.

DESCRIPTION OF THE INVENTION

Figure 1:
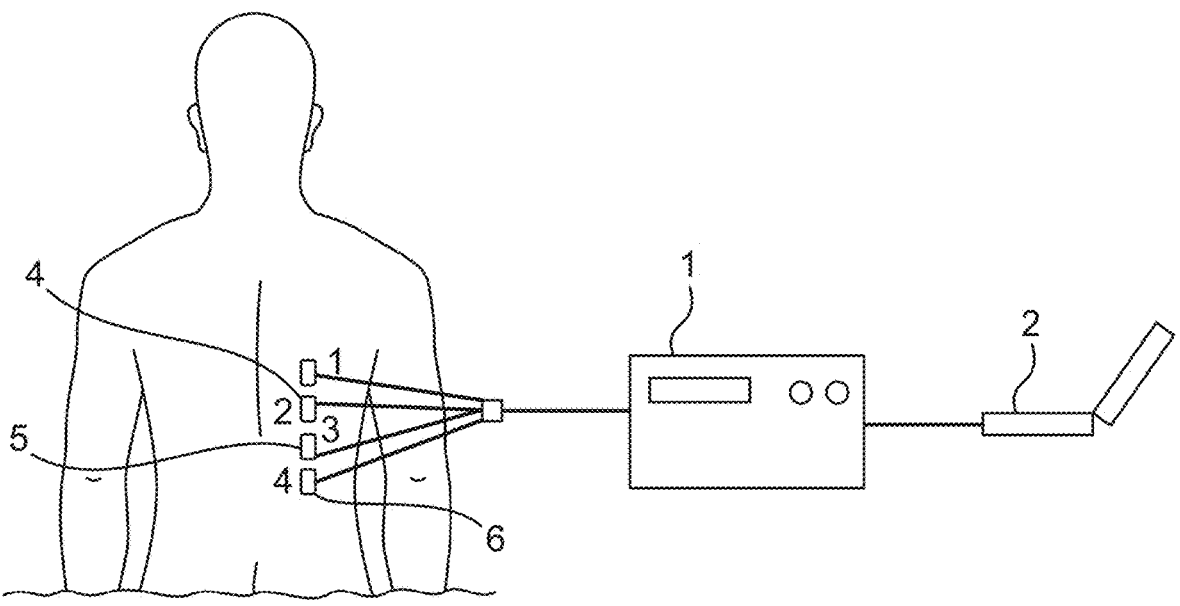
FIG. 1 is a perspective view of a four-lead embodiment of the invention.

As embodied and broadly described herein, the disclosures herein provide detailed embodiments of the invention. However, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention.

One embodiment of the present invention is directed to a system and a method to that uses temporal information of physiologic measurements, alarm events, patient information, and other available medical information to diagnose patients with conditions and to generate scores for warning systems for medical staff.

Preferably, the amount of time passed since an event, such as a surgery, medication administration, intubation, extubation, lab tests, and other medical procedures and patient care actions taken, is used as an input to the system making decisions on patient diagnosis, deterioration, and generating early warning scores.

In another embodiment, the temporal information of physiologic measurements is used to qualify the accuracy of the measurements. For example, the accuracy of some medical devices, such as intravenous blood pressure catheters, degrades over time. Preferably the system uses the duration of monitoring, the lifespan of the sensor, and the historical effectiveness of the sensor to qualify and weight the accuracy of the measurement from medical devices. Furthermore, the duration of use of a sensor or monitor is used to identify the alarms resulting from such measurements as either "true" or "false", or to calculate the probability of an incorrect measurement or alarm event.

In another embodiment the system and method takes into account the location of the patient and the acuity of care in such location to qualify the data and alarms from physiologic monitors, predictive algorithms and. The system and method appropriately weighs the location of the patient (emergency room, post-anesthesia care unit, general hospital floor, medical or surgical intensive care unit, outpatient procedure suite, operating room, etc) in order to qualify the physiologic measurement, the alarm and the diagnosis.

In another embodiment, respiratory metrics including minute ventilation, tidal volume, respiratory rate, flow-volume loop shape and metrics, rapid shallow breathing index (RSBI), slow deep breathing index (SDBI), and ratios and combinations of such metrics are used to generate decisions, diagnoses and stratifications of patients for outcomes including but not limited to sepsis, congestive heart failure, hypovolemia, hypertension (systemic and/or pulmonary), COPD (emphysema, fibrosis), pulmonary embolism, renal failure, respiratory depression, respiratory failure, hypoxia, changes in metabolism, stratification of risk to develop the above conditions, stratification of acuity of care necessary for each patient, etc.

Preferably respiratory metrics mentioned above, measured in either intubated or non-intubated patients, are used to calculate an early warning score or decide on a diagnosis for disease states including but not limited to sepsis, congestive heart failure, hypovolemia, hypertension (systemic and/or pulmonary), COPD (emphysema, fibrosis), pulmonary embolism, renal failure, respiratory depression, respiratory failure, hypoxia, respiratory compromise caused by coronavirus, changes in metabolism, stratification of risk to develop the above conditions, stratification of acuity of care necessary for each patient, etc. Preferably the system uses minute ventilation and tidal volume measurements, as well as other available physiologic measurements including heart rate, temperature, blood pressure, blood oxygenation, etc to identify early symptoms of disease states. Preferably respiratory metrics are used in conjunction with unsupervised and supervised learning techniques including but not limited to machine learning, Bayesian inference networks, expert systems, principal component analysis, fractal analysis, statistical techniques, heuristic analysis, deep temporal continuous and discontinuous clustering that integrates dimensionality reduction and temporal clustering into a single end-to-end learning framework, maximum margin temporal clustering, fuzzy logic, and neural networks, to calculate an early warning score or decide on a diagnosis for sepsis.

Preferably, the ratios of respiratory metrics are used as independent inputs to a system for decision, diagnosis and stratification. For example the ratio of TV to RR can be dependent on the stiffness of the lungs, such that the ratio is high in cases of congestive heart failure where the lungs are stiff due to fluid, but the ratio is low in cases of COPD where the lungs are too compliant. Preferably the ratio of TV to RR is used in conjunction with supervised and unsupervised learning techniques to diagnose either congestive heart failure or COPD. Preferably, the flow-volume relationship from which the respiratory metrics are derived are also used to detect changes in lung stiffness by observing changes in the flow-volume loops, either by an automated system or presenting data to clinicians for confirmation.

In another embodiment, the system diagnoses opioid sensitivity by using opioid administration events, their dosage and timing, along with respiratory metrics, including minute ventilation, tidal volume, respiratory rate, the ratios of respiratory metrics, the variability of respiratory metrics, etc.

In a preferred embodiment, inputs in Table 1 are used as independent predictors for diagnosis, decision, and stratification of patients. Preferably, respiratory metrics are used to diagnose disease states including but not limited to respiratory depression or respiratory failure as a result of an opioid response, obstructive sleep apnea, chronic obstructive pulmonary disease, sepsis, hypovolemia, congestive heart failure, etc. Preferably, the temporal trends in inputs to the system are taken in the context of previous events including but not limited to such as a surgery, medication administration, intubation, extubation, lab tests, and other medical procedures and patient care actions taken, etc., in order to diagnose disease states.

Preferably, the impedance measurement is based on a plurality of remote probe data sets, and wherein the programmable element is further programmed to enhance at least one of the plurality of remote probe data sets; or to stabilize at least one of the plurality of remote probe data sets; or to analyze each of the plurality of remote probe data sets for dynamic range and signal to noise ratio (SNR)

TABLE 1

| Inputs | Opioid Response | Obstructive Sleep Apnea | Sepsis | Hypovolemia | Congestive Heart Failure | Chronic Obstructive Pulmonary Disease (COPD) |
|---|---|---|---|---|---|---|
| Minute Ventilation (MV) | ↓ | ↓ | ↑ | ↑ | ↑ | ↑ |
| Tidal Volume (TV) | ↓ | ↓ or ↑ (compensated vs uncompensated) | ↑ or = | ↑ or = | ↓ or = | ↑ |
| Respiratory Rate (RR) | ↓ or = | ↓ | ↑ or = | ↑ or = | ↑ | ↓ or = |
| Heart Rate (HR) | ↓ | | ↑ | ↑ | | ↑ |
| Blood Pressure (BP) | ↓ | | ↓ | ↓ | ↓ | = |
| Blood Oxygenation (SpO₂) | ↓, late | ↓, late | ↓ or =, late | ↓, late | ↓, early | ↓, late |

In another embodiment, the timing of events and alarms from a hospital network is used to calculate a-priori probabilities of events in similar patients, which can then be used to qualify alarm events in patients in real-time. Preferably, current alarm events are used in conjunction with historical alarm events to update probabilities of events in real time.

In another embodiment, the system uses information from various physiological parameters, demographics, clinical events, treatments, lab test results as inputs to qualify alarm events as "true" or "false" or to calculate the probability of a valid alarm, either in real-time or retrospectively. Preferably, medical staff has the option to confirm or override alarms event validity. In another embodiment, the real-time or retrospective feedback from medical staff is used to update the current status of alarms, and/or to train via supervised or unsupervised learning techniques, the criteria for future alarms based on the external information provided by medical staff.

In a preferred embodiment, after an alarm has been sounded the system uses the duration after the alarm has sounded but before it has been addressed by medical staff in order to collect data to qualify the alarm retrospectively. Preferably, the system cancels the alarm if it is deemed to be a "false" alarm, but has not yet been addressed by medical staff. In another embodiment, the system updates the medical staff of the false alarm or the cancellation of the sounding alarm with the criteria used for the cancellation.

In a preferred embodiment, the system uses retrospective analysis and medical staff feedback to identify incessant false alarm events and the monitors contributing to alarm fatigue.

One embodiment of the present invention is directed to a device for assessing a patient, individual or animal that collects impedance measurements by placing multiple electrode leads and/or speakers and microphones on the body. Preferably at least one impedance measuring element and a microphone/speaker functionally connected to a programmable element, programmed to provide an assessment of at least one respiratory parameter of the subject.

values. Preferably, the device probes are maintained in several lead configurations. In one embodiment, variations in lead configuration allow for flexibility depending on the subject and test being performed. In other embodiments, variations in lead configuration allow for variability in patient anatomy. Preferably, the device maintains settings to identify valid lead configurations. Preferably, the device maintains settings to identify valid lead attachment.

Preferably, the device or method as described in a protocol embedded in the machine instructs as to lead placement. Preferably, appropriate lead contact is verified by the device. Preferably, the device alerts the operator as to inadequate or inappropriate lead placement. Preferably, the device monitors continuously or intermittently and maintains alarms to indicate when a respiratory parameter reflects a loss in ventilation or other vital function. The alarm is set based on a respiratory sufficiency index, on minute ventilation, on respiratory rate, on tidal volume, on an inspiratory volume or flow parameter, on an expiratory volume or flow parameter, on variability of respiratory rate, volume, flow or other parameter generated. For example, the alarm goes off if the monitor detects a decrease in either respiratory frequency or depth or minute ventilation associated with hypoventilation or detects an increase in any or all of these parameters that would suggest hyperventilation. An alarm is used on a hospital floor in comparing the patient's current respiratory status with a baseline level based on specific individual calibration to ventilator or spirometer. Preferably, the alarm is set based on parameters taken for the given individual from a ventilator or spirometer. More preferably the baseline level is based on one or more of the following: demographic, physiologic and body type parameters. An alarm is also used to alert for narcotic induced respiratory depression at a point that is determined to be detrimental to the patient. Preferably, the ranges of values beyond which alarms will be triggered are chosen by the physician or care giver for one or more of the following: respiratory rate, tidal volume, minute ventilation, respiratory sufficiency index, shape of the respiratory curve, entropy, fractal or other analysis parameters associated with respiratory variability or complexity.

In another embodiment, the RVM measurements taken at any given point in time is recorded as baseline. These recorded values are correlated to subjective impression by a physician or other health care worker of patient status. Subsequently, RVM is monitored and an alarm set to alert health care staff if a 10%, 20% or other selected percentage change in respiratory volumes, minute ventilation curve characteristics, or variability is noted.

The following illustrate embodiments of the invention, but should not be viewed as limiting the scope of the invention.

Impedance Plethysmograph

As embodied and broadly described herein are provided detailed embodiments of the invention. The embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention.

The invention preferably comprises an impedance pneumograph with integrated electronics to convert measured impedance values to volume and display the volume to an end-user through an electronic interface or printed reports employing numerical or graphical representations of the data. The impedance measuring device comprises circuitry, at least one microprocessor and preferably at least four leads. Preferably, where at least two leads are used for injecting current into the subject's body and at least two are used for reading the voltage response of said patient's body.

In one embodiment, the device preferably comprises an integrated module to simulate a patient and allow for automated system testing and demonstrations. Automated system tests improve the performance of the device and ensure that it is functioning correctly before use.

In the preferred embodiment, the device utilizes an analog divider to compensate for slight deviations in the injected current and increase the accuracy of acquired data. The analog divider in the preferred embodiment would be placed after the demodulator and before the rectifier. In other embodiments the analog divider may be placed in other locations in the circuit including, but not limited to, after the precision rectifier or before the demodulator.

In the preferred embodiment, the device utilizes adaptive electronics driven by a microprocessor to maintain the appropriate gains on the different amplifiers in the circuit to prevent the signal from going out of range. The microprocessor tracks the set gains at each of the hardware amplifiers and compensates appropriately during its calculations so that it always outputs an appropriate value.

The impedance measuring device is preferably connected to computer via a digital interface (e.g. USB, Fire wire, serial, parallel, or other kind of digital interface). The digital interface is used to prevent data from corruption during transfer. Communication over this interface is preferably encrypted to further ensure data integrity as well as protect the invention from usage of counterfeit modules (either measuring device or computer).

Referring now to a preferred embodiment of the invention in more detail, in FIG. 1 there is shown an impedance plethysmograph, comprising a radio frequency impedance meter 1, a programmable element 2 contained on a PC linked to the meter, which is connected to the patient by four leads, namely a first lead 3, a second lead 4, a third lead 5, and a fourth lead 6. Each lead is preferably connected to a surface electrode, namely a first surface electrode, a second surface electrode, a third surface electrode, and a fourth surface electrode.

In further detail, still referring to the embodiment of FIG. 1, the electrodes can be made of a conductive material such as AgCl, coated with an adhesive, conductive material such as a hydrogel or hydrocolloid. The leads can be made of any conductive material such as copper wire and are preferably coated with insulating material such as rubber. In a preferred embodiment, wireless electrodes are utilized to provide current and collect and transmit data. Preferably, this lead composition is coupled with Bluetooth technology and a receiver.

Leads 1 and 4 are connected to a current source with a constant frequency preferably greater than 20 KHz, which is great enough to avoid interfering with biological signaling. The amplitude of the current source is preferably less than 50 mA, and below the level that would cause fibrillation at the chosen frequency. The differential voltage between leads 2 and 3 is used to calculate the impedance according to ohm's law. By sampling the voltage measurements taken by the impedance meter, the programmable element (such as a PC) tracks and plots changes in thoracic impedance that correspond to biological functions such as heartbeat and breathing. The changes in impedance are then used to monitor pulmonary function. Preferably, the device is calibrated by a method laid out herein to calculate the lung volumes and display them to an operator.

Figure 28:
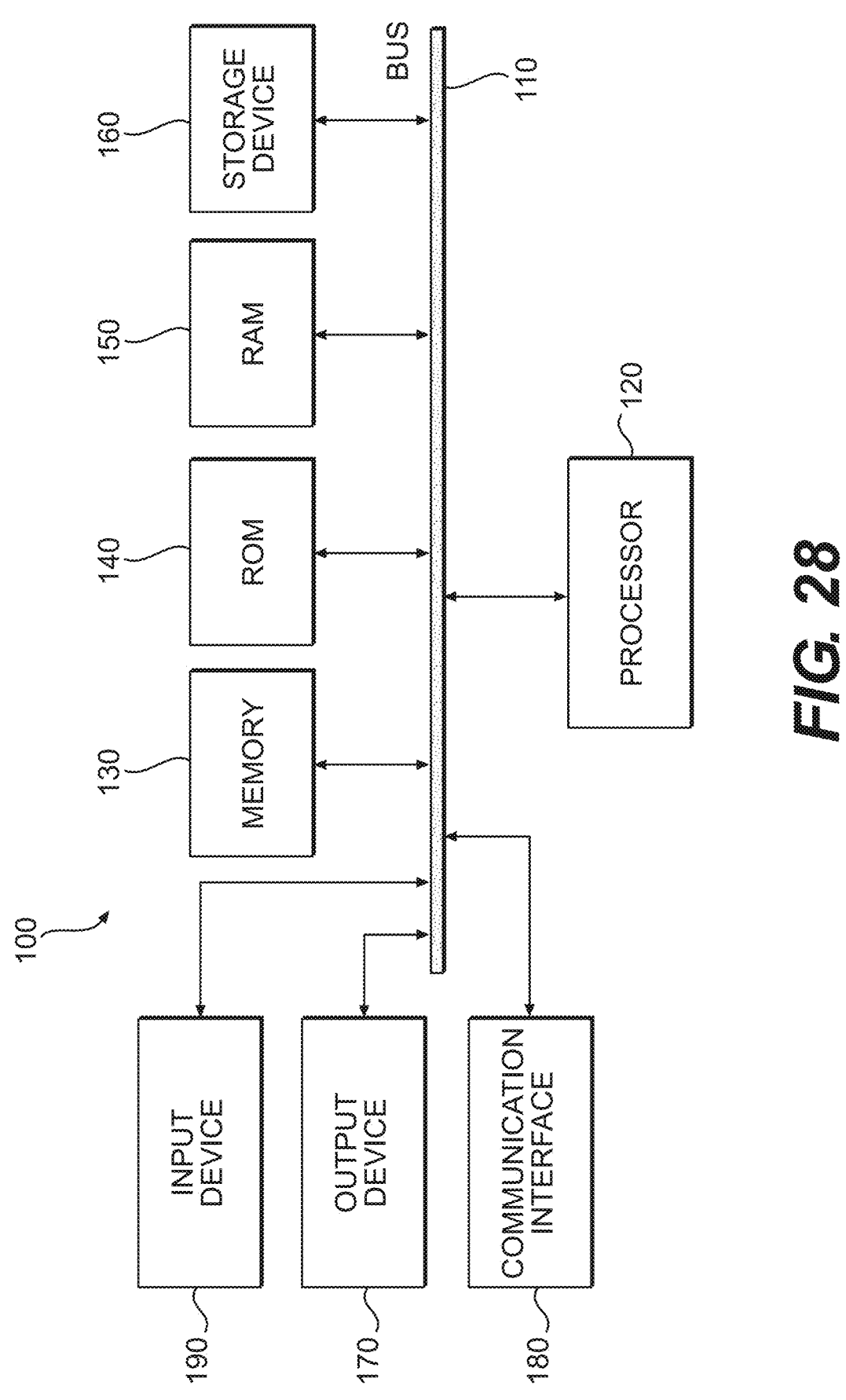
FIG. 28 illustrates an embodiment of a system of the invention.
Figure 29:
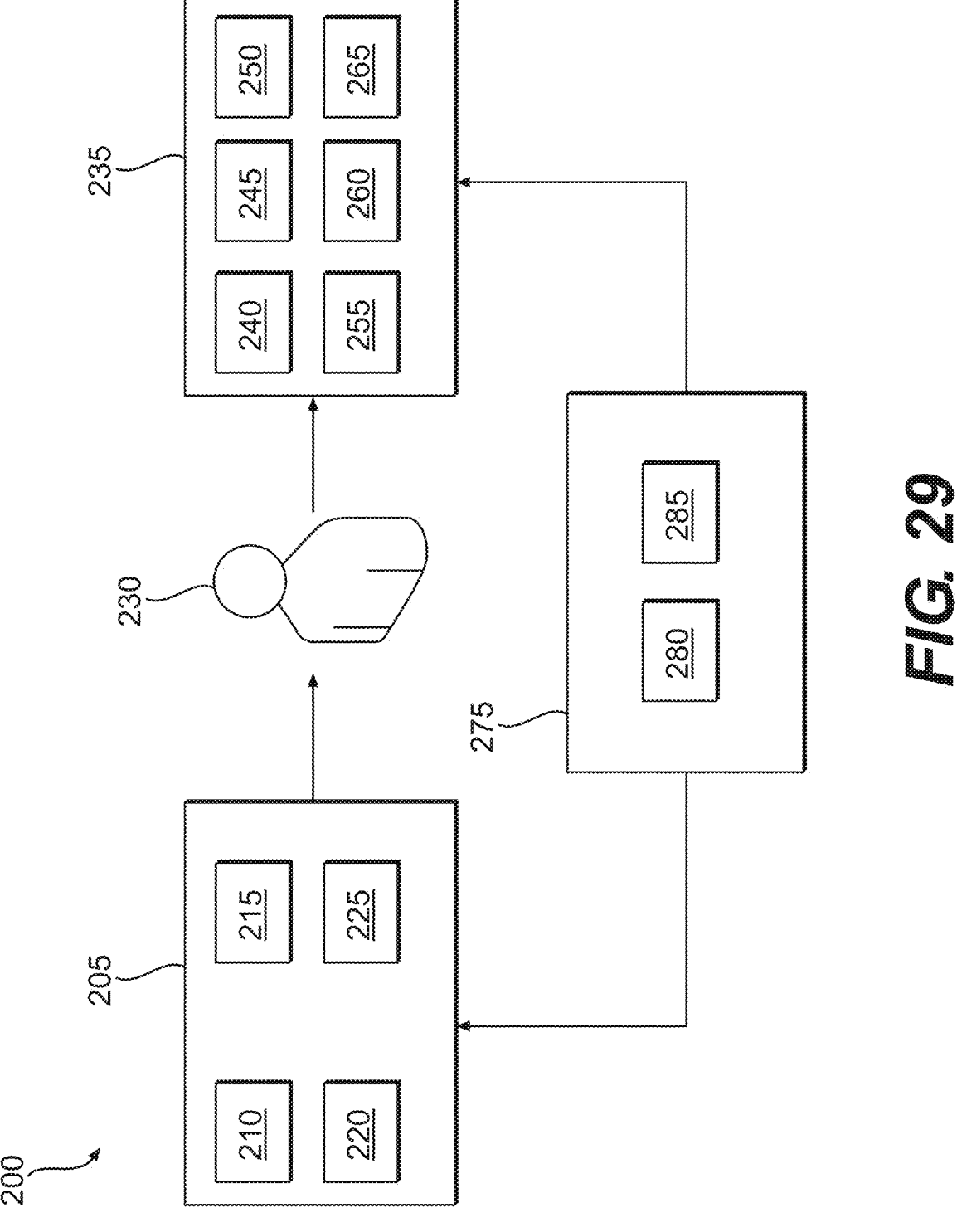
FIG. 29 illustrates an embodiment of the device of the invention.

With reference to FIG. 28, an exemplary and preferred system includes at least one general-purpose computing device 100, including a processing unit (CPU) 120, and a system bus 110 that couples various system components including the system memory such as read only memory (ROM) 140 and random access memory (RAM) 150 to the processing 25 unit 120. Other system memory 130 may be available for use as well. The invention preferably operates on a computing device with more than one CPU 120 or on a group or cluster of computing devices networked together to provide greater processing capability. The system bus 110 may be any of several types of bus structures including a memory bus or memory controller, a peripheral bus, and a local bus using any of a variety of bus architectures. A basic input/output (BIOS) stored in ROM 140 or the like, preferably provides the basic routine that helps to transfer information between elements within the computing device 100, such as during start-up. The computing device 100 further preferably includes storage devices such as a hard disk drive 160, a magnetic disk drive, an optical disk drive, tape drive or the like. The storage device 160 is connected to the system bus 110 by a drive interface. The drives and the associated computer readable media provide nonvolatile storage of computer readable instructions, data structures, program modules and other data for the computing device 100. The basic components are known to those of skill in the art and appropriate variations are contemplated depending on the type of device, such as whether the device is a small, handheld computing device, a desktop computer, a laptop computer, a computer server, a wireless devices, web-enabled devices, or wireless phones, etc.

In some embodiments, the system is preferably controlled by a single CPU, however, in other embodiments, one or more components of the system is controlled by one or more microprocessors (MP). Additionally, combinations of CPUs and MPs can be used. Preferably, the MP is an embedded microcontroller, however other devices capable of processing commands can also be used.

Although the exemplary environment described herein employs the hard disk, it should be appreciated by those skilled in the art that other types of computer readable media which can store data that are accessible by a computer, such as magnetic cassettes, flash memory cards, digital versatile disks, cartridges, random access memories (RAMs), read only memory (ROM), a cable or wireless signal containing a bit stream and the like, may also be used in the exemplary operating environment. To enable user interaction with the computing device 100, an input device 190 represents any number of input mechanisms, such as a microphone for speech, a touch sensitive screen for gesture or graphical input, electrical signal sensors, keyboard, mouse, motion input, speech and so forth. The device output 170 can be one or more of a number of output mechanisms known to those of skill in the art, for example, printers, monitors, projectors, speakers, and plotters. In some embodiments, the output can be via a network interface, for example uploading to a website, emailing, attached to or placed within other electronic files, and sending an SMS or MMS message. In some instances, multimodal systems enable a user to provide multiple types of input to communicate with the computing device 100. The communications interface 180 generally governs and manages the user input and system output. There is no restriction on the invention operating on any particular hardware arrangement and therefore the basic features here may easily be substituted for improved hardware or firmware arrangements as they are developed.

Embodiments within the scope of the present invention may also include computer readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures. When information is transferred or provided over a network or another communications connection (either hardwired, wireless, or combination thereof) to a computer, the computer properly views the connection as a computer-readable medium. Thus, any such connection is properly termed a computer readable medium. Combinations of the above should also be included within the scope of the computer-readable media.

Computer-executable instructions include, for example, instructions and data which cause a general purpose computer, special purpose computer, or special purpose processing device to perform a certain function or group of functions. Computer-executable instructions also include program modules that are executed by computers in standalone or network environments. Generally, program modules include routines, programs, objects, components, and data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Those of skill in the art will appreciate that other embodiments of the invention may be practiced in network computing environments with many types of computer system configurations, including personal computers, hand-held devices, multi-processor systems, microprocessor-based or programmable consumer electronics, network PCs, minicomputers, mainframe computers, and the like. Networks may include the Internet, one or more Local Area Networks ("LANs"), one or more Metropolitan Area Networks ("MANs"), one or more Wide Area Networks ("WANs"), one or more Intranets, etc. Embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

Figure 2:
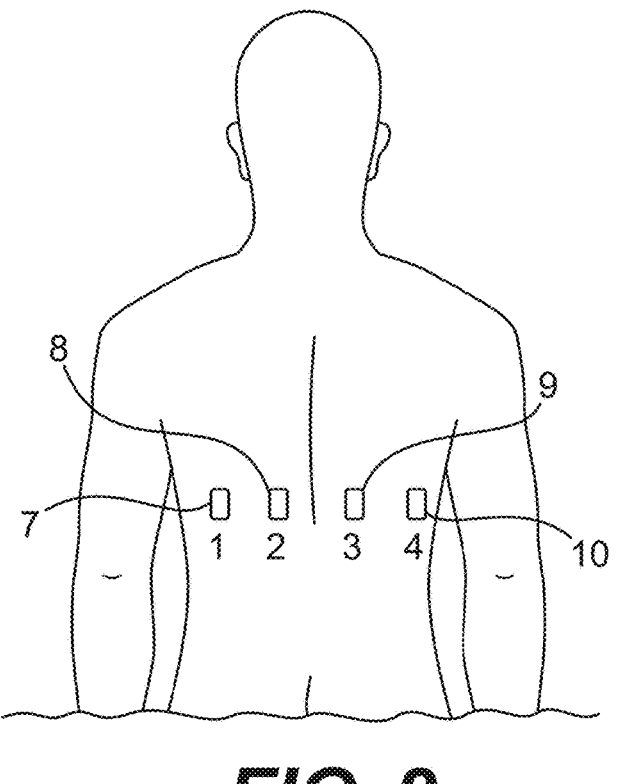
FIG. 2 is a diagram of the Posterior Left to Right electrode configuration.

FIG. 2 is a schematic of an embodiment of a system 200 of the invention. The electrical source originates from signal source 205. Preferably, an adjustable function generator 210 (e.g. a XR2206 chip) is used to generate the electrical source. The function generator 210 is preferably adjustable via a microprocessor (MP) 275 or manually. In some embodiments, the function generator can be tuned in order to improve the signal. Tuning can occur once or multiple times. Bio-impedance spectroscopy can be used to detect levels of hydration at different frequencies, which can be used to calibrate function generator 210. Similarly, body fat percentages can be calculated. Signal source 205 also comprises a current generator 215 (e.g. a Howland circuit). Current generator 215 preferably keeps the source current constant despite changes in pad contact (unless the contact is totally broken). In the preferred embodiment, current generator 215 can be tuned to improve performance, which can be done manually or automatically by the MP 275. The impedance measuring subsystem may utilize current generating components at one or more frequencies, which may be active simultaneously, or sequentially. Voltage measuring components may be functionally connected to one or more electrodes. The impedance measuring subsystem may utilize non-sinusoidal current, such as narrow current pulses. The system may integrate additional sensors, such as accelerometers, moisture and acoustics sensors, capnography or oximetry sensors.

In preferred embodiments, the pad contact quality is monitored and a warning is produced when the pad contact is broken or too poor quality for the electronics to compensate. Signal source 205 may also comprise a current monitor 220 to calculate impedance. In a preferred embodiment, signal source 205 also comprises a patient simulator 225. Patient simulator 225 can simulate changes in the impedance with parameters similar to a real patient. Patient simulator 225 can be used for testing system 200 as well as calibration of the circuitry.

Figure 30:
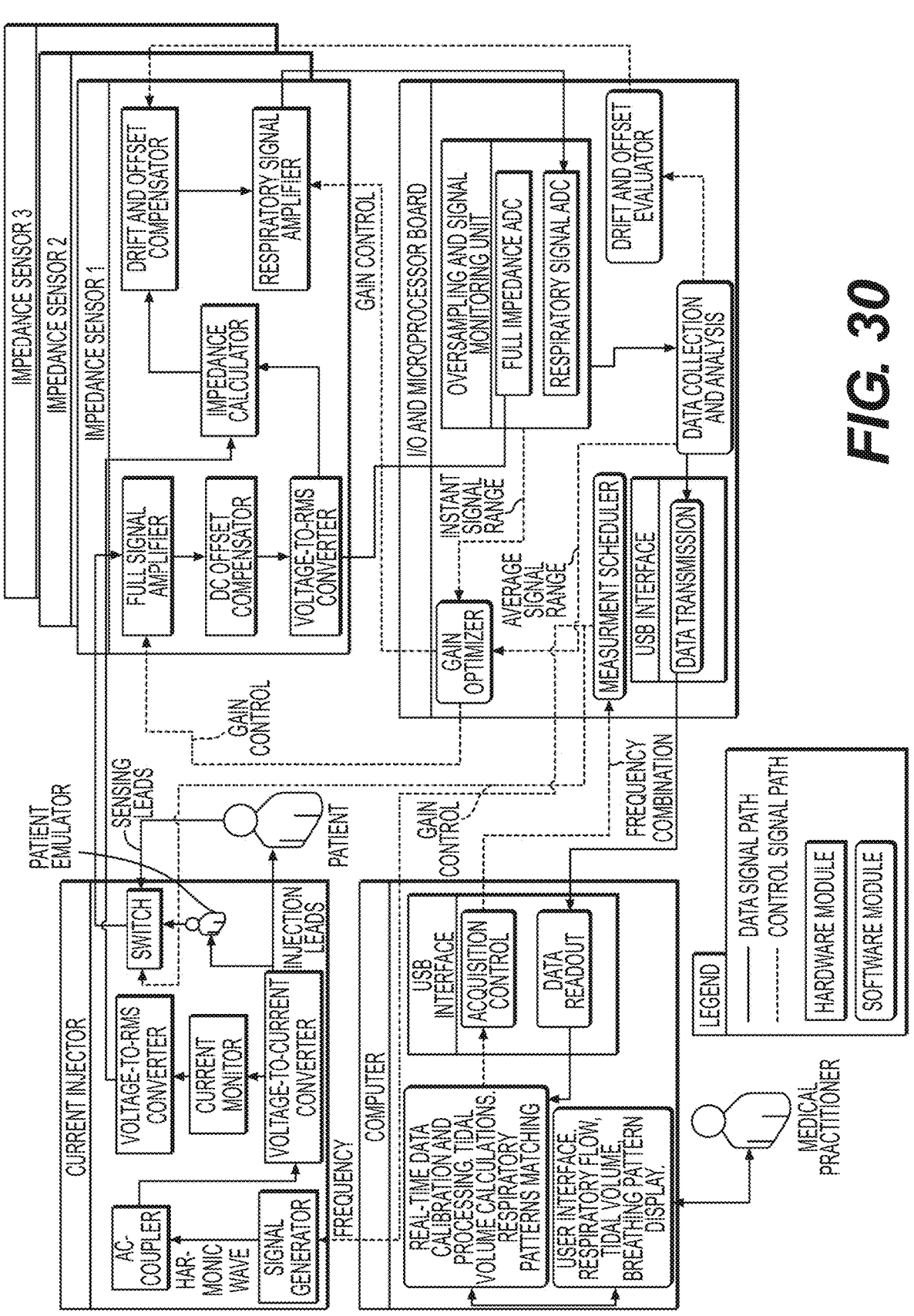
FIGS. 30-32 illustrate preferred embodiments of devices of the invention.
Figure 31:
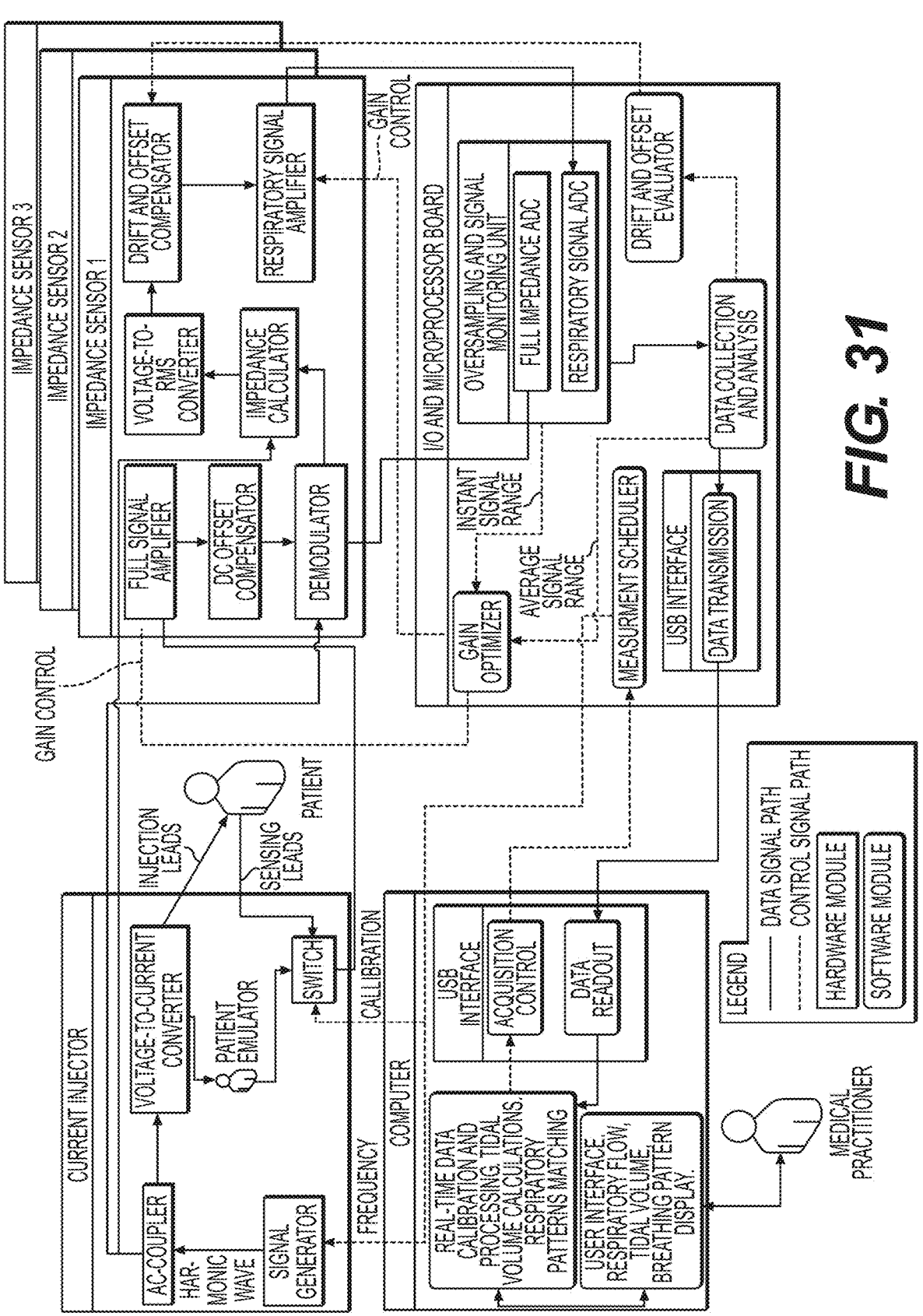

The signal from signal source 205 passes through patient 230 and is received by sensor 235. Preferably, sensor 230 comprises an input amplifier 240. Input amplifier 240 suppresses the effect of poor or variable pad contact on measurement. The gain of input amplifier 240 is preferably controlled by the MP 275 to provide an enhanced signal to the other modules. Sensor 230 preferably also comprises a signal filter 245 to remove interference from the power grid, etc. Signal filter 245 may be a standard high-pass filter (as on FIG. 30), a demodulator (as on FIG. 31), or another signal filter. Synchronous demodulators are often used for detecting bio-impedance changes and stripping out motion artifacts in the signal.

Figure 32:
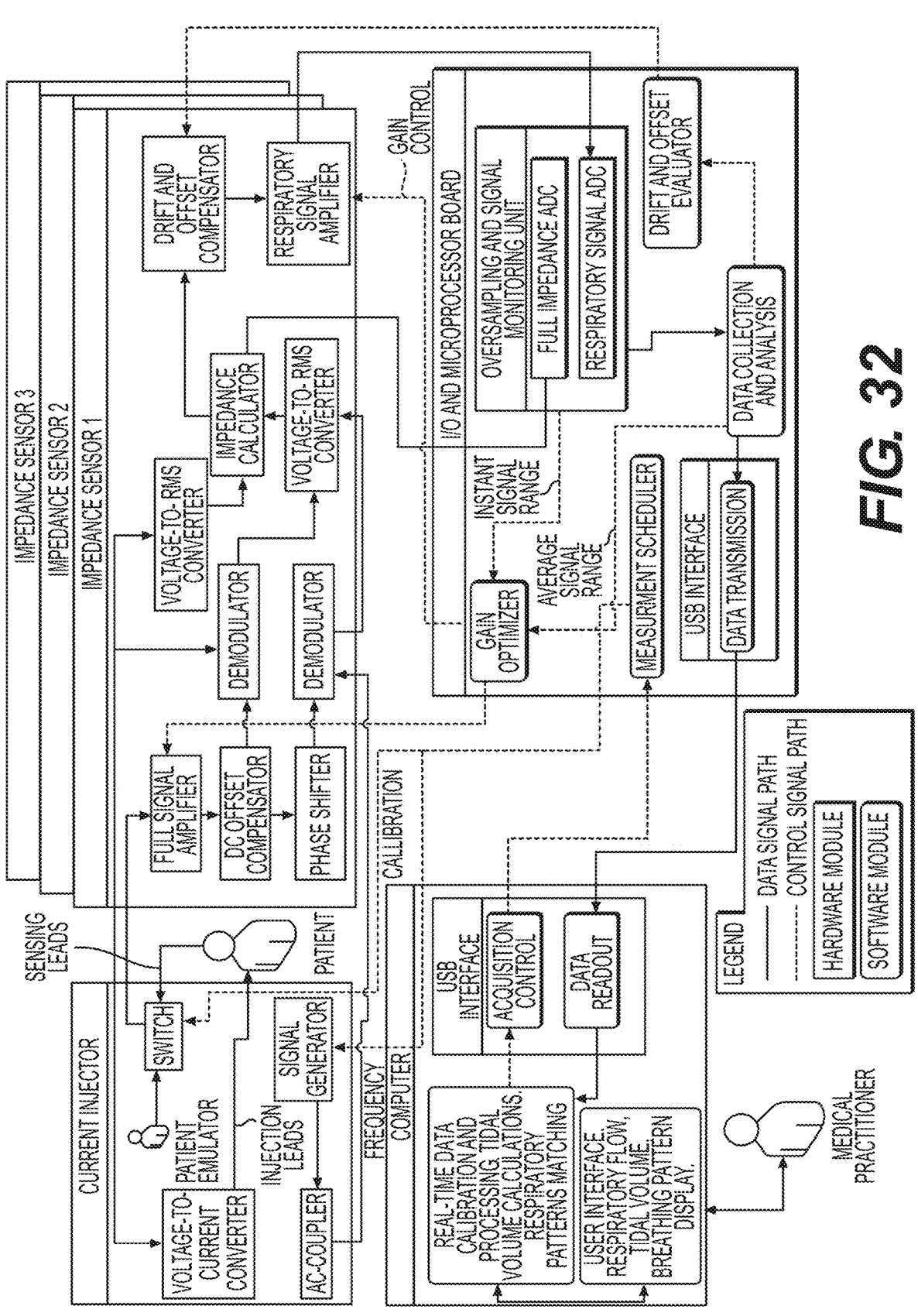

In a preferred embodiment, the signal is split into two paths (as on FIG. 32). The first path demodulates the measured signal using the generator signal as a carrier. The second path uses a 90-degree phase rotating circuitry before demodulation. Both demodulated signals can be converted into RMS values using voltage-to-RMS converters. Measured separately, the signals are summed and then the square root is calculated. This allows for compensation for any phase shift in the subject and for separate measurements of resistance and reactance, which provides valuable information for motion artifact compensation as well as hydration levels, fat percentages, and calibration coefficient calculations.

Additionally, sensor 230 may comprise an analog divider 250, which divides the measured voltage signal by the signal from the current monitoring circuit to calculate impedance. Sensor 230 preferably also comprises a precision rectifier or root mean square to direct current (RMS-to-DC) chip 255 with a low pass filter to remove the carrier frequency. The output of sensor 230 is preferably a DC signal proportional to the patient's impedance. Sensor 230 may also comprise a band-pass filter 260 to select only the respiratory rates by filtering out the portion of the signal not corresponding to the respiration. Band-pass filter 260 may be calibrated manually or automatically by the MP 275. Preferably, sensor 230 comprises a multiplexor 265 controlled by the MP 275 to accommodate multiple probe pairs. Preferably there are 2 probe pairs, however more or fewer probe pairs are contemplated. Sensor 230 may also comprise an output amplifier 270. Output amplifier 270 is preferably controlled by the MP 275 and provides a signal to an analog-to-digital converter (ADC) 280 for high precision digitization. Oversampling is used to reduce measurement noise which may originate from different sources (e.g., thermal, electronic, biological, or EM interference). MP 275 commands ADC to take measurements with as high a cadence as possible and then averages the obtained data over the time intervals corresponding to the sampling frequency. The sampling frequency is the frequency of the impedance sampling as it is presented to the computer by the impedance measuring device. The frequency is preferably set sufficiently high to monitor all the minute features of respiration.

Using controllable gains and oversampling preferably allows the system to measure the impedance with extremely high effective precision (estimated 28-bit for current implementation, or 4 parts per billion).

Both signal source 205 and sensor 230 are controlled by MP 275. MP 275 preferably comprises at least one ADC 280 monitoring the signal processing, and at least one digital output 285 to control the digital potentiometers, multiplexors, op-amps, signal generator, and other devices. Preferably, MP 275 and a computer interface (e.g., via a USB interface, a serial interface, or a wireless interface).

Preferably, the MP computes values for respiratory rate (RR), tidal volume (TV) and minute ventilation (MV) as well as, tracks the trends in computed RR, TV, or MV values and performs statistical, factor, or fractal analysis on trends in real-time. The MP may tracks instantaneous and cumulative deviations from predicted adequate values for RR, TV, or MV and computes a respiratory sufficiency index (RSI).

In a preferred embodiment, the system has the capability to measure and record other parameters or disease states including but not limited to: temperature, blood pressure, Heart rate, SpO2, EtCO2, Arterial blood gas, acceleration/motion, GPS location, height, weight, BMI, diagnosis of OSA, CHF, Asthma, COPD, ARDS, OIRD, Minute Ventilation, cardiac output, end tidal CO2, oxygen perfusion, ECG and other electrophysiologic measurements of the heart. In a preferred embodiment, the impedance measuring device measures impedance cardiography and impedance pneumography simultaneously. Preferably, the additional parameters are displayed on-screen. Preferably, the respiratory impedance data are combined with the additional parameters in a meaningful way to act as an adjunct to diagnosis. Preferably, the impedance data alone, or combined with one or more additional parameters are used to provide a diagnosis of a disease state.

In one embodiment, measurements are taken from each side of the chest independently and used to evaluate both general pulmonary status and differences between right and left lung aeration or chest expansion. An example of this is, in the case of rib fractures, where there can be changes attributed to damage including pulmonary contusion, decrease in motion due to splinting or pneumothorax where both sides of the chest are monitored independently to provide side specific data. Other sources of localized pulmonary pathology can be evaluated including pneumonia, hydrothorax, chylothorax, hemothorax, hemo/pneumothorax, atelectasis, tumor, and radiation injury. In another embodiment, information from the device is used with information from an echocardiogram, radionuclide study or other method of imaging the heart. In a preferred embodiment the device assists in the diagnosis of myocardial ischemia with one of the following: ekg, advanced electrophysiologic studies, cardiac catheterization, echocardiogram, stress testing, radionuclide testing, CT, MRI, cardiac output monitoring by impedance measurement. In one embodiment the device provides information that is used to help with collection of other signals that vary with respiration such as respiratory sounds, cardiac information, radiation detection devices, radiation therapy devices, ablation devices. In a preferred embodiment the device can assist with the timing or data collection by another modality and/or using characteristics of the respiratory curve to correct data that is collected.

In one embodiment, the device provides information about breath-to-breath variability or respiratory complexity to be used in conjunction with cardiac beat to beat variability or complexity to provide otherwise unavailable information about cardiac, pulmonary systems, or overall metabolic or neurologic status.

Lead Configuration

The proposed respiratory parameters evaluation technique relies on a highly linear relation between the parameters and measured impedance. It is not true for every electrode placement. Extensive research was conducted to select best electrode placement which preferably satisfies following conditions:

1) Highly linear relation between respiratory volume and measured impedance variations (i.e. correlation values above 96%).
2) Low level of artifacts due to patient motion.
3) Low variation between repetitive electrode applications.
4) Easy application in common clinical situation. Capability for use with "universal calibration," which reliably determines scaling factors that depend on measurable patient body parameters without preliminary calibration with ventilator/spirometer.

Preferably, electrodes are attached horizontally to the mid-axillary line at the level of the sixth rib. Preferably, one electrode is placed at a stable location, such as immediately below the clavicle or at the sternal notch, and another electrode is place at the bottom of the ribcage or at the level of the xiphoid at the midaxillary line. However, the electrodes can be placed higher or lower on the thorax. Furthermore, electrodes may be placed in other locations and configurations (e.g. vertically along the thorax, at an angle across the thorax, or from a position on the front of the patient to a position on the back of the patent), depending on the subject to be tested, the test to be preformed, and other physiological concerns (e.g. if the patient has a pacemaker or other artificial device).

Preferably at least one impedance measuring element is present on one or more electrode leads. Preferably, two or more electrodes are arranged in a linear array, grid-like pattern, or in an anatomically influenced configuration. Preferably, four remote probes are arranged in a linear array. In another embodiment, multiple electrode leads are arranged as a net, vest, or array. Preferably, the one or more probes, electrode leads or sensors are placed on the thorax or abdomen of the subject. Preferably, the device uses single use electrodes. In other embodiments, the electrodes are hydrogel, hydrocolloids, or solid gels. Preferably, the electrode utilizes AgCl, nickel, or carbon sensors. Preferably, the electrodes come with soft cloth, foam, microporous tape, clear tape backing or another adhesive. Preferably, different, size appropriate electrodes exist for adults and neonates, with the adult electrodes larger than the neonatal ones, which are preferably 1" by ⅜" or less (2.54 cm by 0.95 cm or less). In other embodiments, sensor electrodes are the same as the probes that deliver electrical impulses to the body, or are different from the delivery electrodes, or are wireless and transmit data to a remote sensor. In another embodiment, the delivery probes are themselves sensors. In one embodiment, the stimulating electrode is battery powered. Preferably, the at least one respiratory parameter is recorded for a duration of 30 seconds, continuously, intermittently, for up to at least 3, 5, 10, 20, or 50 of the subject's breaths, for up to at least 100 of the subject's breaths, for up to at least 1000 of the subject's breaths, or for another duration. Preferably, the subject's impedance cardiogram is simultaneously recorded.

Preferably, the at least one impedance measuring element comprises one or more remote probes or electrode leads, or leads similar to standard EKG leads or similar to the leads used for measuring cardiac impedance, and wherein the programmable element is further programmed to analyze one or more remote probe or electrode lead data sets collected from the one or more remote probes or electrode leads.

In one embodiment of the invention, the impedance measurement subsystem reads impedance from multiple channels. In a preferred embodiment, a secondary voltage sensing channel is arranged at an angle to a primary voltage sensing channel. In one embodiment, the two channels share current generating electrodes. In one embodiment, the two channels also share one of the voltage sensing electrodes. Data from the two or more channels may be used in an adaptive algorithm to determine and suppress noise from motion.

Lead configuration is critical for the performance of the device in any embodiment. Preferably, one or more leads are placed on the thorax. In one embodiment, leads are placed on the thorax and abdomen to measure breathing from different regions of the body such as the thorax or the abdomen. Differences in the location of body motion associated with breathing produces information that is useful clinically for diagnosis of physiologic state and monitoring of disease and can be compensated for in calculations. Leads are placed on the thorax, neck and head in alternate configurations. In one embodiment, leads are placed in different configurations based on anatomic locations and spaced either according to specific measured distances or anatomic landmarks or a combination of both. In one embodiment, modifications of the spacing relative to body size are implemented. Preferably these modifications are related to anatomic landmarks. In a preferred embodiment, the spacings remain relatively the same for patients of all sizes from neonates to obese patients, ranging from 250 g to 400 kg. In another embodiment, the spacings vary based on an algorithm reflecting body size and habitus. Other configurations have the advantage of determining differential motion of one hemithorax vs. the other which is useful in diagnosing or monitoring unilateral or asymmetric pathology such as pneumothorax, hemothorax, empyema, cancer.

Referring now to FIG. 2, there is shown one embodiment with a specific electrode configuration called Posterior Left to Right (PLR), in which the first electrode 7 is placed 6 inches to the left of the spine at the level of the xiphoid process, the second electrode 8 is placed 2 inches to the left of the spine at the level of the xiphoid process, the third electrode 9 is placed 2 inches to the right of the spine at the level of the xiphoid process, and the fourth electrode 10 is placed six inches to the right of the spine level with the xiphoid process. The advantage of placing the electrodes in this configuration is that both lungs are factored into the reading and high level of signal.

Figure 3:
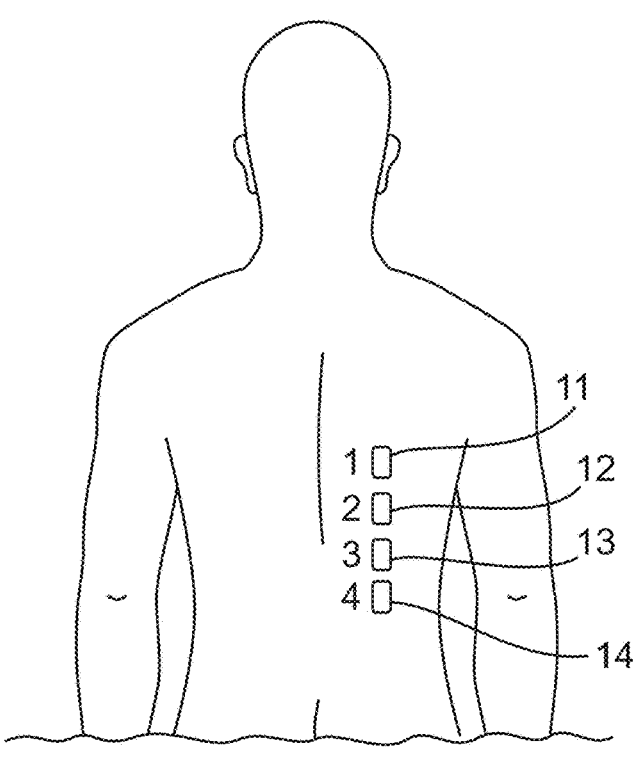
FIG. 3 is a diagram of the Posterior Right Vertical electrode configuration.

Referring to FIG. 3, there is shown the second specific electrode configuration called Posterior Vertical Right (PVR), in which the first electrode 11 is placed midway between the midaxillary line and the spine just beneath the scapula, the second electrode 12 is placed two inches beneath electrode 1, the third 13 electrode is placed two inches beneath electrode 2, and the fourth electrode 14 is placed beneath electrode 3. The advantages of this configuration are the reduction of electrode movement due to thoracic expansion and less cardiac interference. This position has the benefit of little to no volume change between electrodes and less heart noise.

Figure 4:
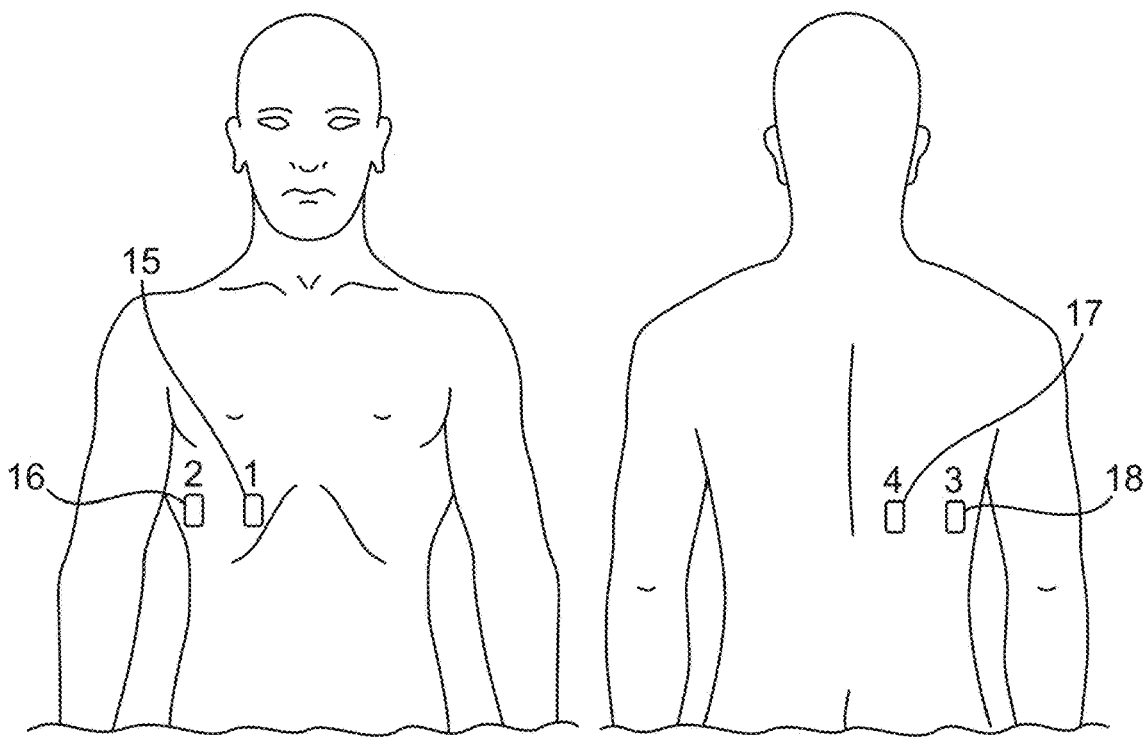
FIG. 4 is a diagram of the Anterior-Posterior electrode configuration.

Referring to FIG. 4, there is shown the third specific electrode configuration called Anterior to Posterior (AP), in which the first electrode 15 is placed 6 inches to the right of the right midaxillary line at the level of the xiphoid process, the second electrode 16 is placed 2 inches to the right of the right midaxillary line at the level of the xiphoid process, the third electrode 17 is placed 2 inches to the left of the right midaxillary line at the level of the xiphoid process, and the fourth electrode 18 is placed 2 inches to the left of the right midaxillary line at the level of the xiphoid process. This position captures the most volume change, which is useful for determination of localization of breathing.

Figure 5:
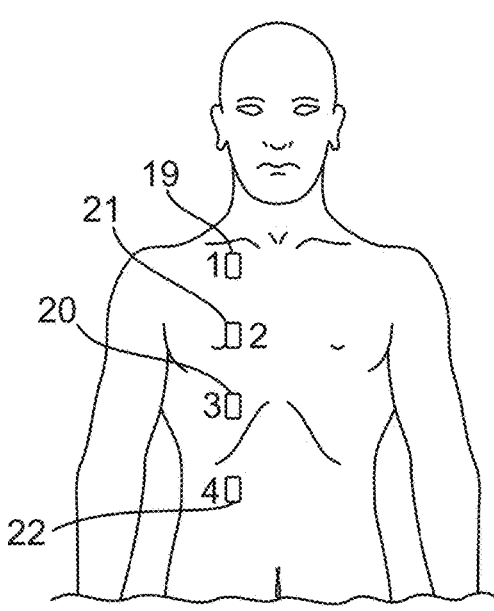
FIG. 5 is a diagram of the Anterior Right Vertical electrode configuration.

Referring to FIG. 5, there is shown the fourth specific electrode placement called Anterior Vertical Right (AVR), in which the first electrode 19 is placed immediately beneath the clavicle midway between the xiphoid and midaxillary line, the third electrode 20 is placed at the level of the xiphoid in line with the first electrode, the second electrode 21 is placed 4 inches above the third electrode, and the fourth electrode 22 is placed 4 inches below the third electrode. This position is useful for neonates and other patients whose characteristics prevent the operator from placing leads on the posterior. Other four-probe positions are placed vertically and horizontally on the abdomen and thorax, equidistant from each other or at specifically measured distances. Probe positions are also placed at physiological landmarks such as the iliac crest or third intercostal space. Probe placement on both the abdomen and thorax allows the relationship between chest and abdominal breathing to be determined. This relationship assists in diagnosis and monitoring of therapeutics.

In addition to the aforementioned four-probe configurations, these configurations can be modified to include more probes by adding probes equidistant between the positions, for example, by adding electrodes in between electrodes 1 and 2, 2 and 3, 3 and 4 in the AP configuration two inches from each electrode in line with the placement. With a large number of electrodes, they can be placed in a grid pattern equidistant from each other; this configuration will be further discussed below. Other placements for 2 or more leads include around the thorax at equidistant points at a constant height such as the xiphoid process. The specific placement for the 24 lead system is within a linear array with 12 leads equally spaced in a linear on the chest and back respectively. Such a grid or array can be implemented within a net or vest to be worn by the patient. In one embodiment, the device provides a table describing lead placement alternatives and provides a measurement device to assist in probe placement. In one embodiment, measured distances between leads are confirmed automatically by the leads which have positioning sensors and/or sensors which can determine distance from one sensor to another sensor or sensors.

Figure 6:
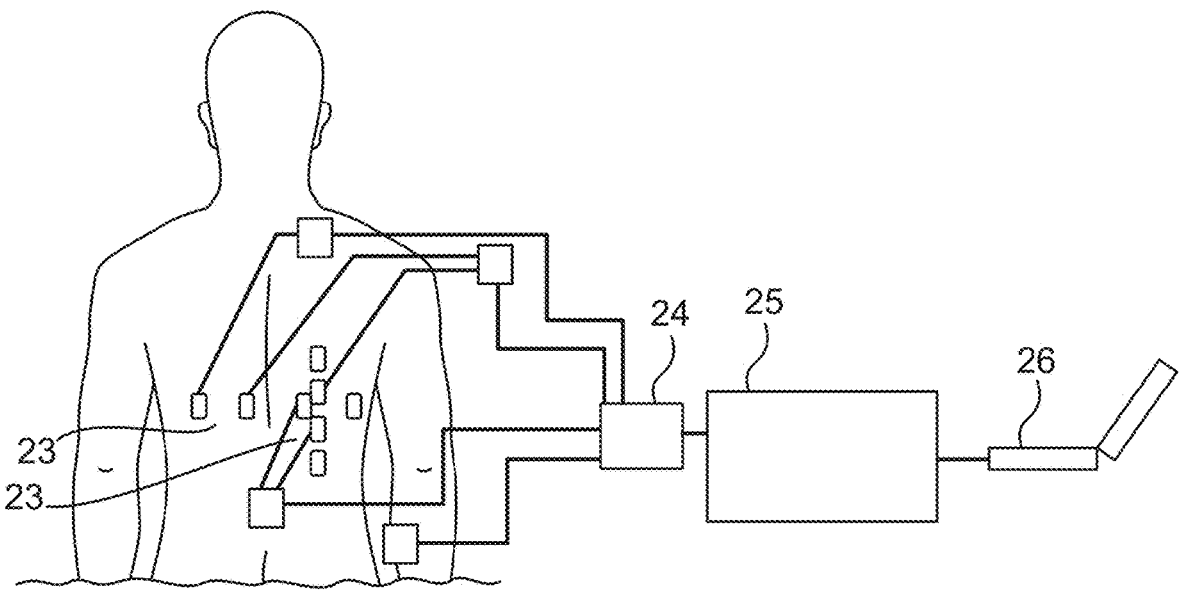
FIG. 6 is a perspective view of two four-lead configurations connected to each other by a multiplexer.

Referring now to FIG. 6, there is shown several electrode configurations 23, connected together by means of an analog multiplexer 24 and connected to a radio frequency impedance meter 25 and a programmable element 26 such as a PC. There is shown an embodiment of the device implementing the lead and multiplexor configurations shown in the previous figures, FIGS. 2 and 3. In FIG. 6, each lead is connected to several different electrodes by means of a multiplexer. The advantage of this configuration is that it allows the device to digitally switch the electronic inputs and outputs of the DAS and effectively switch the electrode configuration in order to gather data on impedance in several directions nearly simultaneously. For example, a 12-electrode system is comprised of four different sets of leads, with the first set going to the corresponding first electrode in each configuration, the second set of leads going to the corresponding second electrode in each configuration, and so forth.

Figure 7:
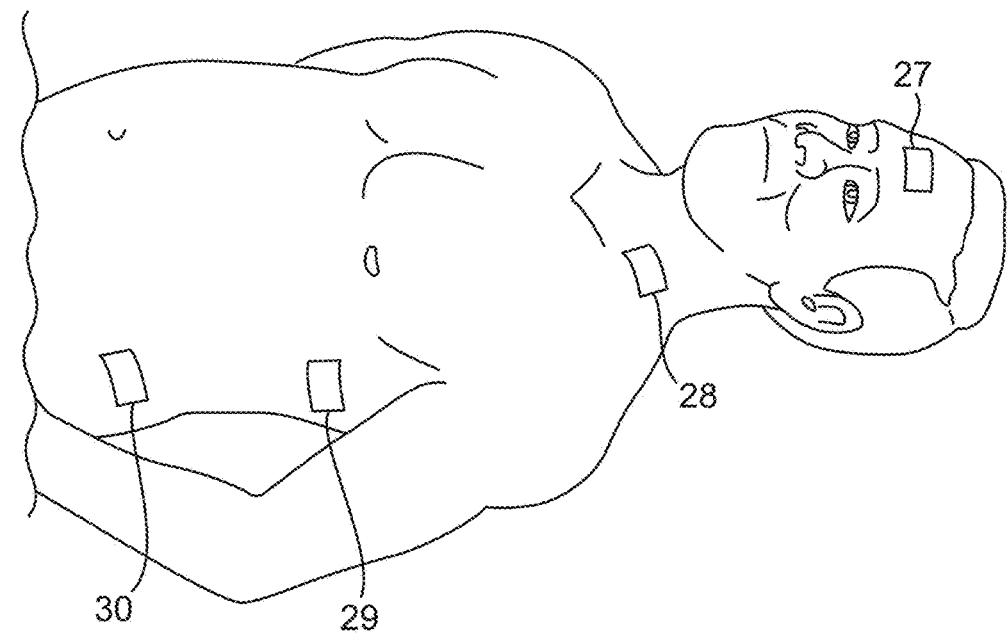
FIG. 7 is a diagram of the ICG electrode configuration.

Electrode configurations are also made to correspond with anatomic positions on the thorax, abdomen, and limbs, such as a resting ICG position shown in FIG. 7 where the first electrode 27 is place on the forehead, the second 28 above the left clavicle, the third 29 on the midaxillary line level with the xiphoid, and the fourth 30 on the midaxillary line immediately above the iliac crest.

Each electrode configuration will be affected by motion in different ways. For instance, movement of the right arm will cause a motion artifact on any lead placement which traces impedance across the right pectoral, latissimus, trapezius muscles, and other muscles of the chest and upper back. By noting differences between the shapes, derivatives or magnitudes of simultaneously recorded signals from different lead placements, local motion artifacts can be identified and subtracted from the impedance signal.

In one embodiment, the probes are manufactured in a linear strip with a delivery and sensor pair at each end and having a fixed distance between the delivery and sensor electrode to form a discrete pad. In a preferred embodiment, there is a compliant strip in-between the two pads that can be stretched to permit appropriate patient specific positioning based on anatomic landmarks. Preferably the material, once stretched, will maintain its extended configuration.

Probes

Figure 23:
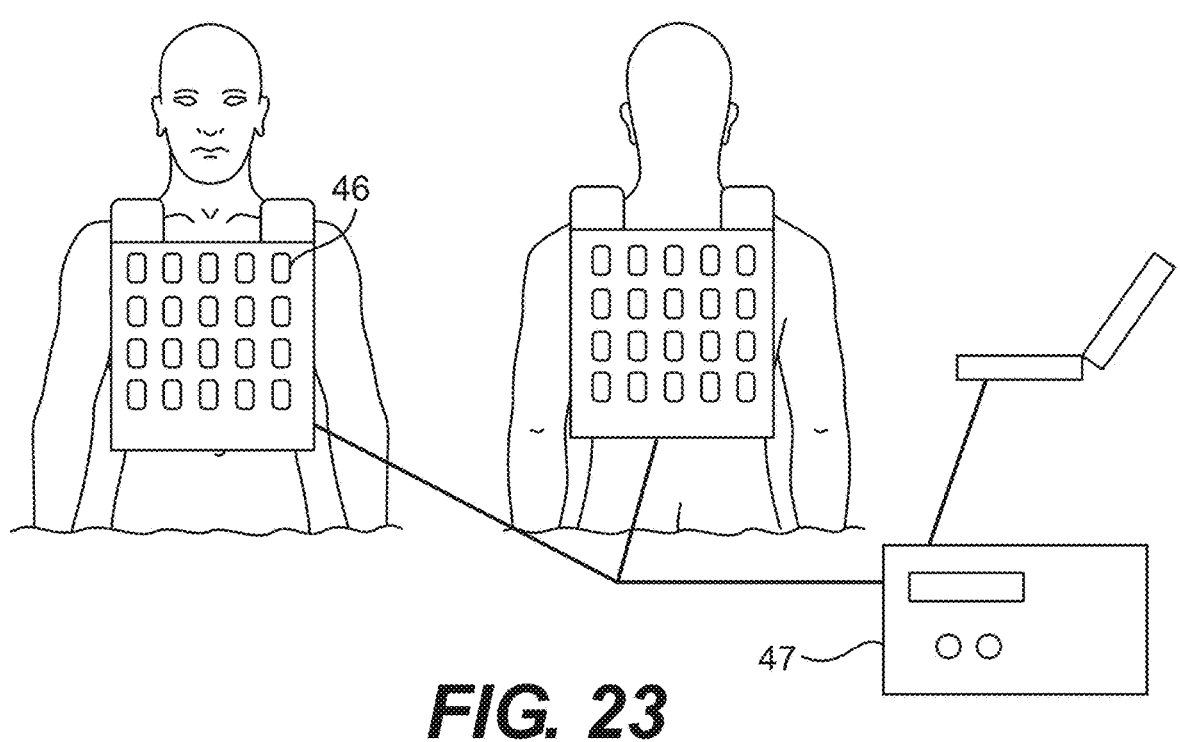
FIG. 23 is a preferred embodiment of the invention that utilizes a vest for the sensors.

Referring now to FIG. 23, there is shown an embodiment of the device in which the one or more remote probes, which are embodied as surface electrodes, speakers and/or microphones, are integrated into a vest 46 connected to an impedance plethysmograph 47 using a cable. The advantage of this embodiment is that the position of leads is determined by the manufacturer of the vest, and thus they are standardized. That is, the use of the vest eliminates operator error with respect to lead configuration. In an alternate embodiment, the probes and actuators are wireless. In an alternate embodiment, the vest also includes leads that cover the abdomen.

Figure 24:
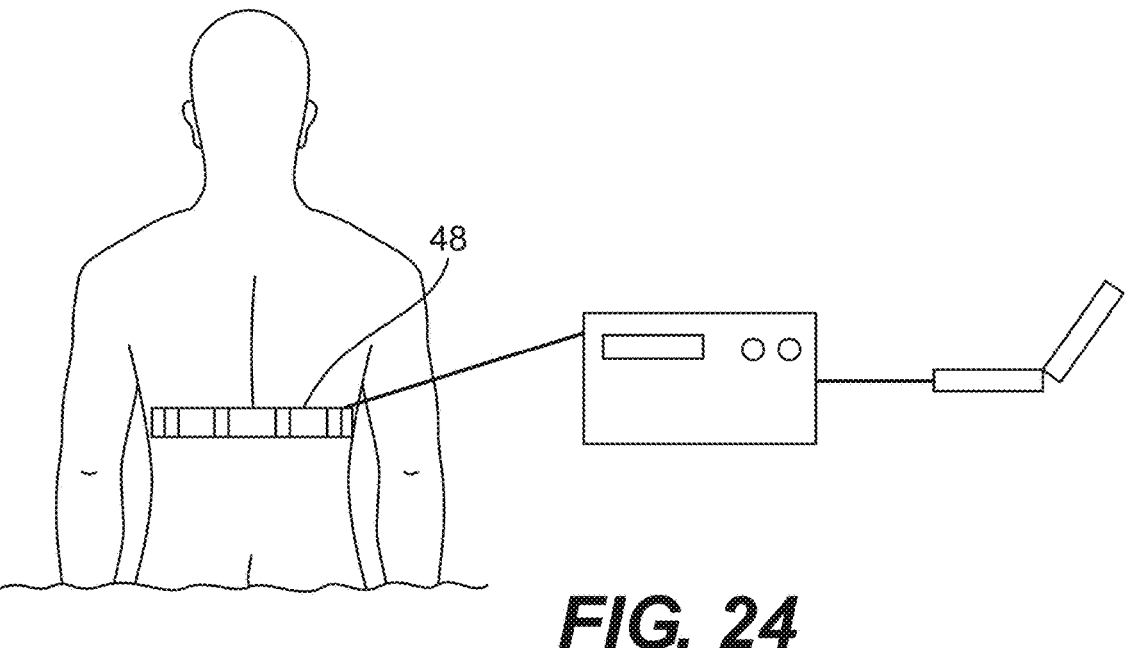
FIG. 24 is a preferred embodiment of the invention that utilizes an array built into a piece of cloth for the sensors.

Referring now to FIG. 24, there is shown an embodiment of the device in which the one or more remote probes are integrated into an array 48 where the electrodes are connected by a compliant piece of cloth or netting which is be pressed gently onto the patient's skin. The benefit of this configuration is that the inter-electrode distance is standardized by the array manufacturer, thus lessening operator dependent error with respect to electrode configuration.

Figure 25:
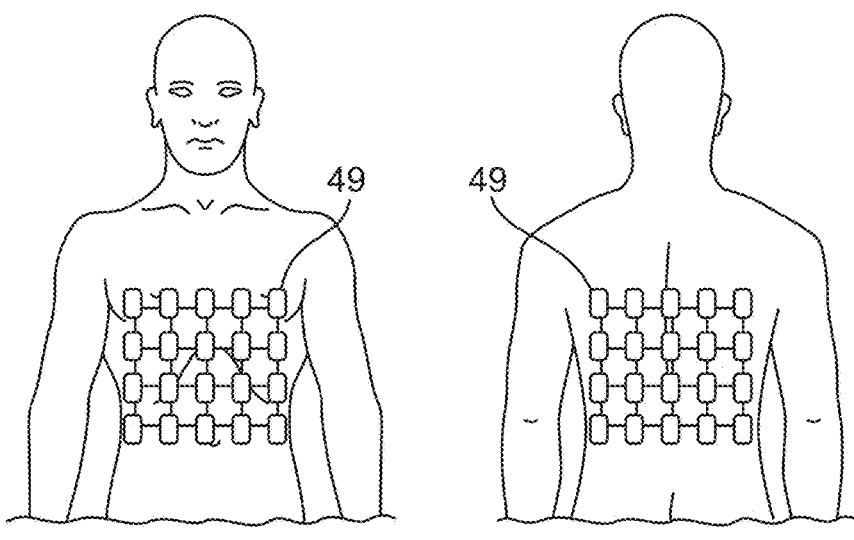
FIG. 25 is a preferred embodiment of the invention that utilizes a net of sensors.

Referring now to FIG. 25, there is shown an embodiment of the device in which the one or more remote probes are connected to each other by strings, forming a net 49 which can be applied to the patient's skin quickly and effectively. The benefit of said embodiment is that the inter-electrode distance as well as the relative positions of electrodes to one another are standardized, thus lessening the effects of operator dependent error. In another embodiment, elastic stretch of the strings provides probe adjustment for different body habitus. Preferably, the stretch material would provide a measurement of the distance either to be read on the material or by relaying information relative to stretch to the device. Preferably, the strings would have attached displacement sensors such as linear displacement transducers or strain gauges functionally connected to the programmable element to relay information about the length each string of the net is stretched. Preferably, the programmable element is further programmed to account for changes in lead placement relayed to it from the displacement sensors.

Figure 26:
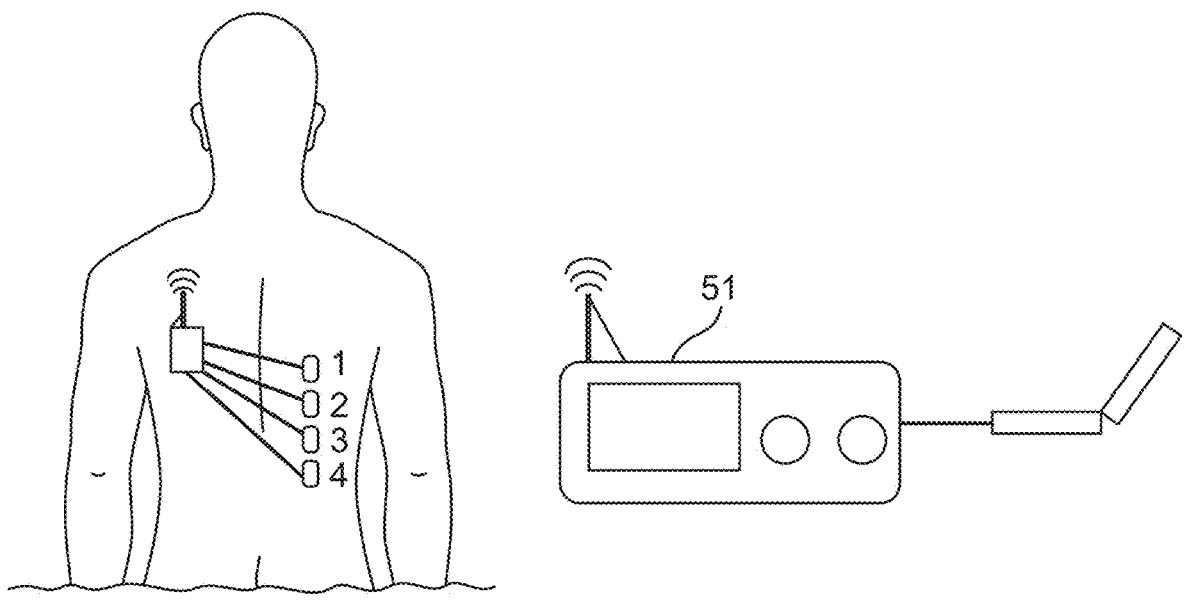
FIG. 26 is a preferred embodiment of the invention that utilizes a wireless transmitter and receiver.

Referring now to FIG. 26, there is shown an embodiment of the device in which the one or more remote probes are functionally connected to a remote transmitter 50, and in which the programmable element 51 is connected to a remote receiver. The communication protocols proposed for the system range from a limited scope to a vastly networked system of several nodes. This provides a foundation for an unlimited number of use cases. In one embodiment of the remote communication protocol a close range high frequency system such as Bluetooth v4.0 is used. This emulates a wireless solution of what a RS-232 wired connection would provide. This enables the communication of two devices in close range quickly and securely. In another embodiment a roughly 802.11 compliant protocol is used to generate a mesh network comprised of the nearest devices. This mesh network incorporates all of the devices in a given unit. The unit size is without bound since the addition of individual nodes increases the range (range and unit size are directly proportional since the network is comprised and governed by the nodes themselves—no underlying infrastructure is required). Only a vast outlier is left out of this network. This means that in order for the outlier to be omitted the nearest currently connected node must be unequivocally out of range for the outlier to communicate with. These services, specifically the hardware, are capable of running/polling without the usage of a main CPU (minimizes battery usage). This is useful because when a device is not being read it can just act as a relay node. The nature of the system minimizes power requirements (increasing longevity of service), supports asymmetric links/paths, and enables each node to play multiple roles in order to benefit the network.

Another embodiment requires connection to a LAN or WAN network, the remote procedure is catalyzed by a user-driven event (button press, etc). This generates a unique identifier, for a digital receipt of the data transaction, on each phone coupled with device specific information. This information is supplemented with a GPS location to distinguish the devices locations. Since the data transmission was initiated by both parties at a precise time, coupled with GPS information, the system is capable of securely identifying both parties by location, UID, and device identifier. All methods are secured with anonymity heuristics and encryption. This will prevent snooping of data, a problem presented by a "man-in-the-middle" attack.

Figure 33:
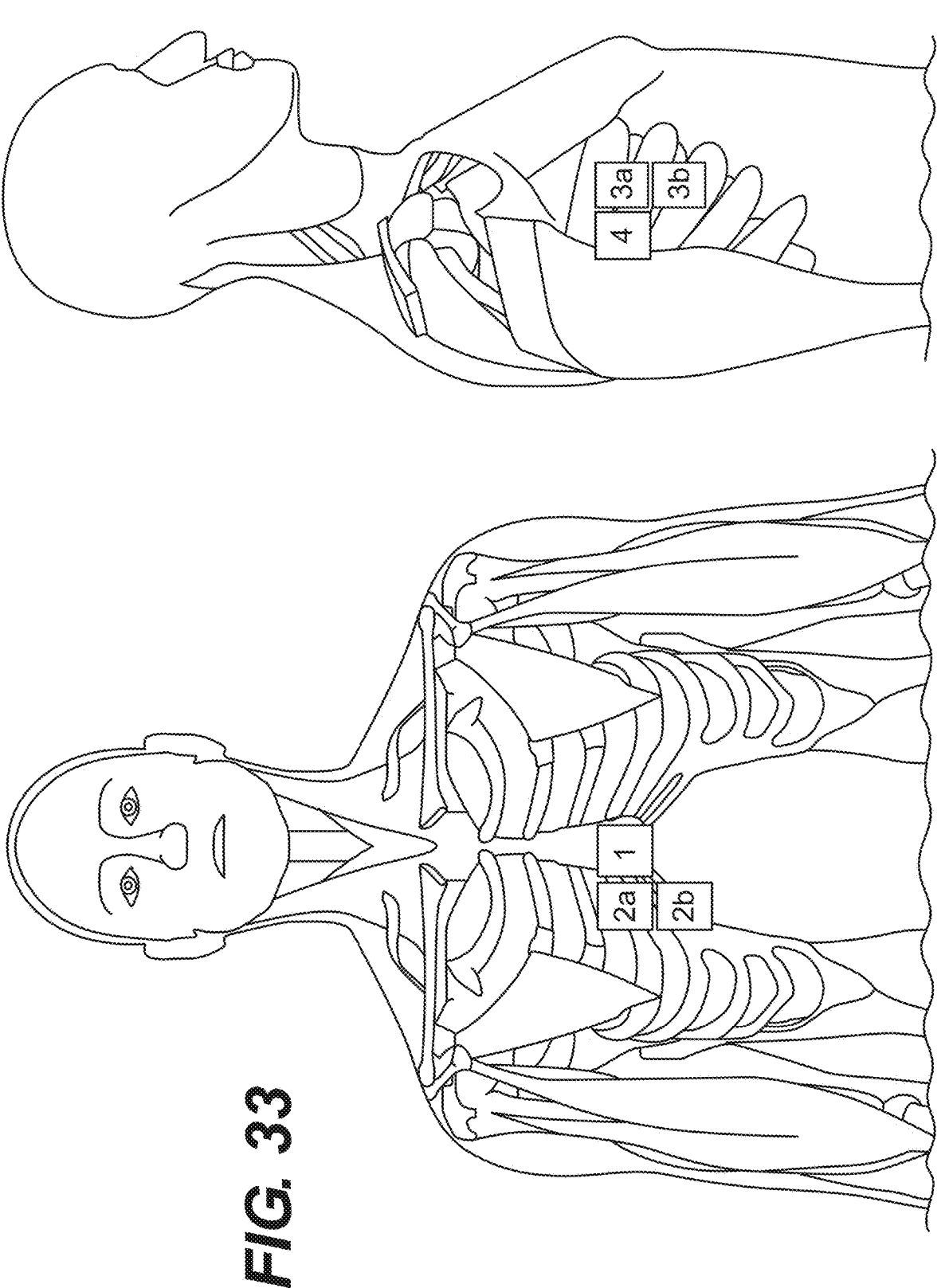
FIGS. 33-38 depict different embodiments of lead placement.

Another embodiment of the device utilizes one or more electrical probes implanted in the body. In one embodiment of the invention, the implanted probes are connected to a cardiac pacemaker. In another embodiment, the implanted probes are connected to an internal automated defibrillator. In another embodiment, the implanted probes are connected to a phrenic nerve stimulator. In another embodiment the implanted probes are connected to a delivery pump for pain medication, local anesthesia, baclofen, or other medication. In another embodiment, the implanted probes are connected to another implanted electronic device. Preferably the connections are wireless. Referring now to FIG. 33, electrode configuration XidMar is show.

Configuration XidMar is a two channel configuration with electrode 1 on the xiphoid process and electrode 4 on the right midaxillary line, horizontally aligned with electrode 1. Electrode 2a is 1 inch to the left of electrode 1, while electrode 3a is 1 inch to the right of electrode 4. Electrodes 2a and 3a are used to record the voltage signal on channel a. Channel b is recorded using electrodes 2b and 3b which are found 1 inch below the corresponding channel a electrodes.

Figure 34:
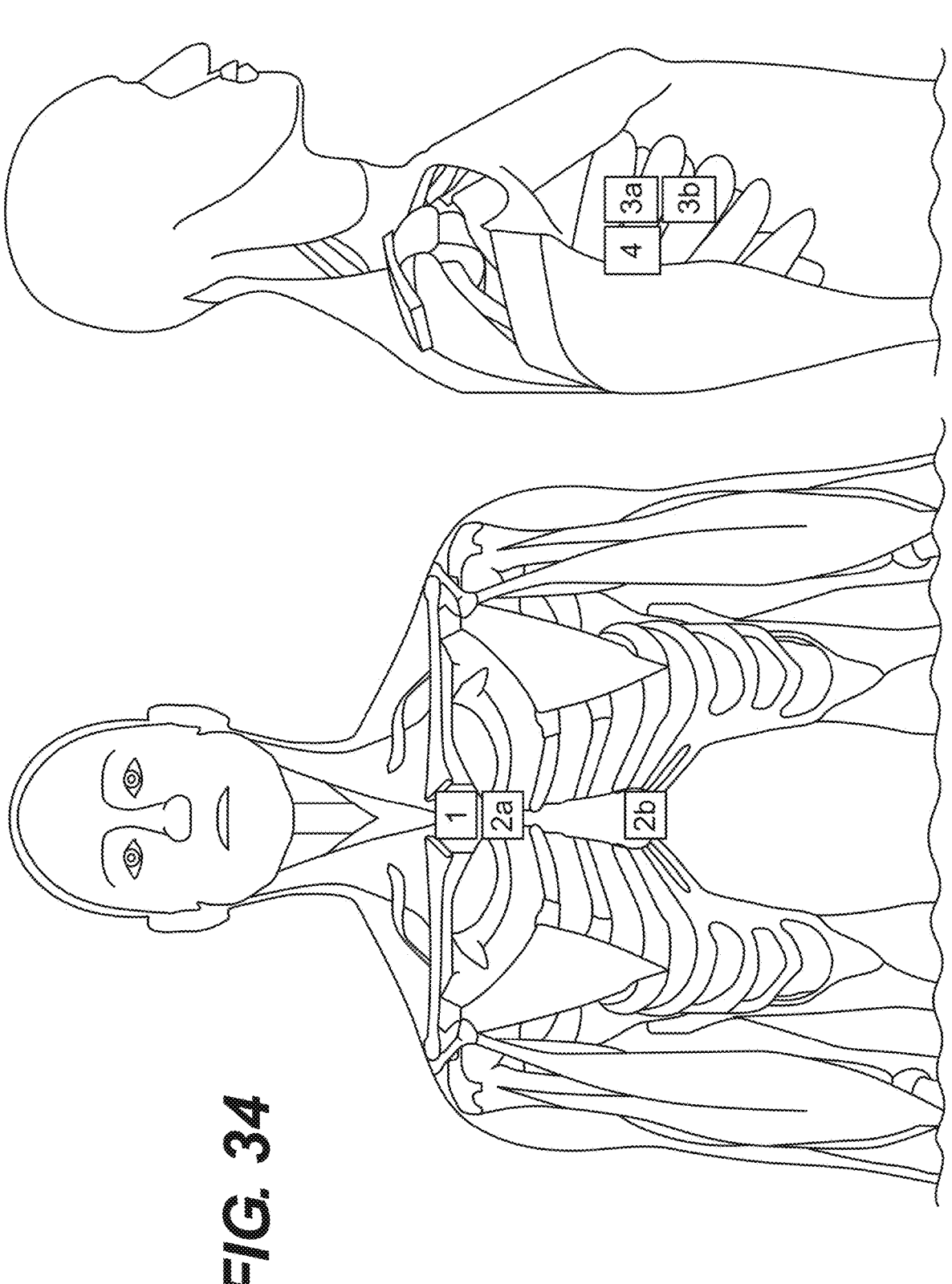

FIG. 34 shows the StnMar electrode configuration in which electrode 1 is located just below the sternal notch and electrode 4 is located on the right midaxillary line, horizontally aligned with the xiphoid process. Electrode 2a is located 1 inch below electrode 1, and electrode 3a is located 1 inch to the right of electrode 4. Channel b is at an angle approximately 45 degrees to channel a. Electrode 2b is located on the xiphoid process and electrode 3b is located 1 inch below electrode 3a.

Figure 35:
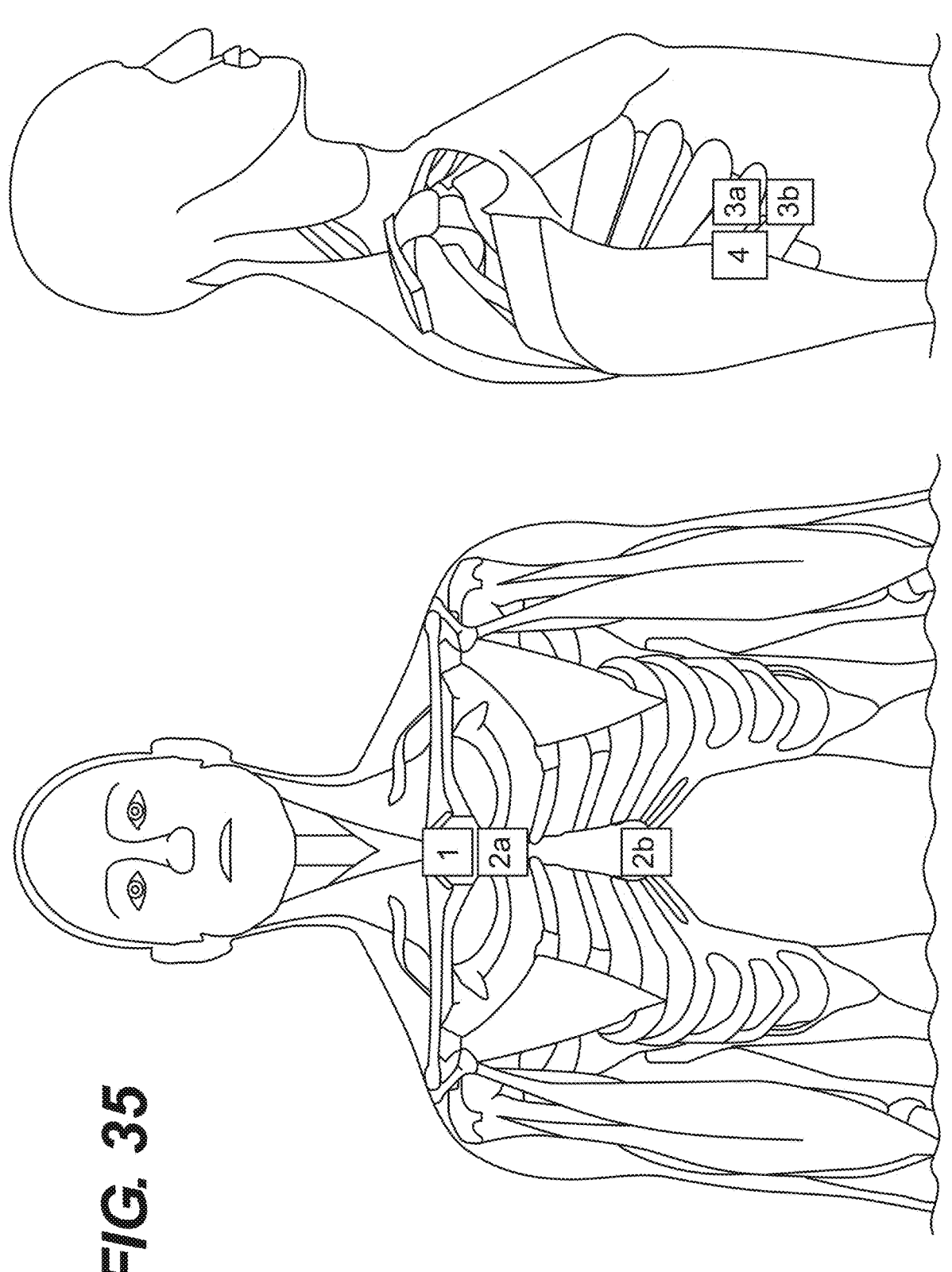

FIG. 35 shows the StnIMar electrode location in which electrode 1 is located just below the sternal notch and electrode 4 is located on the inferior right midaxillary line at the bottom of the rib cage. Electrode 2a is located 1 inch below electrode 1, and 3a is located 1 inch to the right of 4. Electrode 2b is located on the xiphoid process and electrode 3b is located 1 inch below electrode 3a.

Figure 36:

FIG. 36 shows the McrMar electrode configuration in which electrode 1 is located on the right midclavicular line just below the clavicle and electrode 4 is located on the right midaxillary line horizontally aligned with the xiphoid process. Electrode 2a is located 1 inch below electrode 1 and electrode 3a is located 1 inch to the right of electrode 4. Electrode 2b is located on the xiphoid process, and electrode 3b is located 1 inch below electrode 3a.

Figure 37:

FIG. 37 shows the McrIMar electrode configuration in which electrode 1 is located on the right midclavicular line just below the clavicle and electrode 4 is located on the inferior midaxillary line approximately at the bottom of the ribcage. Electrode 2a is located 1 inch below electrode 1 and electrode 3a is located 1 inch to the right of electrode 4. Electrode 2b is located on the xiphoid process and electrode 3b is located 1 inch below electrode 3a.

Figure 38:
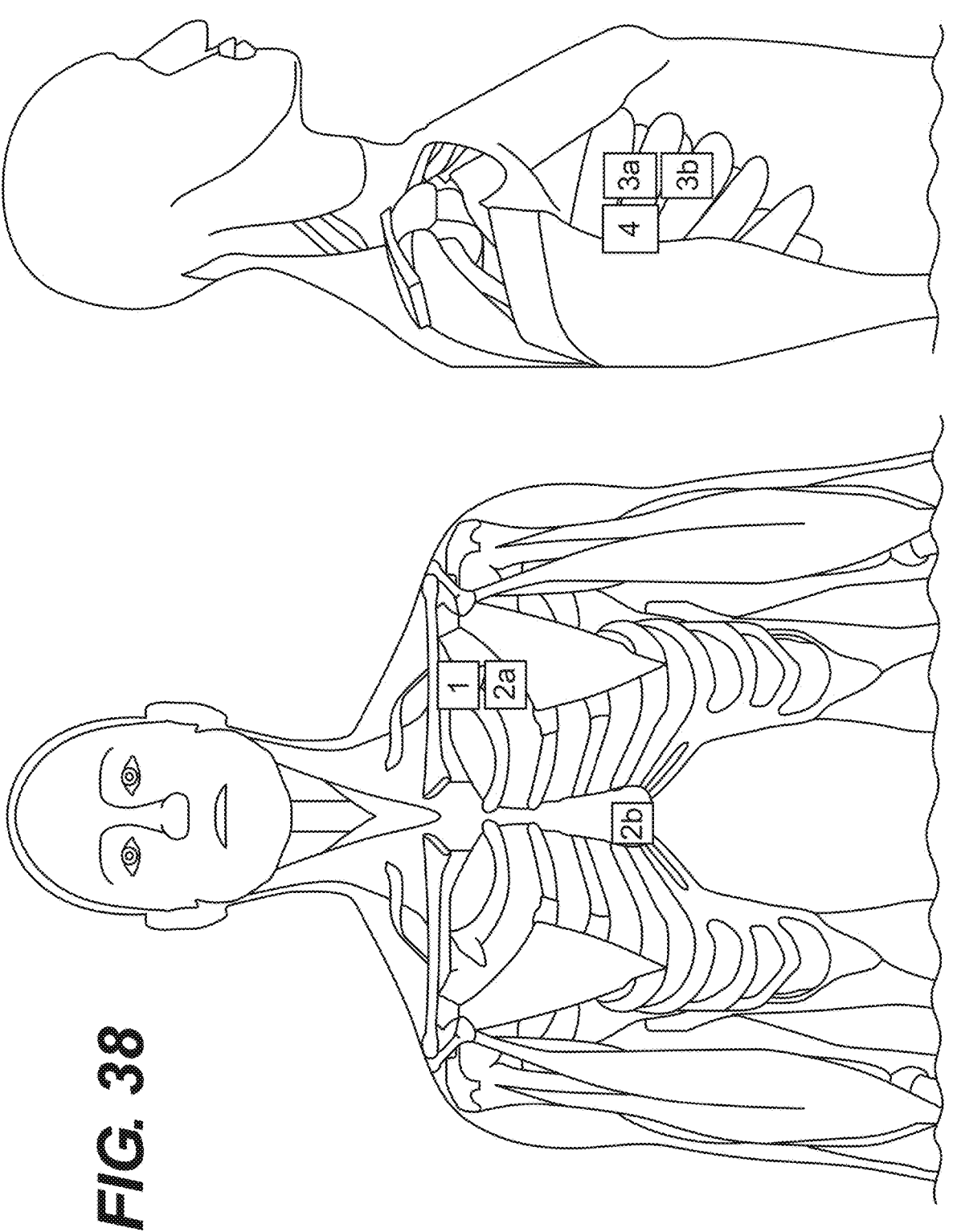

FIG. 38 shows the McIMar electrode configuration in which electrode 1 is located on the left mixclavicular line just below the clavicle and electrode 4 is located on the right midaxillary line, horizontally aligned with the xiphoid process. Electrode 2a is located 1 inch below electrode 1 and electrode 3a is located 1 inch to the right of electrode 4. Electrode 2b is located on the xiphoid process and electrode 3b is located 1 inch below electrode 3a.

The electrode configurations shown in FIGS. 34-38 can utilize either channel a, channel b, or both simultaneously to measure data.

In one embodiment of the invention, the system is adapted to perform an impedance tomography scan utilizing a one or more pairs of source electrodes and one or more voltage sensing electrodes. The scan is completed by taking a series of measurements with a movable electrode which is applied to the skin. The movable electrode forms a voltage measuring pair for impedance reading with at least one other electrode. The movable electrode may be coated in hydrogel which may be applied multiple times. In another embodiment of the invention, the electrode contains a hydrogel dispenser for each application. In this embodiment, hydrogel is stored in an internal pouch or syringe and there are devices, such as a mechanical button or squeeze tube, which allows the user to dispense hydrogel onto the electrode. In one embodiment of the device of the invention, the system directs the user to sweep the movable electrode between predetermined points on the body as indicated on the user interface or on a reference card. In another embodiment, the user may place the movable electrode from point to point and the system senses the location of the electrode using a camera, sonar, radar or other device.

The secure adhesion of electrodes is determines the quality of impedance readings. In one embodiment of the invention, the system detects the quality of adhesion and reports an index of adhesion to the user. In another embodiment, the system reports problems with adhesion if the index crosses a specific threshold. In a preferred embodiment of the invention, there are multiple voltage sensing channels arranged in a straight line. This can be accomplished using five electrodes arranged in a line. Referring to the five electrodes by letter, electrodes A and B are placed close together on one end of the line, electrodes D and E are placed close together on the other end of the line. Pair A-B and pair D-E may be placed 3-24" apart from each other. Electrode C is placed somewhere between the two pairs. Impedance is measured on three channels, B-C, C-D and B-D. If all the electrodes are adhered well, the sum of $Z_{BC}$ and $Z_{CD}$ should be close to $Z_{BD}$. The difference between the measures, or the ratio of the difference to the full measurement can be used to determine the index of adhesion quality.

In one embodiment of the invention, Electrode C is not placed in a straight line with the other pairs of electrodes. In this case, impedance is measured on channels B-C and B-D. The ratio between the impedance on the two channels $Z_{BC}$ and $Z_{BD}$ is used to determine the index of adhesion quality. In another embodiment of the invention, the current driven through electrodes A and E is measured. The current measurement or variability in the current measurement can be used to determine the index of adhesion for electrodes A and E.

Figure 39:
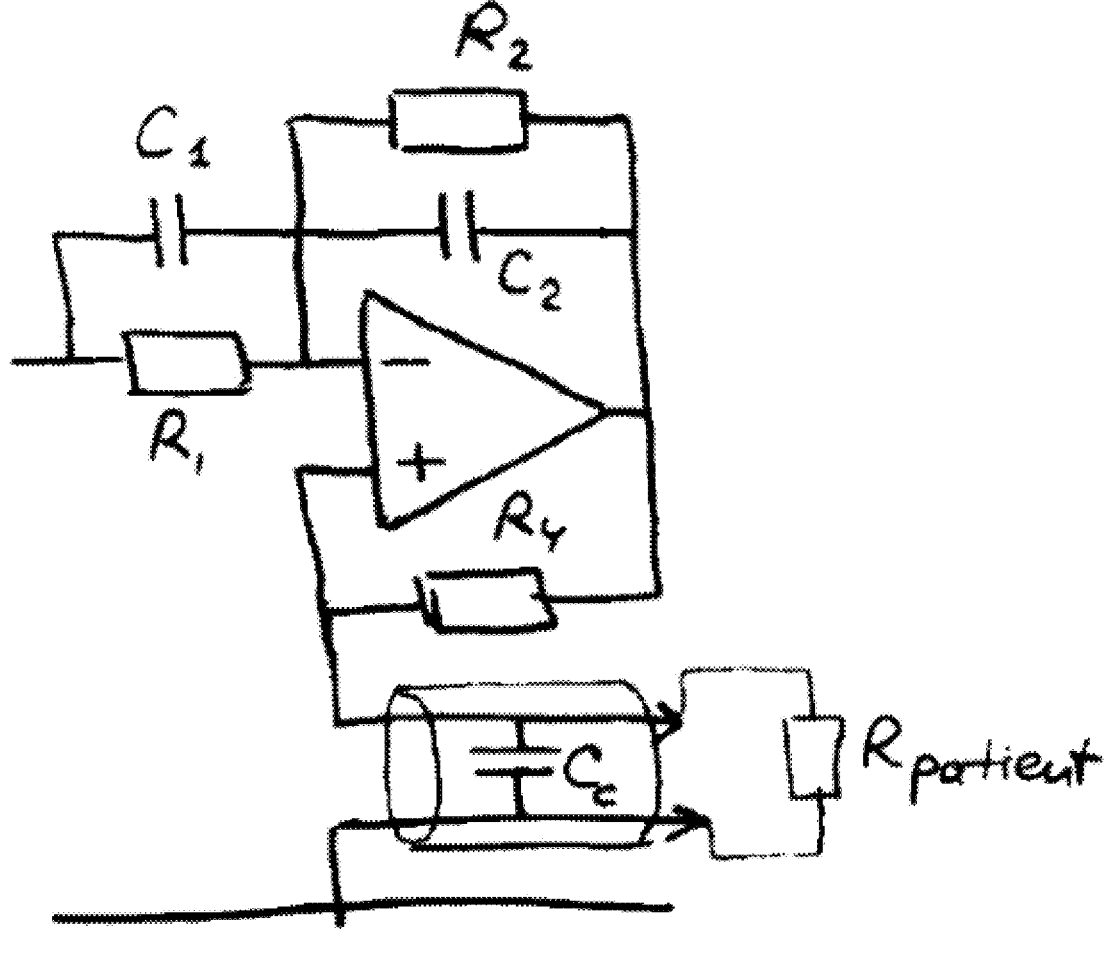
FIG. 39 depicts an embodiment of a modified Howland circuit for compensating for parasitic capacitances.

Electrical connectors have inherent capacitance which can affect impedance measurements. In one embodiment of the invention, the system compensates for the capacitance of cables, leads or other electrical connection between the impedance measuring subsystem and the patient-connected electrodes. In one embodiment, this is accomplished by an inductor within the impedance measuring subsystem. In another embodiment, a compensating inductor is integrated into a patient cable or leads which connect the impedance measuring subsystem to the patient-connected electrode pads. In another embodiment a compensating inductor is embedded into an integrated electrode PadSet. In another embodiment, a modification of a Howland circuit which consists of capacitors $C_1$ and $C_2$ with values chosen to compensate for parasitic capacitances Cc is used (see FIG. 39).

To achieve high clinical relevancy and good definition of respiratory curves, the impedance measurement subsystem should to be able to determine small variations in patient impedances on top of a relatively high baseline background with a high resolution. Therefore, there are stringent requirements on the absolute and relative impedance measurement errors. To obtain sufficient precision one or more of the following design solutions can be used: (1) the electronic design can be based on high precision/low temperature drift electronic components; (2) a high precision analog divider can be used to obtain the ratio between measured voltage and monitored source current, compensating for variations in the source current; (3) the same voltage can be used for source current generation and as an ADC reference, compensating for variations in the reference voltage; (4) external calibrated impedance standards can be used to calibrate and verify the impedance measurement subsystem performance. The calibrated system is preferably connected to the impedance standard with the same trunk cables used for patient measurements, providing verification of overall system performance. (5) The impedance measuring subsystem can have a built-in calibrated impedance standard, allowing on-site verification and recalibration. In one embodiment built-in standard is attached to the system via an external service port. The calibration is conducted by connecting the "patient" end of trunk cable back to the service port on the device and running calibration procedure available through the device's GUI. (6) The calibration can be completed by varying impedance of the built-in standard over the whole range of the measured patient impedances to derive a device model, which can be used during patient measurements to achieve high-precision results. (6) The temperature model of the device can be derived by placing the device into a thermostat and measuring drift in the measured value as a function of internal device temperature. The internal device temperature can be monitored via a built-in thermal sensor. During patient measurement, a measurement correction is calculated using the thermal sensor's reading and applied to the measured values.

Active Acoustic System

For acoustic measurement of lung volumes, preferably the device comprises at least one speaker and at least one microphone. Preferably the at least one speaker and microphone are arranged as a net, vest, or array. Preferably the at least one speaker switches between discrete frequencies or broadcasts broad spectrum noise. Preferably, numerous speakers are active simultaneously, broadcasting different acoustic signals. Preferably, numerous microphones are active simultaneously and record the measured acoustic properties of the thorax which can be correlated to lung volume as well pathologies of the lungs. Preferably, the microphones also record sounds that originate in the lungs such as wheezing, squawks, and crackles, which can be indicators of numerous chronic and acute pulmonary diseases. Preferably the lung sounds are recorded and identified as they are modified by the active signal. Preferably an algorithm analyzes the number and position of wheezes, squawks, and crackles to predict asthma and other pulmonary diseases. In one embodiment, acoustic data are combined with impedance data to help time the acoustic measurements relative to the respiratory cycle. In one embodiment acoustic data are combined with impedance data for the purposes of diagnosis or monitoring of disease. An example of this is congestive heart failure where stiffness creates characteristic changes in impedance curves and there are also changes in lung sounds associated with congestive heart failure. Combination of the data provides additional information.

Figure 20:
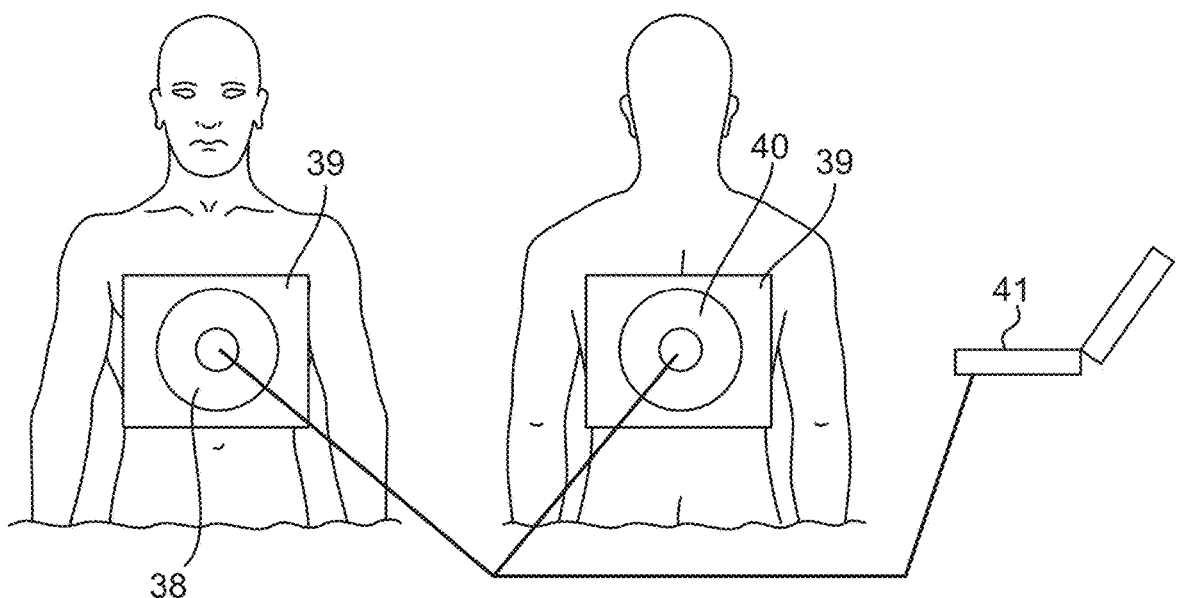
FIG. 20 is a preferred embodiment of the invention that utilizes a speaker and a microphone.

Referring now to FIG. 20, there is shown a device in which a speaker 38 is attached to the chest of a patient, and insulated with sound dampening foam 39. A microphone 40 is attached to the patient's back and is insulated with sound dampening foam. Both the speaker and the microphone are functionally connected to a programmable element 41, for example a computer with installed analysis software such as MATLAB. The output element provides data relating to the patient's respiration to the operator in real time. The speaker generates an acoustic signal which is recorded by the microphone. Signal generation and recording are timed and synchronized by the programmable element. Analysis software uses features of the recorded sound wave to evaluate the acoustic properties of the thorax, which can be used to estimate lung volume. Said signal features include but are not limited to: frequency-dependent phase shift, and amplitude attenuation. Preferably, the speaker switches between discrete frequencies of sound or generates broad spectrum white noise.

In another embodiment of the device, the microphone is also used to detect sounds which originate within the lungs such as crackles, squawks and wheezes. In one embodiment, the programmable element of the device will employ software algorithms to detect associate acoustic patterns and inform physicians. In one embodiment, the acoustic system will interface with an impedance based system as well.

Figure 21:
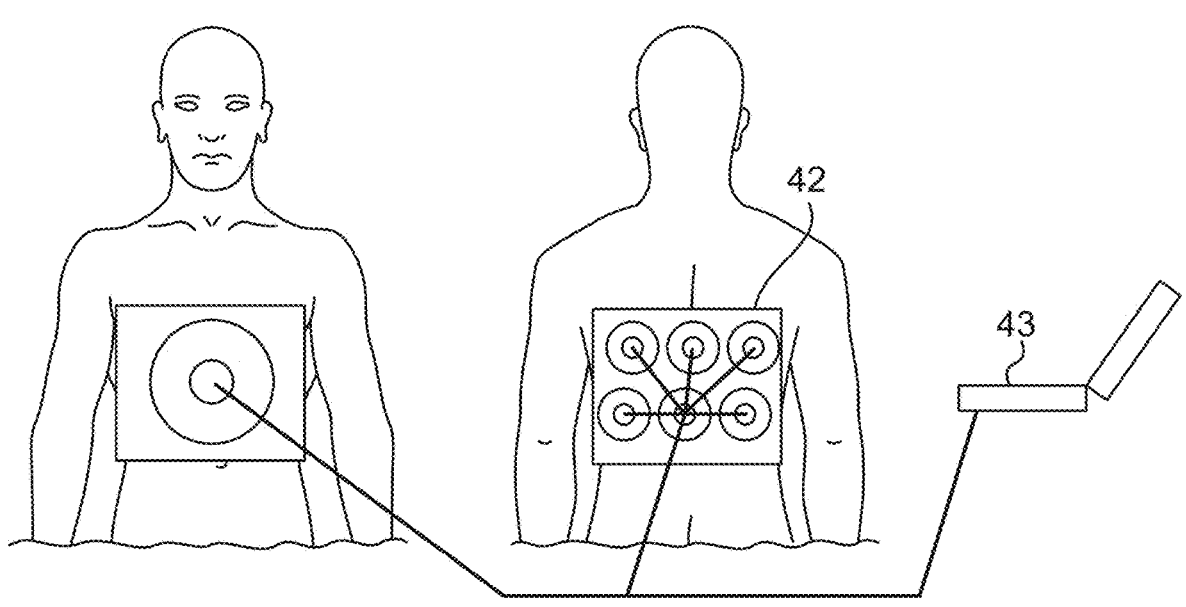
FIG. 21 is a preferred embodiment of the invention that utilizes a speaker and an array of microphones.

Referring now to FIG. 21, there is shown an embodiment of the device in which an array of microphones 42 is used to record transmitted sound from different regions of the thorax. Preferably microphones record simultaneously. Preferably, the programmable element 43 selects the microphone with the best signal to noise ratio for analysis. Preferably, the programmable element combines the data from different channels in order to maximize the accuracy of lung volume estimates and localize pathologies of the lungs including tumor formation, bleeding, and tissue degradation.

Figure 22:
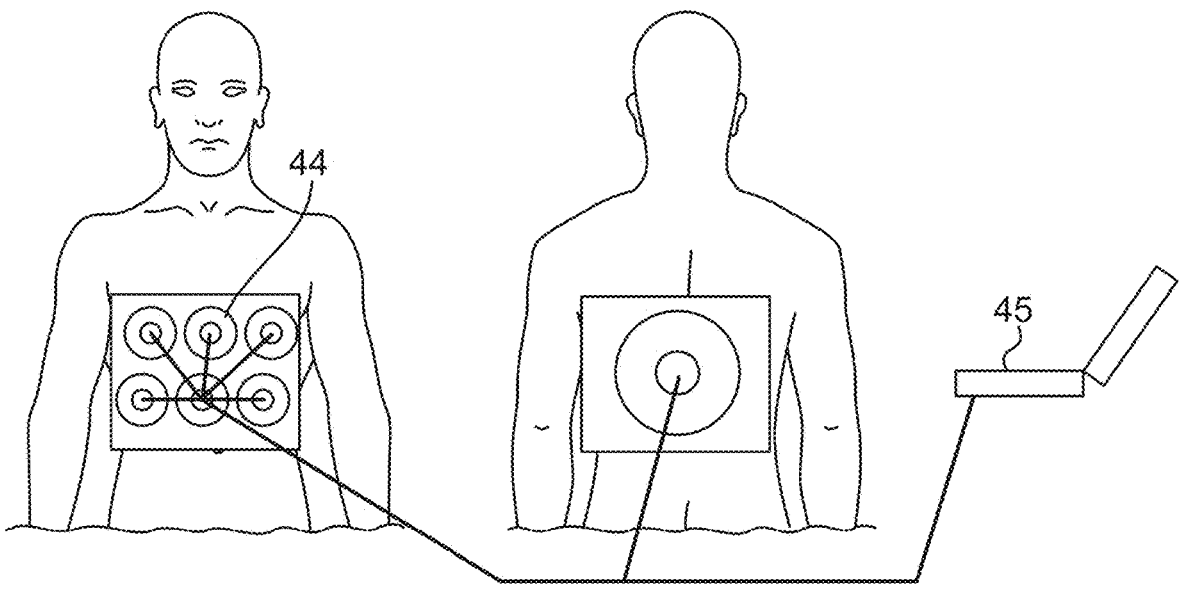
FIG. 22 is a preferred embodiment of the invention that utilizes an array of speakers and a microphone.

Referring now to FIG. 22, there is shown an embodiment of the device in which an array of speakers 44 is used to generate acoustic waves. Preferably the programmable element 45 controls each of the speakers individually, and switches between speakers to allow the device to measure acoustic properties of the thorax in many different directions. Preferably, the programmable element will activate each speaker simultaneously with signals of unique frequencies so that the signal from each speaker can be separated in the recorded signals. Preferably, the programmable element combines the data from different channels in order to maximize the accuracy of lung volume estimates and localize pathologies of the lungs including tumor formation, bleeding, and tissue degradation.

Patient Data Entry

Preferably, the device software maintains a user-friendly GUI (Graphical User Interface). Preferably, the GUI contains a color coding system to aid operators in quickly making diagnoses and decisions for patient care. In one embodiment, the GUI presents a numerical RVM measurement. In one embodiment the GUI presents a respiratory sufficiency index (RSI). In one embodiment, the GUI presents a respiratory waveform.

In the software present in all embodiments of the device, patient data is preferably recorded by the user prior to testing. The user is prompted to enter patient data. The data recorded includes any or all of the following: patient height, weight, chest circumference during maximum inspiration, chest circumference during normal end-expiration, age, gender, ethnicity, and smoking history. In one embodiment, posture when testing is also input into the device within the programmable GUI. Variations in posture may lead to different breathing patterns and tidal volumes. The device accepts posture inputs such as supine and seated and standing. The ability to test patients in multiple postures is helpful with noncompliant patients such as neonates or obtunded patients.

In one embodiment, the device calculates BMI. In a preferred embodiment, an algorithm in the device or on a look up table calculates a "calibration coefficient" that corrects for patient size and body habitus to provide a universal calibration to deliver an absolute measurement. The calibration coefficient may be obtained by combining patient information with the data recorded off the probes applied. Preferably, the physical location of the probes is also entered. During the data acquisition, the calibration algorithm may validate the data and their consistency with the patient information entered, and may suggest combination of the input parameters that is most consistent with the data recorded, as well as a suggestion for the operator to re-check the patient's information. As data is being acquired, the calibration algorithm may suggest and/or perform readjustment based on signal pattern recorded off probes, and/or provided by an operator as normal or abnormal. In another embodiment, the device calculates BSA or another index of body shape or size. In one embodiment, the system displays predictive values for patient results based on the aforementioned patient data. In one embodiment, the device also provides a percentage comparison against these values within displayed results to further inform the clinician of patient parameters or condition based on standard tables of spirometric data created by Knudsen, Crapo, or others. In one embodiment, the patient's demographics and/or body measurements are entered and the device suggests the lead configuration and/or the spacing of the leads and/or the size or characteristics of the lead for that patient.

In one embodiment, the device assesses signal variation and adjusts display parameters, calibration parameters and or intermediate calculations in response to the variation. In one embodiment the device assesses variation in one or more features of the signal including baseline, mean, minimum, maximum, dynamic range, amplitude, rate, depth, or second or third order derivatives of any items in the list.

In one embodiment, the device calculates a calibration coefficient to convert a raw or processed impedance trace to a respiratory volume trace. In one embodiment, the calibration coefficient is calculated from a range of physiological and demographic parameters. In one embodiment, the device of the invention automatically adjusts the calibration coefficient in response to variation in the parameters. In one embodiment, the device automatically adjusts the calibration coefficient in response to one or more of: respiratory rate, baseline impedance, or mean impedance.

In one embodiment, the device includes one or more of, respiratory rate, baseline impedance, or mean impedance in the calculation of the coefficient, or a correction factor for the calibration coefficient. In embodiments in which the calibration coefficient is based on a time-variable parameter, such as respiratory rate, baseline impedance or mean impedance, the device automatically adjusts the calibration coefficient to account for the variation in the parameter.

In one embodiment, the device adjusts the calibration coefficient based on the assessment of variation in the signal. In one embodiment where the calibration coefficient is used to convert a raw impedance signal to a respiratory volume trace, the calibration coefficient is based partially on respiratory rate.

In one embodiment, the device adjusts the display of a dataset in response to variation in the dataset. The dataset is made up of a raw signal from a sensor, a processed signal from a sensor, or the calculated metrics or parameters.

In one embodiment, the device adjusts the minimum of the y-axis on a displayed chart in response to variation in the dataset. In one embodiment, the minimum of the y-axis on a displayed chart is equal to the minimum of the dataset. In one embodiment the minimum of the y-axis on the displayed chart is equal to the minimum of the dataset within a specific window. In one embodiment, the window over which the relevant minimum of the dataset is calculated is the same as the window over which the data is displayed. In one embodiment, the minimum of the y-axis on the displayed chart is equal to the minimum of the dataset within the display window minus a coefficient or percentage of the minimum value.

In one embodiment, the device adjusts the range of the y-axis of the displayed dataset is to account for variation in the dataset. In one embodiment the range of the y-axis of a displayed dataset is equal to the dynamic range of the dataset. In one embodiment the range of the y-axis of the displayed dataset is equal to the dynamic range of the dataset within a specific window. In one embodiment, the y-axis of the displayed dataset is equal to the dynamic range of the dataset within a specific window, plus a constant, or a percentage of the dynamic range.

In one embodiment, the device adjusts the range of the y-axis of a displayed dataset based on statistics of a feature of the dataset. In one embodiment, the device sets the range of the y-axis to be equal to the mean amplitude of the signal plus the standard deviation of the amplitude of the signal within a specified window multiplied by a coefficient. In one embodiment, the device adjusts the range of the y-axis of a displayed dataset to be equal to the mean amplitude of the signal plus the variance of the amplitude of the signal within a specified window multiplied by a coefficient. In one embodiment, the device calculates the amplitude of respirations in the dataset. The device then removes outliers at the high end, low end or which have features which appear unrelated to the intended measured parameter. The device then adjusts the range of the y-axis to be equal to the mean of the amplitude of the dataset plus the standard deviation of the dataset multiplied by a coefficient.

In one embodiment, the device automatically adjusts the midpoint of the y-axis of a chart of a dataset in response to variation in the dataset. In one embodiment, the device sets the y-axis to be equal to the mean of the dataset within a specific window. In another embodiment, the device sets the y-axis to the equal to the median of the dataset within a specific window. In one embodiment, the device sets the midpoint of the y-axis to the result of a function of the statistics of the dataset.

Calibration Method

The calibration coefficient is calculated in a novel way. In the preferred embodiment, the device contains circuitry and software that automatically calibrates the device. In one embodiment, calibration is aided by data acquired through bioelectrical impedance analysis, a process which measures tissue impedance on one or more channels at various frequencies. In this embodiment, data from bioelectrical impedance analysis may be used to calculate certain characteristics of the subject including, but not limited to, hydration level, baseline impedance and body composition. A low level of hydration causes the electrical impedance of the body to be greater. A high level of fat in the body would also cause an increase in the average electrical impedance of the body, but likely a decrease in overall impedance as electricity passes through the path of least resistance. Muscle is much more vascular than fat and contains more conductive electrolytes, so a muscular patient's body would have much lower electrical impedance than a similarly size person who was not very muscular. Scaling the calibration factor based on these inputs makes it more accurate.

Calibration of the device of the invention preferably comprises predictions for respiratory rate, tidal volume and minute ventilation based on the metabolic requirements of body tissue. Predictions preferably involve multiplying the patient's measured body weight, or ideal body weight by a volume of air, or volume of air per minute required by a unit of body weight. The ideal body weight is determined from a patient's height, race, and/or age and may further be determined with one or more of the Devine, Robinson, Hamwi, and Miller formulas.

In one embodiment, the calibration coefficient is calculated from a patient's demographic information, including but not limited to: sex, age, and race. In another embodiment, the calibration coefficient is calculated from a patient's physiological measurements including but not limited to body type, height, weight, chest circumference measured at different points of the respiratory cycle, body fat percent, body surface area, and body mass index. In another embodiment the calibration coefficient is calculated based on the measured value of the ECG signal recorded at different points. In more detail, the ECG is recorded by electrodes at various locations on the thorax and abdomen. In one embodiment, the differential voltage recordings at different electrodes are used to calculate the average baseline impedance and estimate the resistivity of the patient's thorax in various directions. In another embodiment the calibration coefficient is calculated based on the patient's baseline impedance to an external current source as measured between electrodes in a bipolar configuration, tetrapolar configuration or other configuration comprising 2 or more leads. The locations of these electrodes are placed in a range of configurations over the whole body. In another embodiment, demographic characteristics are combined with baseline impedance measurements for calibration. In another embodiment anatomic information is combined with baseline impedance measurements for calibration. In a preferred embodiment, known volumes recorded on a spirometer or ventilator are combined with demographic information and baseline impedance. In such embodiments, the system may simultaneously measure impedance and volume (using a spirometer, ventilator, or other similar device). The system then computes a specific transformation between impedance and volume as an input to the conversion algorithm In another embodiment, a dynamic calibration based on additional parameters obtained using the impedance measuring subsystem and consisting of overall patient impedance (including skin and fat layer impedances), internal organs impedance (baseline impedance) and its variations, and the shape of the respiratory curve is implemented.

Ongoing or intermittent checks of calibration are preferably undertaken. In a preferred embodiment of the device, calibration is recalculated with the recording of each sample. In another embodiment, the device is regularly recalibrated based on a timer function. In another embodiment, the device is recalibrated whenever the baseline impedance varies from the baseline by a certain threshold such as 10%. In another embodiment, the device is recalibrated whenever tidal volume or minute volume varies from baseline levels or predicted levels by a certain threshold, such as 20%, where predicted values are calculated using the formulas published by Krappo, Knudson, and others.

Ongoing or intermittent checks of calibration may be undertaken. Preferably this involves an internal check to internal phantom.

Preferably ongoing or intermittent checks of baseline impedance are be used to recalibrate or reaffirm calibration. Preferably ongoing or intermittent readings from each hemithorax individually or in combination are used to recalibrate or provide data for recalibration.

Preferably, recalibration is performed automatically or by alerting a caregiver of required modification or requiring additional steps to be taken by the caregiver, such as recalibrating with a ventilator or spirometer.

In one embodiment calibration is done through measurement electrode pairs. In another embodiment, calibration is done through additional electrodes. In another embodiment, calibration is done all or in part by repurposing measurement electrodes and using the sensor as the delivery electrodes and the delivery electrodes as the sensor electrodes.

Preferably the calibration electrodes are placed in specific locations and/or at specific distances apart on the abdomen and thorax. In another embodiment, one or more of the leads are placed a specified distance apart on the forehead. In another embodiment of the device, the magnitude of the ICG signal across an acceptable electrode configuration with or without an estimation of the heart volume is used to determine the baseline impedance and calibrate the RVM data to respiratory volume. Preferably the calibration coefficient is calculated using a combination of the 5 previously mentioned methods.

Universal Calibration

While relations between respiratory and impedance variations are highly linear, the "scaling factor" between those values vary significantly from one patient to another. There is also day-to-day variation for the same patient. The day-to-day variations are correlated to some extent with physiological parameters measured by the RMV device and can be significantly compensated for. The residual day-to-day variations for the same patient are smaller than typical measurement error. In a preferred embodiment, this residual variation can be managed with existing ancillary measurements. In a preferred embodiment, this residual variation can be managed using ongoing or intermittent recalibration by any of the methods previously described.

In one embodiment, the "scaling factor" varies between patients by about an order of magnitude. In a preferred embodiment, this factor can be determined precisely by preliminary calibration with a spirometer or ventilator data or other data set. In a preferred embodiment, the RMV device is used for measurement of respiratory parameters without preliminary calibration. Preferably, a reliable procedure of deducing this factor from measurable patient physiological parameters is used for calibration. Such procedure allows the determination of the "scaling parameter" with sufficient precision to satisfy measurement requirements for all proposed device applications.

In one embodiment, measurements of respiratory motion derived from a technology including impedance plethysmography, accelerometers placed on the body, video images, acoustic signals or other means of tracking motion of the thorax, abdomen or other body parts is calibrated or correlated with another technology that assesses respiratory status. In a preferred embodiment, respiratory motion detection derived from impedance measurements is calibrated with spirometry. In one embodiment respiratory motion detection is calibrated or correlated with end tidal CO2 measurements. In one embodiment, respiratory motion detection is calibrated or correlated with ventilator measurements of flow and/or volume. In one embodiment, respiratory motion is calibrated with a full-body plethysmograph. In one embodiment, baseline RVM measurements of a given patient are taken in conjunction with standard spirometry measurements and a calibration coefficient for that particular patient is derived. Later in the postoperative period or otherwise, the calibration coefficients are used to obtain quantitative lung volume measurements for that patient. In a preferred embodiment, such calibration coefficients are combined with current baseline impedance or other physiologic measurements for ongoing or intermittent calibration. In one embodiment, preoperative measurements are used to derive a calibration coefficient which is then used, alone or in combination with other data, to obtain quantitative lung volume measurements to use in management of the patient after surgery or in other situations. In another embodiment, the calibration coefficient is derived from lung volume or flow measurements obtained on an intubated patient from measurements recorded from a mechanical ventilator.

Preferably the device is linked to a spirometer, ventilator or pneumotachometer to provide volume or flow calibration. Preferably, the device is linked to a spirometer or ventilator or pneumotachometer to provide volume calibration. In one embodiment, the operator will run the patient through a brief breathing test regimen of one or more of the following: at least one tidal breathing sample, at least one forced vital capacity (FVC) sample, at least one measurement of minute ventilation sample, and at least one maximum voluntary ventilation (MVV) sample. The device will be calibrated based on the results of the spirometer tests relative to the impedance measurements. In a preferred embodiment, calibration will be implemented from measurements taken during tidal breathing. In particular, for patients who are unable to comply with the procedure, a simple tidal breathing sample will be taken, which requires no coaching or compliance. The tidal breathing sample is collected over 15 seconds, 30 seconds, 60 seconds, or another time frame.

In one embodiment, a calibration coefficient for a given individual is calculated based on combined spirometry and RVM data and applied to deliver an absolute volume measurement for RVM measurements taken at a future time. Preferably, this absolute volume measurement will be validated or modified at the future time using calibration capabilities intrinsic to the hardware and current measurements derived from the device. In a preferred embodiment, an algorithm is applied to RVM data based on patient demographics, existing normal spirometry data for varying patient demographics found in the work of Knudsen, Crapo, and others and/or other anatomic or physiologic measurements to provide a universal calibration to deliver absolute volume measurements without the need for individual calibration with a spirometer or ventilator.

Preferably, the device may be used in conjunction with ECG or ICG data to produce further calibration of impedance data by utilizing parameters derived ECG and ICG such as heart rate and SNR. Preferably, ECG or ICG data will help validate proper electrode placement. In another embodiment, the electrical activity of the heart is used to enhance the device calibration. Preferably the device can measure the following cardiac, pulmonary and other physiology parameters and features: Heart Rate (HR), baseline impedance, impedance magnitude, Pre-ejection Period (PEP), Left Ventricular Ejection Time (LVET), Systolic Time Ration (STR), Stroke Volume (SV), Cardiac Output (CO), Cardiac Index (CI), Thoracic Fluid Content (TFC), Systolic Blood Pressure (SBP), Diastolic Blood Pressure (DBP), Mean Arterial Pressure (MAP), Mean Central Venous Pressure (CVP), Systemic Vascular Resistance (SVR), Rate Pressure Product (RPP), Heather Index (HI), Stroke volume Index (SVI), and Waveform Accuracy Value (WAV). Baseline values calculated from patient characteristics for these features are utilized to derive the calibration coefficient as well as calculate an index of overall respiratory sufficiency. Conversely, RVM data can be used to enhance accuracy or utility of ICG data such as Heart Rate (HR), baseline impedance, impedance magnitude, Pre-ejection Period (PEP), Left Ventricular Ejection Time (LVET), Systolic Time Ration (STR), Stroke Volume (SV), Cardiac Output (CO), Cardiac Index (CI), Thoracic Fluid Content (TFC), Systolic Blood Pressure (SBP), Diastolic Blood Pressure (DBP), Mean Arterial Pressure (MAP), Mean Central Venous Pressure (CVP), Systemic Vascular Resistance (SVR), Rate Pressure Product (RPP), Heather Index (HI), Stroke Volume Index (SVI), and Waveform Accuracy Value (WAV).

In particular, for patients who are unable to comply with a more complicated procedure, a simple tidal breathing sample of respirations at rest is taken, which requires no coaching or compliance. Analysis of these data provides information relative to pulmonary physiology and respiratory status that could not otherwise be obtained.

Figure 8:
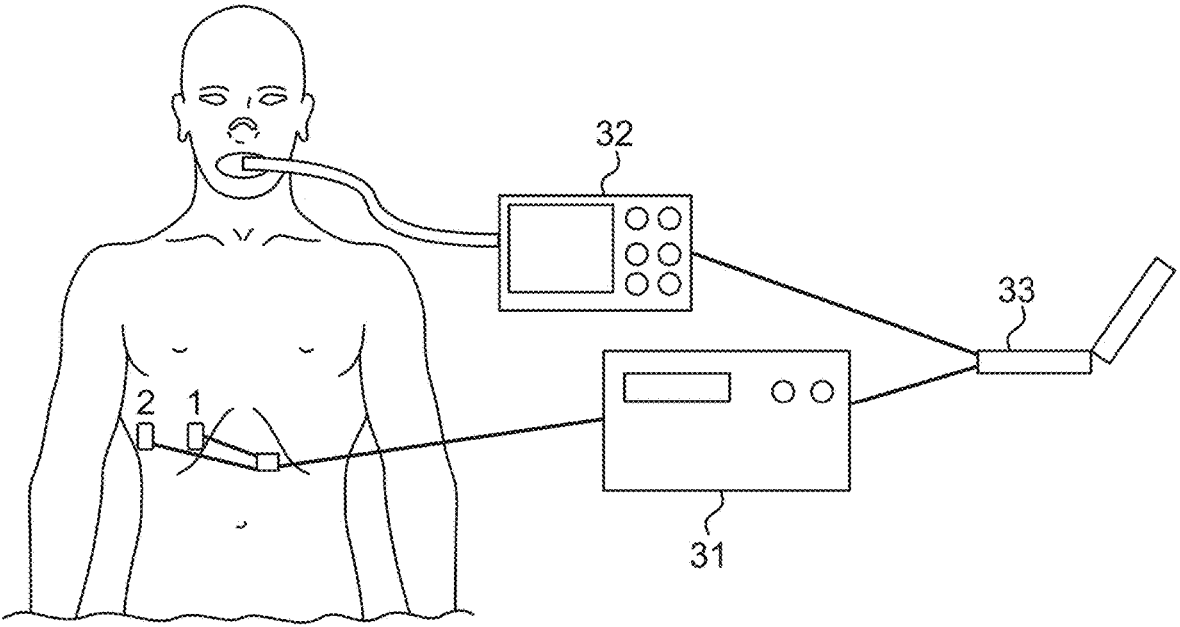
FIG. 8 is a perspective view of a four-lead embodiment of the invention connected to a spirometer.
Figure 9:
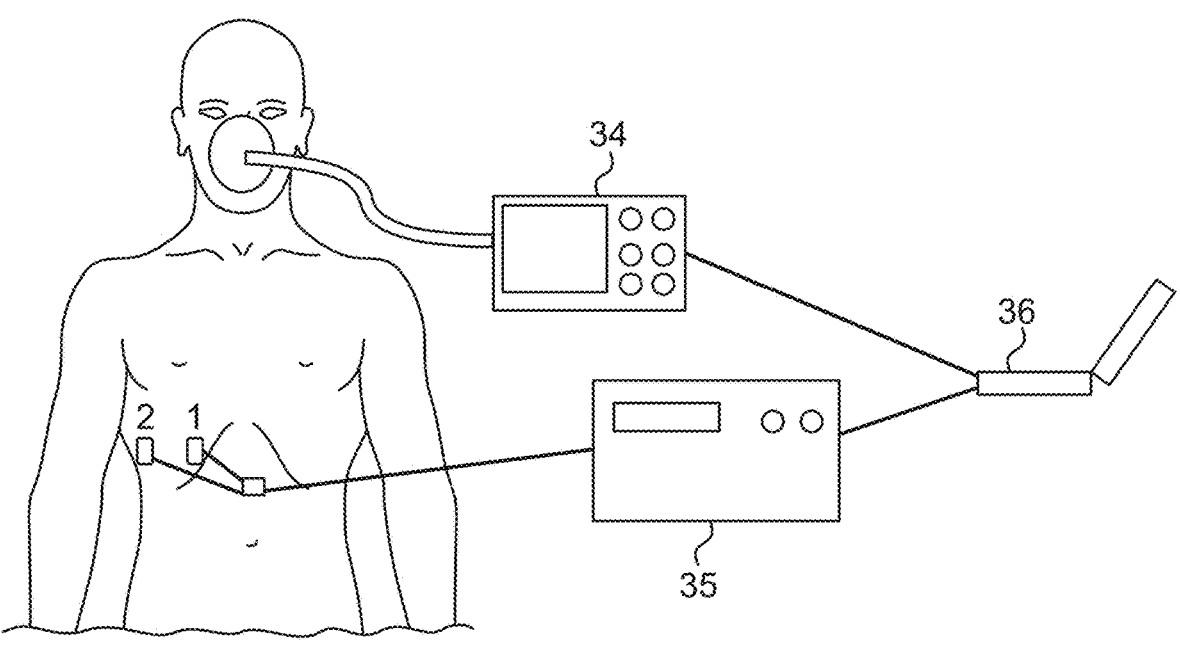
FIG. 9 is a perspective view of a four-lead embodiment of the invention connected to a ventilator.
Figure 10:
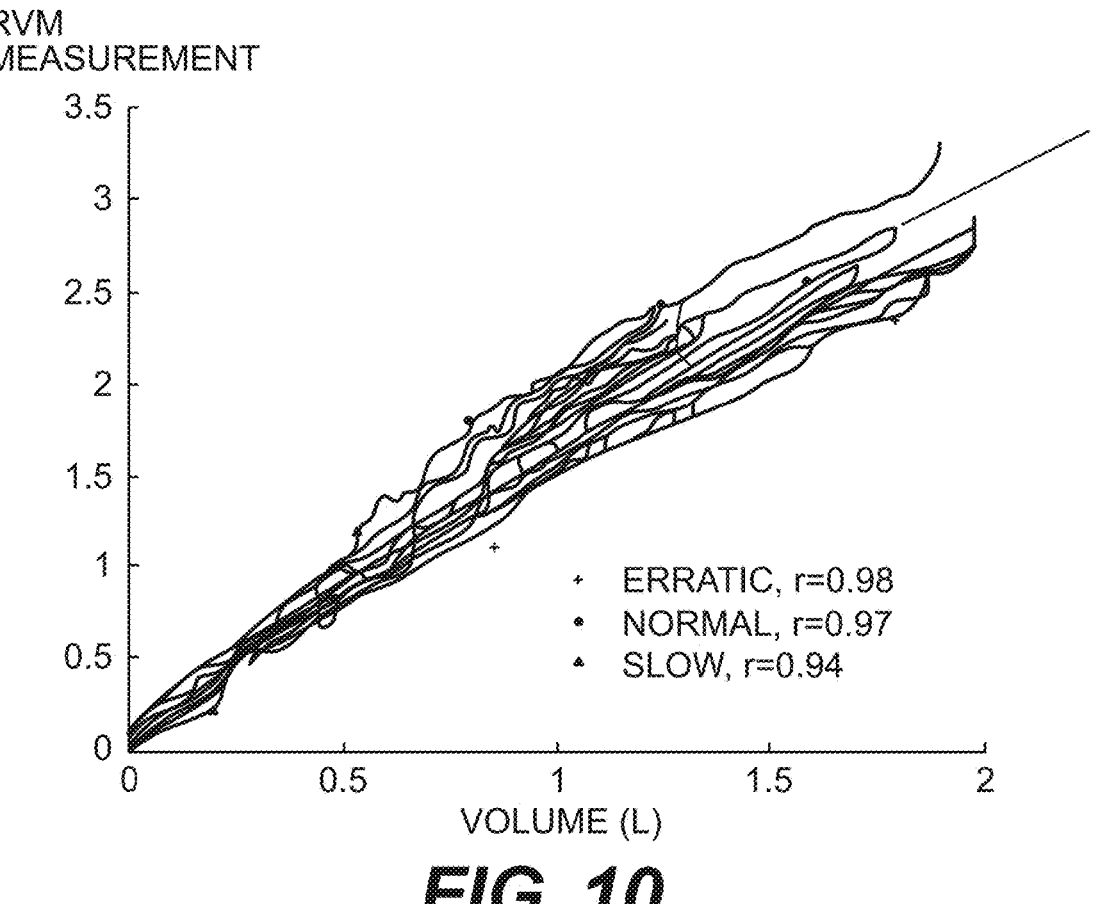
FIG. 10 is an RVM measurement (impedance) versus volume plot for slow, normal, and erratic breathing maneuvers.
Figures 11, 12:
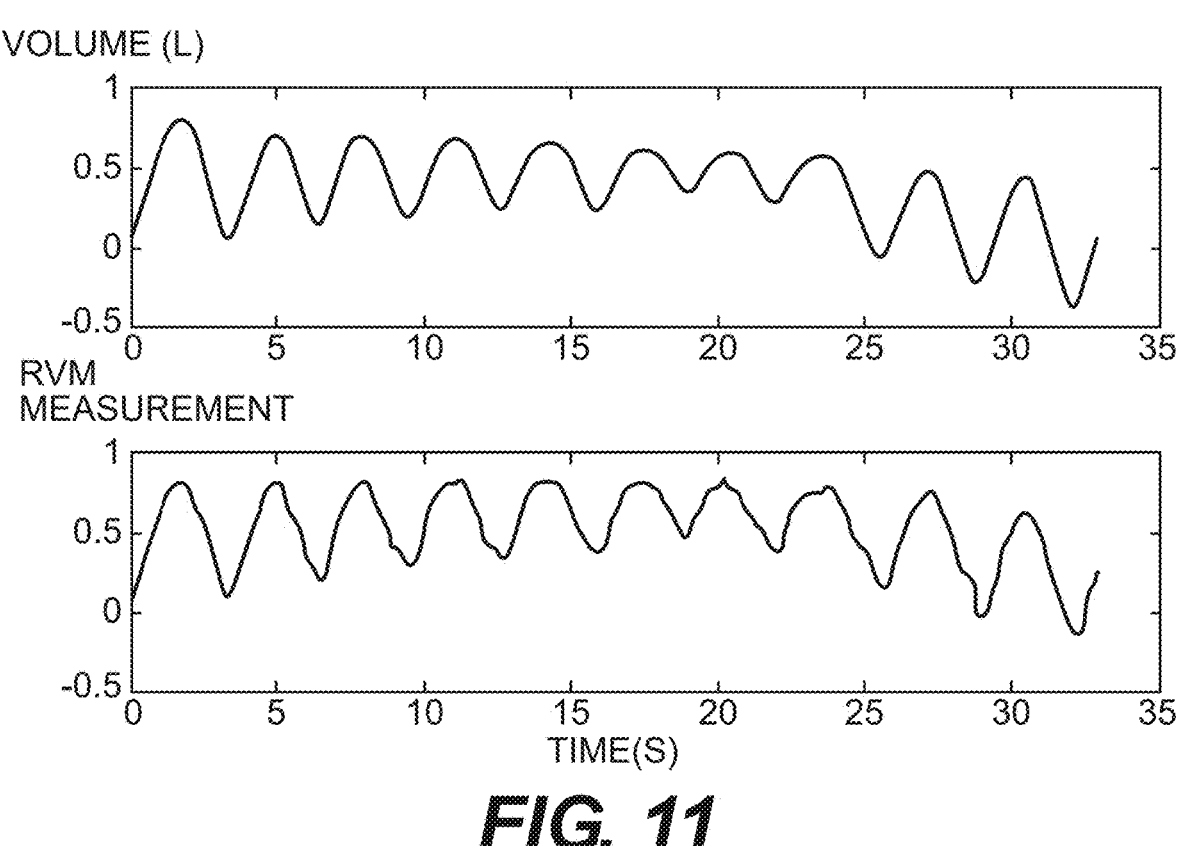
FIG. 11 is a set of RVM and volume plots against time for normal breathing.
FIG. 12 is a set of RVM and volume plots against time for slow breathing.
Figures 13, 14:
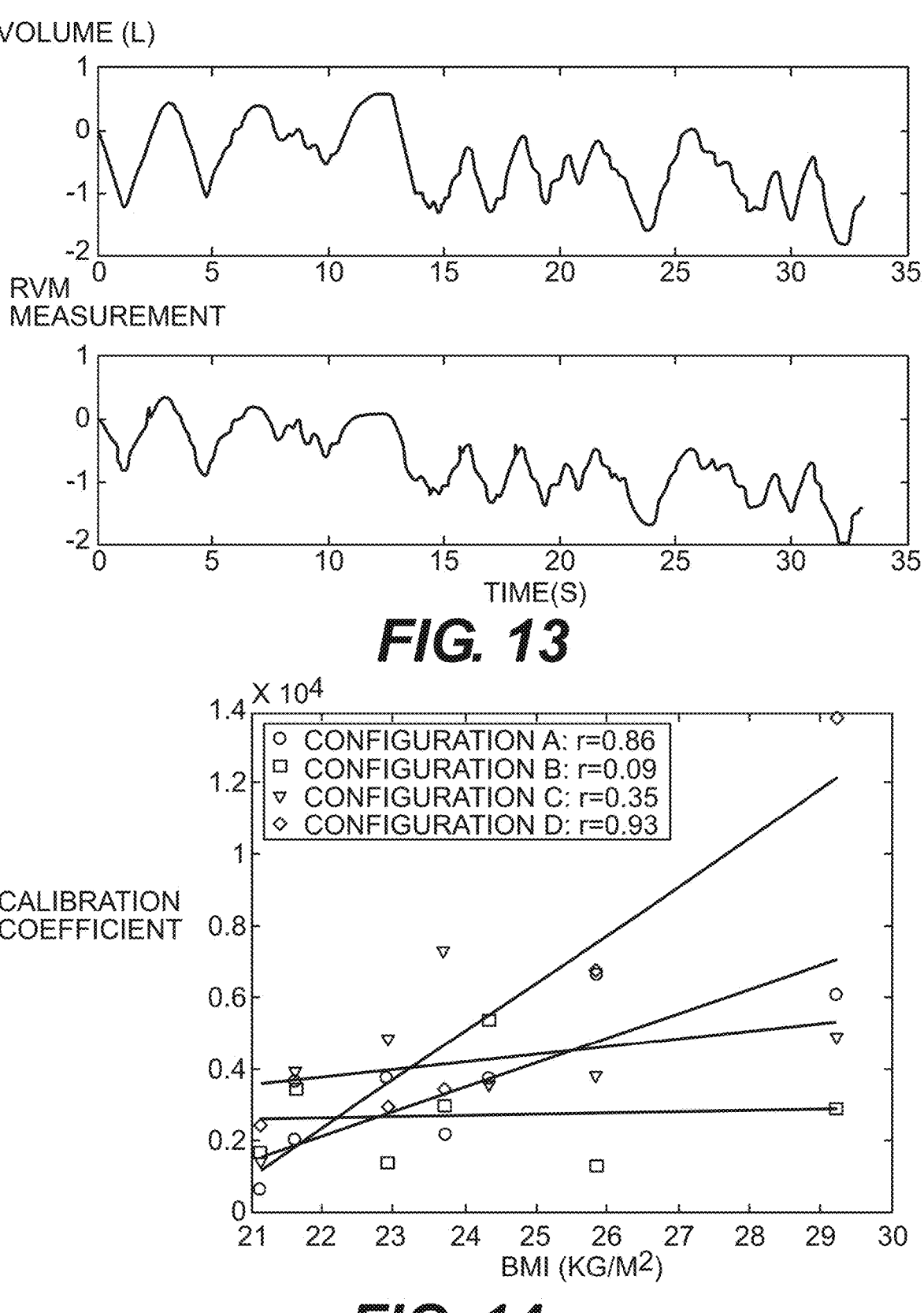
FIG. 13 is a set of RVM and volume plots against time for erratic breathing.
FIG. 14 is a plot of calibration coefficients against BMI for four different electrode configurations.

Referring now to FIG. 8, there is shown an impedance plethysmograph 31 and a spirometer 32 both functionally connected to the same programmable element 33. Volume data from the spirometer is preferably sampled simultaneously or nearly simultaneously with the impedance reading of the impedance plethysmograph. Referring now to FIG. 9, there is shown a patient who is connected to a ventilator 34 as well as the impedance plethysmograph 35, both functionally connected to a programmable element 36. The volume of the ventilator is sampled simultaneously with the impedance reading of the impedance plethysmograph. Referring now to the graph in FIG. 10, there is shown a graph of volume versus impedance for a given patient undergoing various breathing maneuvers while data was simultaneously collected using the impedance plethysmograph and a spirometer. The trace represented by FIG. 11 with volume over time is normal breathing. The trace represented by FIG. 12 is slow breathing and the trace represented FIG. 13 is erratic breathing. In one embodiment, the slope of the line of best fit 37 is used as the RVM calibration coefficient to compute volume from impedance. In another embodiment, an algorithm utilizing the slope, shape and/or other curve characteristics and/or other demographic or body habitus characteristics of the patient is used to calculate the calibration coefficient.

In one embodiment a simple numerical value is obtained from a ventilator or spirometer for tidal volume or minute ventilation for use in calibration of the device. One embodiment is comprised of a combined system in which RVM and volume measurements are taken simultaneously, nearly simultaneously, or sequentially by means of a spirometer, pneumotachometer, ventilator or similar device and the combined data utilized to create an individual calibration coefficient for the calculation of absolute volume from RVM measurements for a given individual.

EXAMPLE

One method of calibration has already been utilized in a small-scale study. Measurements of height, weight, chest circumference at maximum inspiration and normal expiration, distance from suprasternal notch to xiphoid, distance from under mid-clavicle to end of rib cage in midaxillary line, distance from end of rib cage to iliac crest in midaxillary line, and abdominal girth at umbilicus were taken and recorded. Electrodes were positioned at the Posterior Left to Right, Posterior Right Vertical, and Anterior-Posterior, and ICG configuration discussed above. The four probes of the impedance measurement device were connected to the electrodes that corresponded to one of the configurations above. The ICG position was connected first and only used to measure resting ICG of the subject in a supine position. The leads were then reconfigured to connect to the Posterior Left to Right position. Once the leads were positioned correctly and the subject was supine, the subject performed breathing tests which were measured simultaneously by the impedance measurement device and a spirometer for a sampling time of about 30 seconds. The breathing tests performed were normal tidal breathing (3 runs), erratic breathing (2 runs), slow breathing (2 runs), Forced Vital Capacity (FVC) (3 runs), and Maximum Ventilatory Volume (MVV) (2 runs). FVC and MVV were performed according to ATS procedures. Normal, erratic, and slow tests were measured by a bell spirometer, and FVC and MVV were measured by a turbine spirometer. Preferably, the calibration can be run all together on any type of spirometer that meets ATS standards. Once all breathing tests were complete, the leads were repositioned to a new configuration, and the tests were run again until all configurations had been tested. The data was collected on PC for the impedance data and turbine spirometer data, and on another PC for the bell spirometer data. The data was then merged onto one PC and loaded into MATLAB. Preferably, MATLAB or other software packages that utilize signal processing are used. Preferably, the data is loaded onto a PC or other computing station. Once the data was merged, the impedance and volume data from each breathing test were matched together using a GUI-based program. Correlation coefficients and calibration coefficients were produced for each of the test runs by comparing the impedance and volume traces using MATLAB. This data then was utilized in Excel to predict calibration coefficients based on patient characteristics. Preferably, the data can be imported into and analyzed in any software with a statistical package.

Referring now to FIG. 14, depicted is a graph of BMI versus the calibration coefficient for 7 patients. BMI is shown on the x-axis, and calibration coefficient is shown on the y-axis. The linear relationship between height and the calibration coefficient in configuration D (PRR placement as described earlier) is indicative of its utility in determining the calibration coefficient. Other physiological parameters such as height weight, body surface area, race, sex, chest circumference, inter-mammary distance, age also have important relationships with the calibration coefficient, and in one embodiment any or all of these parameters aid in accurate determination of the calibration coefficient. A combination of statistical analysis and an expert system is used to determine a given patient's correlation coefficient based on the input of said physiological parameters. Such methods may include principal component analysis, artificial neural networks, fuzzy logic, and genetic programming and pattern analysis. In a preferred embodiment, test data from a pilot study is used to train the expert systems. In a preferred embodiment, existing data regarding patient demographics and pulmonary function are used to train the expert system. Preferably, a combination of test data from a pilot study and existing pulmonary function datasets are use to train the expert system.

Figure 15:
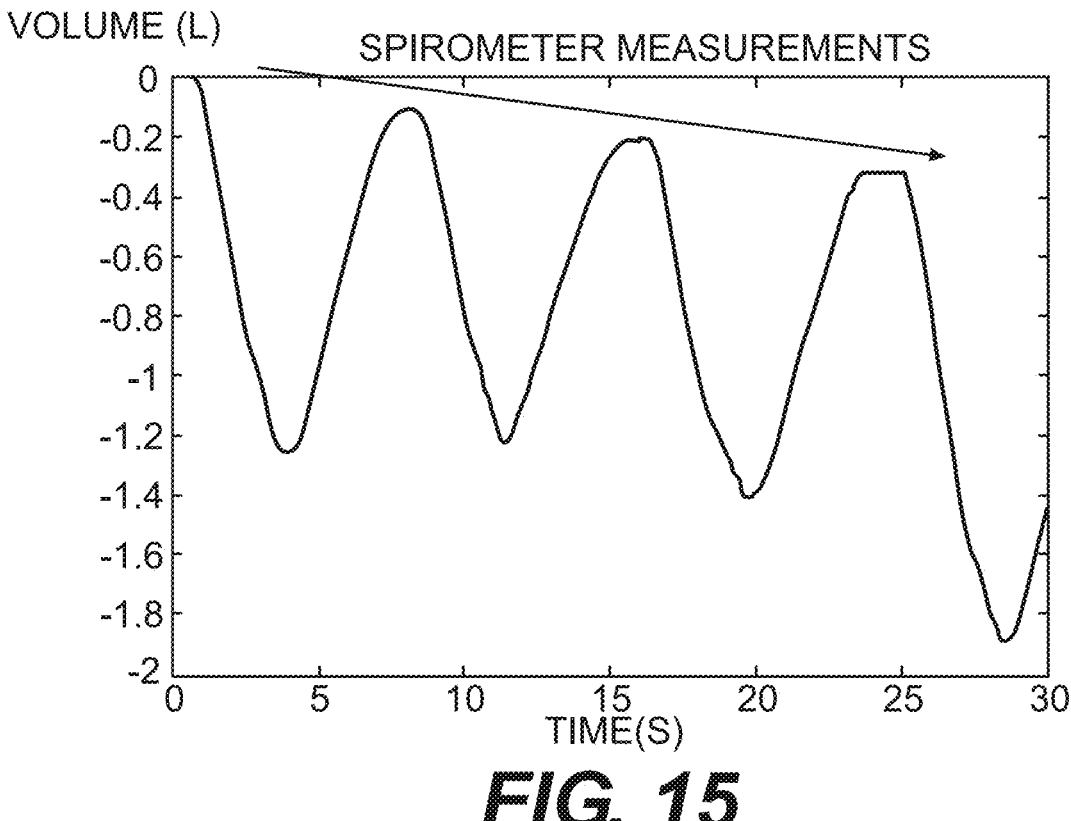
FIG. 15 is a spirometry plot that exhibits volume drift.
Figure 16:
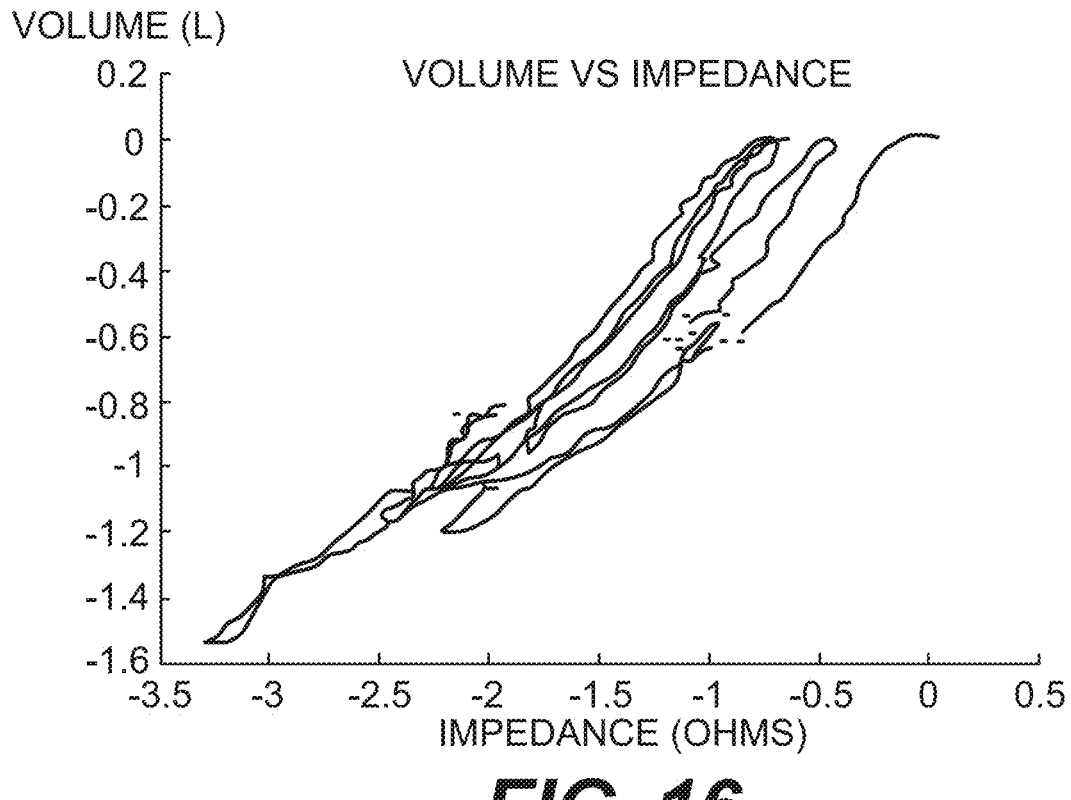
FIG. 16 is a volume vs. impedance plot that is affected by volume drift.
Figure 17:
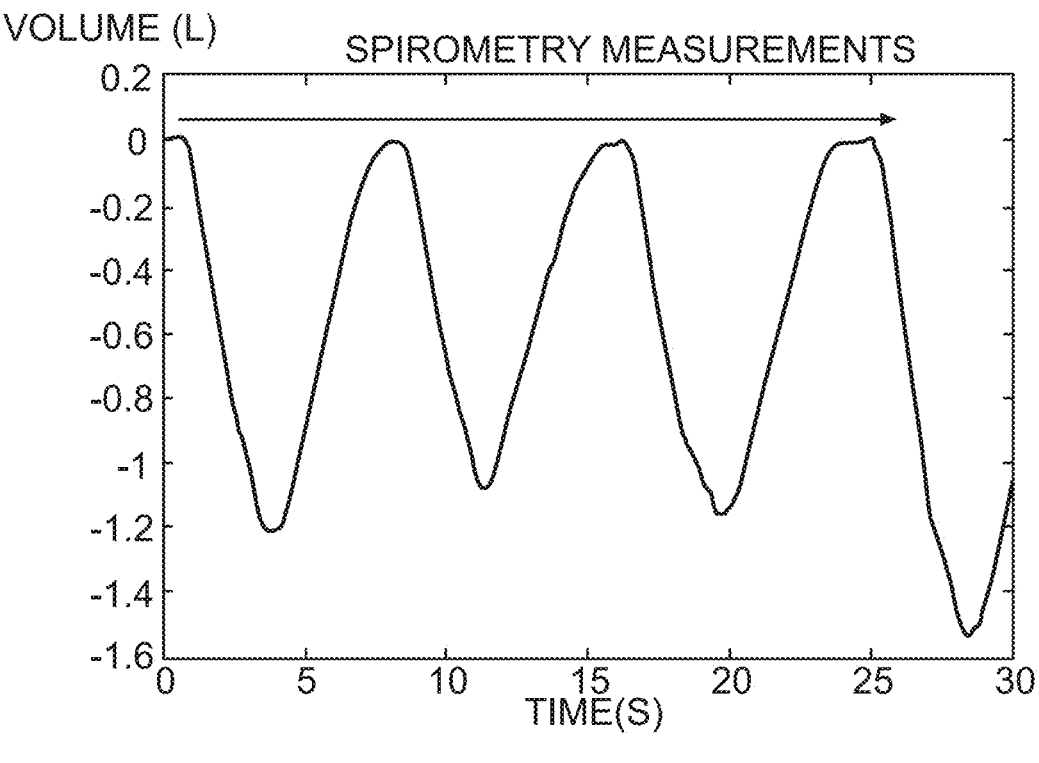
FIG. 17 is a spirometry plot that is corrected for volume drift.
Figure 18:
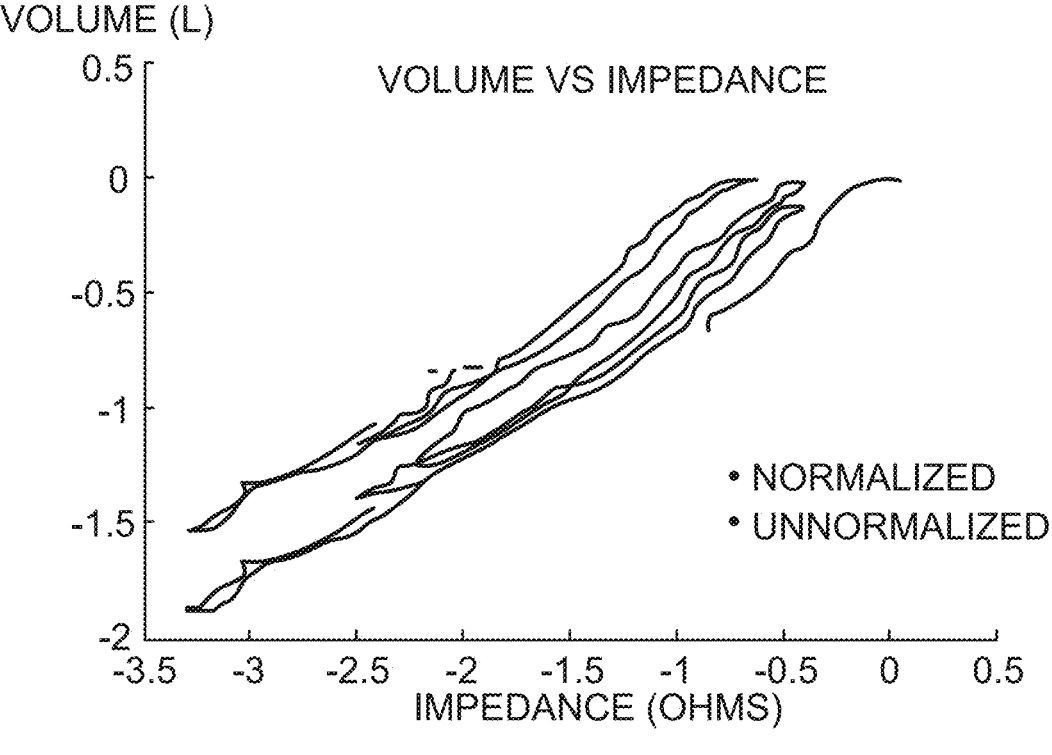
FIG. 18 is a plot of volume vs. impedance, comparing data that is uncorrected and corrected for volume drift.

One problem that is encountered with some spirometers is volume drift, where a greater amount of air is inspired rather than expired. Additionally, prolonged spirometry testing provides increase in resistance to pulmonary flow that can alter the physiology and/or can change the respiratory flows and/or volumes. These patterns can disrupt the correlation coefficient for the test by altering the volume so that it trends downwards while the impedance trace stays constant. FIG. 15 shows a volume curve that exhibits volume drift. FIG. 16 shows a volume versus impedance curve for that set where the volume drift damages the fit of the plot. In one embodiment, the device corrects for the problem by subtracting out a line with a constant slope value. After using this mean flow method, the curves do not trend up or down as seen in FIG. 17 and the volume versus impedance data stays much tighter as seen in FIG. 18, and the volume versus impedance data stays much tighter, giving higher correlations and better correlation coefficients. In one embodiment, volume drift subtraction is used in calibration. In one embodiment volume drift subtraction is used in deriving the calibration coefficient. The same utility is also achieved by differentiating the volume curve to get flow, subtracting the DC offset between intervals that have the same lung volume at the start and end point, and then integrating to get flow without the drift artifact.

In another embodiment of the device, the calibration coefficient is determined by comparing the RVM data trace and calculated values compared to predicted values for the patient's tidal volume, FVC, FEV1 etc. based on standard tables of spirometric data created by Knudsen, Crapo, or others known to those skilled in the art.

Data Analysis

Figure 19:
FIG. 19 is a flow chart that describes data analysis for the invention.

Referring now to FIG. 19, there is shown a flow chart that displays the progression of data through the analysis software. Raw data is recorded by the impedance meter, digitized using an analog to digital converter, and inputted to the programmable element through a standard data port. Data processing strips the signal of noise and motion artifacts. Analysis algorithms calculate the volume trace as well as medically relevant information including but not limited to: frequency and time domain plots of the impedance and/or calculated volume traces, respiratory rate, tidal volume, and minute ventilation. In one embodiment, the analysis algorithm to convert impedance into volume traces utilizes either calibration in conjunction with spirometer or ventilator data, or in another embodiment, calibration based on physiological parameters. The algorithm produces a correlation coefficient which, when multiplied with the impedance data, converts the impedance scale into a volume scale. In addition, the algorithms take variability of the above metrics into account and automatically calculate a standardized index of respiratory sufficiency (RSI). This RSI contains information that integrates information from one or more measurements and/or utilizes the range of acceptable values of the following measurements individually and in combination to provide a single number related to respiratory sufficiency or insufficiency: respiratory rate, respiratory volume, respiratory curve characteristics, respiratory variability or complexity as previously prescribed.

In one embodiment, one of the following methods are used in calculation of the RSI: change in patient status from previous measurement, second derivative of change in patient status from previous measurements, multivariate analysis, pattern analysis, spectral analysis, neural networks, self-teaching system for individual, self-teaching system for patient population.

In one embodiment, the RSI also includes data from the following: oxygen saturation, TcpO2, TcpCO2, end tidal CO2, sublingual CO2, heart rate, cardiac output, oncotic pressure, skin hydration, body hydration, and BMI. The advantage of this index is that it can be understood by untrained personnel and it can be linked to alarms to notify physicians or other caregivers in case of rapidly deteriorating health. After computation, processed metrics pass to the output module, which may be embodied as a printer or displayed on a screen or delivered by oral, visual, or textual messaging.

In one embodiment, the device notes a pattern in the curve recorded during the inspiratory or expiratory phase of respiration. In one embodiment, the device notes a pattern in the respiratory variability in rate, volume and/or location of respiration. In one embodiment the pattern is noted in the shape of the respiratory curve. In one embodiment, the pattern analysis includes the values derived from the slope of inspiration. In one embodiment, the pattern analysis includes the values derived from the slope of expiration. In one embodiment, the pattern analysis includes a combination of parameters which could include any or all of the following: respiratory rate, minute ventilation, tidal volume, slope of inspiration, slope of expiration, respiratory variability. In one embodiment, these parameters are used within the calculation of a Respiratory Health Index (RHI) that provides a standardized quantitative measure of adequacy of ventilation. In one embodiment, the RHI is coupled with alarms that sound either when respiration falls below what is deemed as adequate, or within the range that is deemed adequate, if the patient experiences a very sudden change. In one embodiment, the device provides information to calculate an RHI. Preferably the device calculates and displays the RHI. In one embodiment, the Respiratory Health Index is compared against a universal calibration based on patient characteristics. In one embodiment, the RHI provides quantitative data with the system calibrated to a specific patient.

Figure 27:
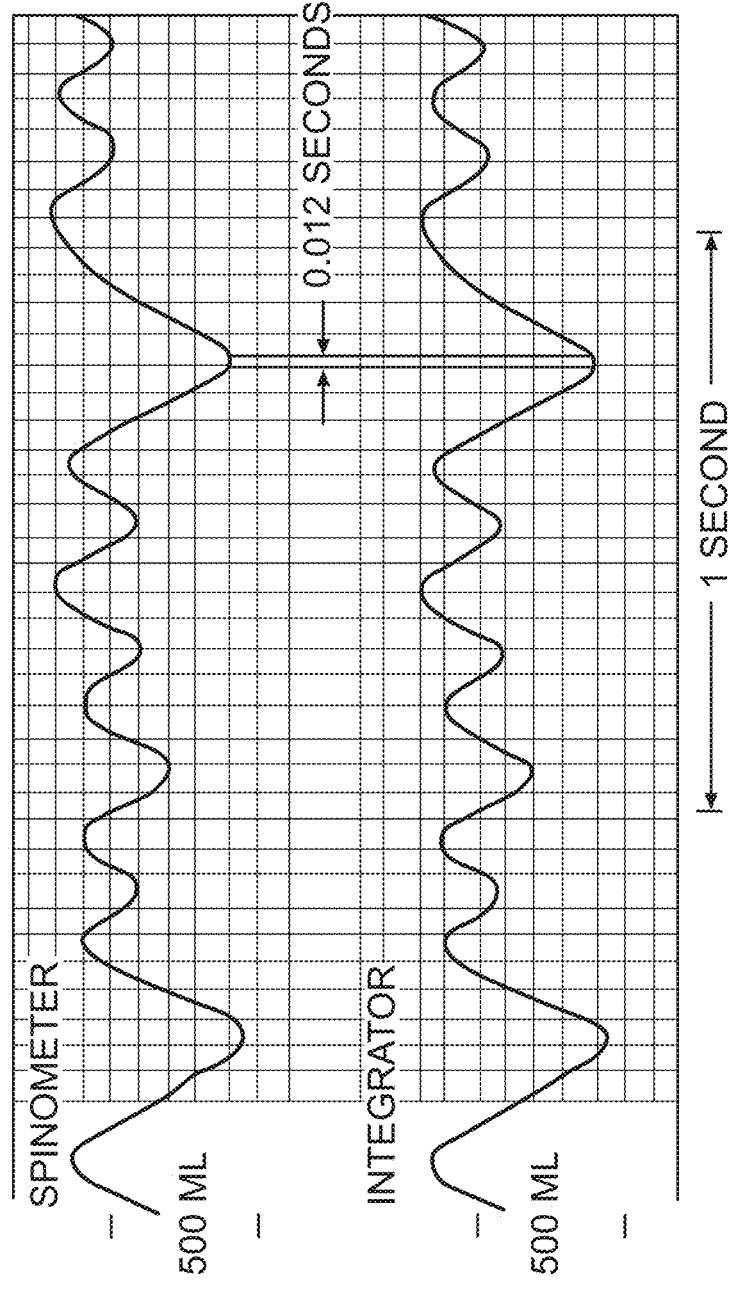
FIG. 27 shows graphs of impedance versus time and volume versus time for simultaneously recorded data.

Referring now to FIG. 27, the time delay or phase lag of an impedance signal and a volume signal is shown. In this particular figure, the delay was found to be 0.012 seconds. Phase lag between volume and impedance signals is an important issue that is addressed in one embodiment. There is a time lag between impedance and volume signals due to the elastic and capacitive nature of the pleura and lung tissue, which creates a slight delay between the diaphragm moving and air flowing in the lung. In one embodiment, this phase difference is used as a measure of lung stiffness and airway resistance. Frequency phase analysis allows the user to find the phase angle. A larger phase offset is indicative of a high degree of airway resistance to motion. Calculation of the phase angle is accomplished by comparing simultaneously recorded and synchronized RVM curves with flow, volume or pressure curves recorded by a spirometer, pneumotachometer, ventilator or similar device. In one embodiment the phase lag between volume and impedance signals is a component of the algorithm that is used to calibrate the system to a given individual. In one embodiment the phase lag is used to calibrate the system for a universal calibration. When calculating the calibration coefficient using an external pressure, flow, or volume measuring device, the leading curve is shifted by the magnitude of the phase lag so as to correlate temporally with the trailing curve. This embodiment increases the accuracy of the calibration algorithm. When no external pressure, flow, or volume measuring device is used for calibration, a virtual phase lag is calculated based on patient characteristics, including demographic information, physiological measurements, and pulmonary function test metrics.

In one embodiment, phase lag is corrected for by RVM algorithms in aligning both impedance and volume. In one embodiment, phase lag data is presented independently as a standardized index to demonstrate a measure of lung compliance and stiffness. In one embodiment, phase lag data is integrated within the Respiratory Health Index as a measure of respiratory status.

In one embodiment, frequency domain analysis is applied to the RVM measurements. Preferably, at least one frequency domain plot such as a Fourier transform is displayed to the operator. Preferably, at least one 2-dimensional frequency domain image of the RVM data such as a spectrograph is displayed to the operator, where one dimension is frequency and the other is time, and the magnitude of the signal at each location is represented by color. Preferably, the frequency domain information is used to assess respiratory health or pathologies. Preferably, an alarm will alert a medical professional if the frequency domain data indicates rapid deterioration of patient health.

In a preferred embodiment, RVM measurements are used as the basis for complexity analysis. In one embodiment, complexity analysis is performed on the RVM signal alone. Preferably, RVM measurements are used in combination with other physiologic measurements such as heart rate, urine output, EKG signal, impedance cardiogram, EEG or other brain monitoring signal.

In a preferred embodiment, RVM measurements are utilized as a component of complexity analysis in combination with data provided by a device used to treat or monitor the patient including: the ventilator measurement of the patient generated respiratory pressure, the ventilator measurement of the patient generated respiratory flow, the ventilator measurement of the patient generated respiratory volume, the ventilator measurement of the ventilator generated respiratory pressure, the ventilator measurement of the ventilator generated respiratory flow, the ventilator measurement of the ventilator generated respiratory volume an infusion pump, or other devices used to treat the patient, RVM measurements may be used to quantify breath-to-breath variability. One embodiment of the device is used to define a specified point along the respiratory curve with which to calculate breath-to-breath variability in respiratory rate such as the peak of inspiration or nadir of expiration. Preferably, peaks or nadirs of each respiration are automatically identified. In one embodiment, the device provides data with describing breath-to-breath variability in volume inspired. In one embodiment, the device provides data describing breath-to-breath variability or complexity in the slope or other characteristics of the respiratory volume or flow curve. In one embodiment, the device provides data with which to calculate variability or complexity associated with the location of respiratory effort, such as chest vs. abdominal or one hemithorax vs. the other, by collecting data from different locations on the body with the same or different electrode pairings. Preferably, the device calculates breath-to-breath variability or complexity of one or more of these parameters. Preferably, the device presents the variability or complexity analysis in a form that is easy to interpret by the user. In one embodiment, the device combines data from more than one source of variability or complexity among the following: respiratory rate, respiratory volume, location of respiratory effort, slope or other characteristic of the respiratory volume or flow curves, to provide an advanced assessment of respiratory function. In one embodiment, the device analyzes the variability or complexity data intermittently or continuously and presents the data at intervals such as every 10 minutes, every 30 minutes, or every hour. Preferably, the device presents the variability analysis in less than 10 minutes, less than 5 minutes, less than 1 minute, or in near real time. In one embodiment, the variability or complexity of any of the respiratory parameters may be quantified by linear or nonlinear analysis methods. Preferably, the variability or complexity of any of the respiratory parameters may be quantified by nonlinear dynamical analysis. In one embodiment, approximate entropy is used by the device for data analysis. In one embodiment, variability or complexity analysis of the data is combined with volume data to provide a combined index of respiratory function. In one embodiment, variability or complexity analysis data is combined with other parameters and presented as a Respiratory Sufficiency Index or a Respiratory Health Index.

In a preferred embodiment, RVM measurements or the complexity analysis of the RVM signal is utilized as at least a part of the information used in goal directed therapy. In a preferred embodiment, RVM measurements or the complexity analysis of the RVM signal provide information for decision support. In a preferred embodiment RVM measurements or the complexity analysis of RVM signal is utilized as at least a part of the patient data required for a controlled loop system.

Use in Imaging

In one embodiment of the device, the respiratory cycle is measured by one or more methods including but not limited to impedance pneumography, end tidal $CO_2$, or pulse oximetry while the heart is imaged or otherwise measured using echocardiography which may be embodied as 2D echo, 3D echo or any other type of echocardiography. Time series data from the echocardiogram is marked as having a certain accuracy rating based on the respiratory motion recorded by the respiratory monitor. In one embodiment, echocardiography data below an accuracy threshold is discarded. In another embodiment, echocardiography data is weighted based on its accuracy rating where the least accurate data is weighted lowest. The device generates a composite image or video of the heart and cardiac motion based on the most accurate echocardiogram data. In one embodiment, echocardiography data is recorded over more than one cardiac cycle, then after analysis and accuracy rating, the best data is used for generating a composite image of the heart or video of the cardiac cycle.

Other embodiments include combining respiratory cycle measurement and quantification with other cardiac imaging techniques for the purpose of improving accuracy. The methods of cardiac imaging may include Doppler flow measurements, radionuclide study, gated CT, and gated MRI. Other embodiments include combining respiratory cycle measurement by RVM with other diagnostic or therapeutic modalities of the chest, abdomen, and other body parts, including diagnostic CT or MRI, catheter directed therapy, directed cardiac ablation, radiofrequency ablation of tumor, radiation of tumor. In a preferred embodiment, RVM and cardiac impedance data are utilized together for timing of data collection or data analysis of diagnostic imaging or anatomically directed therapy.

In another embodiment of the device, the respiratory impedance measurements or data from complexity analysis of RVM measurements are used to generate an image of the lungs. In another embodiment of the device, data from complexity analysis of RVM measurements and cardiac impedance measurements are used to generate an image of the heart and lungs. In the preferred embodiment, the heart and lungs are imaged simultaneously. In one embodiment, the device is used for generating 2D images, videos, or models of the heart and/or lungs. In the preferred embodiment, the device generates 3D images, videos or models of the heart and/or lungs.

Detecting Pathologies and Improving Monitoring

In one embodiment, the device provides RVM data which, with our without variability or complexity analysis, is used to aid in decision making such as extubation or intubation for mechanical ventilation. In one embodiment the device provides RVM data which, with or without variability or complexity analysis, aids in decision making regarding drug administration or other therapeutic intervention. In one embodiment, the device uses variability or complexity information alone or with volume data as part of an open or closed loop control system to adjust ventilatory settings. In one embodiment, the device uses variability or complexity information, alone or with volume data or other analysis of the respiratory curve provided by RVM, as part of an open or closed loop control system to adjust doses of medications. This embodiment is useful for premature infants to optimize the management of a pressure ventilator, and for patients with uncuffed endotracheal tubes. In one embodiment, the device uses variability or complexity information, alone or with volume data or other analysis of the respiratory curve provided by RVM, as part of a patient management system that monitors patient status, recommends medication delivery, and, then, reassesses the patient to direct further action.

In one embodiment the device uses variability or complexity analysis of the RVM signal alone, volume data alone, curve analysis alone, or any of these in combination to trigger alarms indicating change in patient status. In another embodiment, symbol-distribution entropy and bit-per-word entropy are used to measure the probability of patterns within the time series. In another embodiment, similarity of distributions methodology is used. In one embodiment, the device sounds an alarm when it detects a change in respiratory complexity or a respiratory complexity below a specified threshold or more constrained breathing patterns associated with pulmonary pathology or disease states. In one embodiment, the device sounds an alarm when it detects a change in a combined measurement of respiratory and heart rate complexity beyond a specified threshold.

In one embodiment, RVM measurements are integrated into an open or closed feedback loop to report adequacy of ventilation by ensuring safe dosage of medication by monitoring ventilation for warning signs of respiratory arrest. In a preferred embodiment, RVM is integrated into a system with a ventilator providing an open or closed feedback loop by which ventilator adjustments are made. Differences between RVM measurements and ventilator or spirometer generated volume or flow measurements can be used to provide information for diagnosis and guidance of therapy. By using RVM monitoring with or without additional information from end tidal $CO_2$ or pulse oximetry measurements, this embodiment automatically weans the patient by gradually decreasing ventilatory support and observing RVM and other parameters and alerts the physician of readiness for extubation, or alerts for failure to progress. The system may additionally include machine intelligence in the form of supervised and unsupervised learning based on patient's own and/or population-based data. Preferably the system is able to provide clinical guidance and suggestions for ventilator-regulation use.

This combined system with either pulse oximetry or ETCO2 or both could be used as an open or closed loop system to deliver narcotics or other respiratory depressant drugs such as benzodiazepines or propofol.

In one embodiment, the analysis algorithm detects the presence of specific respiratory patterns maintained in the expert system database and informs the physician or other health care provider about the possibility of associated pathology. In one embodiment, the respiratory pattern for a given pathology is recognized and in a preferred embodiment, quantified. In another embodiment the pathology is localized.

In a preferred embodiment, the device recognizes a specific patterns related to respiratory volume, curve, variability or complexity or other analysis of RVM data.

In one embodiment, the device recognizes the pattern associated with impending respiratory failure or respiratory arrest and delivers an audible and/or visible alert or warning. In one embodiment, the device analyzes the respiratory data or the trend in the data and makes a recommendation for intubation and mechanical ventilation. In one embodiment, the device analyses the respiratory pattern data and adjusts the level of infusion of a narcotic or other respiratory depressant drug such as propofol.

In one embodiment, the device recognizes the respiratory pattern associated with a specific disease entity or pathology such as congestive heart failure, or asthma or COPD or narcotic induced respiratory depression or impending respiratory failure. In one embodiment, the device alerts the physician to this pathology. In one embodiment the device quantifies the degree of the pathology. In one embodiment, the device recognizes a pattern of congestive heart failure and provides data regarding the trending toward improvement or deterioration with time or as associated therapeutic intervention.

Preferably, the impedance measuring element of the device can produce Impedance Cardiograph (ICG) measurements. Preferably, the device detects impedance variability associated with heart rate variability. Preferably the device detects impedance variability associated with variability of the respiratory waveform or other respiratory parameter and utilizes the heart rate and respiratory rate, volume or waveform variability to predict cardiac, respiratory and pulmonary complications. Preferably, the device maintains alarms for predetermined limits associated with unsafe pulmonary variability or complexity or combined heart rate and respiratory variability or complexity.

In another embodiment, End Tidal $CO_2$ (ETCO$_2$) is used in addition to or instead of subjective assessment to determine the RVM baseline. In one embodiment, RVM is coupled with ETCO$_2$ measurements to provide additional information regarding respiratory status.

In another embodiment RVM is coupled with pulse oximetry to provide information about both ventilation/respiration and oxygenation. A more complex RVM system couples standard RVM measurements with both or either ETCO$_2$ or pulse oximetry. This combined device provides further information about breathing for sedated patients and enhances patient monitoring.

In a preferred embodiment, measurements of lung volumes and minute ventilation are used to assess the adequacy of the patient after extubation in a quantitative way. Minute ventilation is specifically used for patients undergoing surgery. Preferably, a preoperative measurement of tidal volume or minute ventilation is obtained as a baseline for the specific patient. Preferably the baseline is used post-operatively as a comparison between preoperative and postoperative respiratory status. The trend of tidal volume or minute ventilation is used to monitor a patient during surgery or a procedure or during post-operative recovery in the Post Anesthesia Care Unit, in the Intensive Care Unit, or on the hospital floor. This trend gives an accurate measure of differences and changes in the patient's breathing from pre-procedure baseline and can denote when the patient returns to a baseline level of breathing. In a preferred embodiment, the device directly aids the physician to make an appropriate extubation decision by defining an adequate level of breathing specific to that patient. In one embodiment, absolute lung volumes are compared with pre-calibrated data derived from patient characteristics, and are used in determining the presence of restrictive and/or obstructive lung disease and other respiratory conditions. Absolute volume data can be especially useful within the PACU and ICU as a complement to existing quantitative data.

The system is preferably capable of monitoring patient's respiratory status before and after extubation, providing recommendations for additional respiratory treatment or medications (if necessary) or indicating that there is no need for further treatment and the patient is ready for transfer off of mechanical ventilation, CPAP, BiPAP, or High-flow O2. The system is preferably capable of detecting small breaths that may not be otherwise detected by a ventilator. Preferably, the system may be able to provide an extubation trial before actual extubation, while monitoring data to support the extubation.

In one embodiment, the system preferably provides an indication of the need to intubate or re-intubate a patient. The indication may be audible and/or visual. In another embodiment, the system preferably controls external ventilation and respiratory treatment or therapy via either open and close loop based on the RVM measurements.

In another embodiment, the system preferably performs real-time analysis of shape of the expiratory and inspiratory impedance or tidal volume signal curve to determine at least one of: readiness for extubation, need for intubation, need for re-intubation, and need for additional treatment. In another embodiment, the system preferably provides real-time feedback and control of the ventilator to prevent damage to the lungs from over distention of the alveoli, resulting from either mechanical ventilation (VILI) or spontaneous ventilation (SILI) or to prevent damage through excessive driving pressure.

In another embodiment, the system will preferably perform real-time analysis of the flow-volume loops, specifically the hysteresis in those loops, to determine at least one of: readiness for extubation, need for intubation, need for re-intubation, need for additional treatment. In another embodiment, the system will preferably provide real-time feedback to prevent damage to the lungs from over distention of the alveoli, resulting from either mechanical ventilation (VILI) or spontaneous ventilation (SILI) or to prevent damage through excessive driving pressure. In another embodiment, the system preferably provides real-time feedback identifying Atelectasis, the collapse or closure of the lung in which the alveoli have little or no volume.

Use in PCA feedback and Drug Dosing Optimization

One use of the device is to use cardiac and/or respiratory data measured and recorded by one, several, or a combination of the technologies listed herein, to determine the effect of one or more drugs or other medical interventions on the patient. In an embodiment, the respiratory monitor is used to judge the side effects of analgesic drugs on the body and prevent or assist in the prevention of respiratory failure or other compromises due to adverse reaction or overdose.

In a preferred embodiment, the device is paired with or integrated into a patient controlled analgesia (PCA) system. This is accomplished electronically through communication between the device of the invention and an electronic PCA system, or by an integrated monitor/PCA system or by a setting in the monitor indicating that the patient is being administered PCA. In this embodiment, the administration of analgesia or anesthesia is limited based on the risk of respiratory or other complications predicted by the device. If the PCA system is not electronic, or analgesic drugs are being delivered by personnel, the device makes recommendations as to when the risk of respiratory complication is high and the dosage should be lowered.

Another embodiment of the device of the invention is a diagnostic/therapeutic platform. The monitoring device is paired with one or more of the following: pharmaceutical regimens, therapeutic regimens, use of inhaler, use of nebulizer, use of pharmaceutical targeting respiratory system, use of pharmaceutical targeting cardiovascular system, use of pharmaceutical targeting asthma, COPD, CHF, cystic fibrosis, bronchopulmonary dysplasia, pulmonary hypertension, other diseases of the lungs. This embodiment of the device is used to judge the effectiveness of possible medical and nonmedical interventions on respiratory state or respiratory health and suggest changes in regimen for optimization and/or suggest appropriate interventions when the patient is at risk for complications.

In one embodiment RVM is paired with behavioral algorithms or algorithm that includes information about any of the following patient medical status, environmental factors, and behavioral factors of a demographic group or of the patient in general. In a preferred embodiment, one of the algorithms described above could denote the necessity for obtaining an RVM measurement. More preferably, the RVM measurements are used in conjunction with behavioral/medical/environmental algorithmic data to provide information to indicate action or therapy. An example of the use of this embodiment of the device would be an algorithm which includes the patient's previous respiratory complications or chronic respiratory illness, and/or allergies as inputs along with behavioral events known to exacerbate said conditions. By including information from the patient's schedule (e.g. attending an outdoor event during allergy season, or participating in a sporting competition), the system recommends that he take an RVM measurement then makes recommendations about whether to maintain normal dosing of medication or increase it. The software can also recommend that the patient bring medication with him to the event, and generally remind the patient to take his medication. Another example could be that the patient had an asthma attack or other respiratory complication. RVM data could be utilized to assess the severity of this attack by any of the measured parameters including minute ventilation, tidal volume, time for inspiration vs. expiration (i.e. ratio), shape of the respiratory curve during normal breathing, shape of the respiratory curve during the deepest possible breath or other respiratory maneuver. The data could then prompt independently or be used in conjunction with other information to make a decision for the patient to perform an action including one of the following: do nothing, rest, use an inhaler, take a pharmaceutical, use a nebulizer, go to the hospital. Information as to the action required could be part of a behavioral or other algorithm designed for the specific patient or a group of patients with a similar disorder, patients with a similar demographic, patients with a specific medical, anatomic or behavioral profile or patients in general. Preferably, after the action, the patient is instructed to repeat the RVM measurement to assess the adequacy of therapy. Preferably his repeat measurement is compared to the measurement before the therapy or other intervention and changes are noted. Additional information from this comparison or just data taken after therapy is used alone or in combination with other patient data to make further medical decisions or recommendations for action.

For example, an asthmatic is having symptoms and decides to or is instructed by a disease management algorithm to obtain an RVM measurement. The RVM data is analyzed by the device, utilized independently or compared to his historic baseline or the last measurement taken. Based on these, with or without other patient specific inputs such as heart rate, the device recommends he use his inhaler. A second set of RVM data is then taken. The RVM data is compared to the previous RVM data taken prior to treatment. The device then follows a decision tree and tells the patient he has improved and needs no further therapy, that he needs to repeat the dosage, that he needs to call his physician, or that he immediately needs to go to the hospital. In a preferred embodiment, the RVM data is combined with behavioral algorithms developed for a demographic or for a specific patient to optimize recommendations for the patient.

PACU/ICU Usage

In one embodiment, the device is used within a Postoperative Anesthesia Care Unit (PACU) setting, as either a standalone monitor or as an accompaniment to or incorporated in an existing monitor. Within the PACU, RVM volume is calculated and compared against pre-calibrated data derived taking into account BMI, height, weight, chest circumference, and other parameters. The device is used to complement existing quantitative data that supports decision making within the PACU. In one embodiment, within the operating room, RVM data is correlated with end tidal carbon dioxide measurements to provide a more comprehensive assessment of respiratory status. RVM derived measurements including minute ventilation are used to compare a patient's status before, during, and after surgery or a procedure and to document the effect of anesthesia/narcotic induced respiratory depression. RVM is used to support more subjective assessments made by clinicians in the PACU by providing a quantitative justification for certain decisions, including the decision to re-intubate. The device also supports subjective assessment regarding patients on the hospital floor as a monitor for decline in respiratory status and an alarm for the need to re-intubate or perform another intervention to improve respiratory status. Preferably, RVM measurements will assist in regulation of narcotic pain medication, sedative drugs such as benzodiazepines, or other drugs with respiratory depressive effects. In one embodiment, the above mentioned uses regarding the RVM in a PACU setting are implemented within the ICU setting such as a Neonatal ICU, Surgical ICU, Medical ICU, Pulmonary ICU, Cardiac ICU, Coronary Care Unit, Pediatric ICU, and Neurosurgical ICU. In another embodiment, the RVM device is used in the setting of a step down unit or standard hospital bed to follow respiratory status.

Later in the postoperative period or otherwise, measurements of the respiratory pattern, including tidal volumes, respiratory rate, minute ventilation, variability in inter-breath interval or volume, or RVM signal complexity can be compared to baseline values measured before surgery. This can directly aid the extubation decision by defining what is an adequate level of breathing specific to that patient. In another embodiment of the device, RVM monitoring identifies problems that are commonly associated with ventilators, such as poor endotracheal tube positioning, hyperventilation, hypoventilation, rebreathing and air leaks. The system also identifies air leaks through a chest tube or cuffless tube. Air leaks would cause a downward trend to appear on any direct volume measurement which would not be present on the impedance trace, thus the device can detect and report air leaks in devices which directly measure volume or flow. In a preferred embodiment, the system identifies abnormalities and trends specific to a hemithorax such as those related to the following pathologies: pneumothorax, pulmonary contusion, rib fractures, hemothorax, chylothorax, hydrothorax, and pneumonia.

In one embodiment, the device is used during Monitored Anesthesia Care (MAC) to monitor respiratory status, assist in drug and fluid administration, provide indication of impending or existing respiratory compromise or failure, and assist in the decision to intubate if necessary.

In another embodiment of the device, RVM monitoring identifies problems that are commonly associated with ventilators, such as poor endotracheal tube positioning, hyperventilation, hypoventilation, rebreathing and air leaks. In one embodiment RVM measurements are combined with data derived from the ventilator to provide additional data regarding physiology. An example of this is that differences can be recorded in RVM measurements vs. inspired or expired flows or volumes measured on the ventilators to assess "work of breathing" in a quantitative fashion.

In another embodiment, RVM measurements are taken after surgery in a patient who is still under the effects of anesthesia or pain medication to monitor patient recovery. Recording a baseline tidal volume curve for a patient during normal preoperative conditions provides a comparison baseline for monitoring during and after surgery. Returning to a similar tidal volume curve is one signal of respiratory recovery after being taken off a ventilator. In this embodiment of the invention, the device is used to evaluate the success of extubation and determine if reintubation is necessary. The invention described herein allows these measurements to be taken noninvasively and without being in the stream of inspired/expired air or impeding airway flow or contaminating the airway circuit.

In one embodiment, the device is used within outpatient surgical centers, specifically geared towards patients receiving Monitored Anesthesia Care, including patients undergoing orthopedic procedures, cataract surgery and endoscopy of the upper and lower GI tract.

Diagnostic Usage

In one embodiment, the device is used to quantify respiratory parameters during performance based tests. In a preferred embodiment, the device is used to quantify respiratory parameters in tests of cardiovascular function including stress tests. In a preferred embodiment, the device is used in combination with one of the following tests to assess impact of the test on respiration. In a preferred embodiment, the device reports effects of exercise or a particular drug like dopamine on the overall physiology or metabolism of the body as reflected by changes in respiratory volumes, patterns, rate or combinations thereof including advanced analysis of breath-to-breath variability/complexity, fractal or entropy based analyses as described elsewhere. In a preferred embodiment, the device is used to evaluate the safety of a given level of exercise or pharmacologic stress.

In a preferred embodiment, variability or complexity analysis of RVM measurements is undertaken in concert with standard pulmonary function testing. In a preferred embodiment, variability or complexity analysis of RVM measurements is undertaken with or without heart rate variability/complexity analysis in concert with standard cardiovascular physiology testing such as stress testing, walking tests for claudication, or other performance based testing.

In a preferred embodiment, the device is used to evaluate the effects of drugs on the respiratory system including bronchodilators for diagnostic purposes, monitoring of therapeutics, optimization including effects on both heart and lungs. More preferably, the device above combines respiratory information obtained by impedance or other methods described with EKG information about heart rate, heart rate variability, EKG evidence of ischemia or arrhythmia. In a preferred embodiment, the device is used to evaluate the effects of bronchoconstrictors as in a provocative test. In various embodiments, the device obtains continuous or intermittent RVM measurements. In a preferred embodiment, the device provides trending of RVM data.

In a preferred embodiment, the device is used to evaluate the effects of metabolic stimulants, cardiovascular drugs including beta blockers, alpha adrenergic agonists or blockers, beta adrenergic agonists or blockers. In a preferred embodiment, the device is used during a stress test to demonstrate level of effort placed or to demonstrate an unsafe condition relative to the pulmonary system to terminate or modify the test. Stress Introduced to the patient is created by various means including but not limited to, exercise and/or the delivery of a drug. In a preferred embodiment, the device indicates or works with other technologies described earlier to indicate the level of overall exercise. In a preferred embodiment, the device is used as a free-standing device for measuring the effects of exercise or other stimulant on the pulmonary system.

In another embodiment of the device, the respiratory information is combined with cardiac information to define the level of exertion related to EKG changes associated with cardiac disease. In another embodiment of the device, the system combines respiratory information with cardiac information to determine the level of exertion of an athlete.

In another embodiment, the device provides warning of potential negative impact of the level of exercise on overall health or on cardiac status, with or without pairing respiratory signals with cardiac impedance or EKG measurements in the home, athletic field, military environment or out of hospital setting. One embodiment of the device is a holter monitor which outputs values for one or more of the following: respiratory effort, level of activity, state of physiology, or metabolism associated with different rhythms, depolarization or other cardiac pathophysiology.

One embodiment of the invention is similar to a holter monitor which monitors one or more physiological parameters over hours to days in a hospital, home, or other setting. One embodiment of the device is combined with a holter monitor or critical care monitor which specifically monitors decompensation effects related to heart failure. A similar embodiment of the device monitors and outputs measurements of "lung water". In one embodiment, the device is included in a disease management system for congestive heart failure.

In a most preferred embodiment, the device provides a continuous measurement which can be run for long periods of time and can deliver a time curve demonstrating the effects of exercise or a drug for diagnosis, therapeutic monitoring or drug development.

One embodiment of the device provides trending data over minutes to hours to days for patients with a variety of disease states including chronic obstructive pulmonary disease, congestive heart failure, pulmonary hypertension, pulmonary fibrosis, cystic fibrosis, interstitial lung disease, restrictive lung disease, mesothelioma, post thoracic surgery, post cardiac surgery, post thoracotomy, post thoracostomy, post rib fracture, post lung contusion, post pulmonary embolus, cardiac ischemia, cardiomyopathy, ischemic cardiomyopathy, restrictive cardiomyopathy, diastolic cardiomyopathy, infectious cardiomyopathy, hypertrophic cardiomyopathy. Preferably the device provides information about changes in respiration in these disease states related to interventions or provocative testing procedures.

In one embodiment of the device of the invention, the system is used to diagnose various diseases. In a preferred embodiment, the device is used to assess the risk of developing pneumonia. In another embodiment, the device is used to assess the risk that a pneumonia therapy is not effective, and suggest corrective action. Another embodiment of the invention is used for the evaluation of functional deterioration or recovery associated with diseases including but not limited to: pneumonia, heart failure, cystic fibrosis, interstitial fibrosis, hydration levels, congestion due to heart failure, pulmonary edema, blood loss, hematoma, hemangioma, buildup of fluid in the body, hemorrhage, or other diseases. This information may be used for diagnosis as above or be integrated with respiratory volume measurements or other physiological measurements that may be measured by the device or input into the device to provide a comprehensive respiratory sufficiency index (cRSI).

In one embodiment, disease specific modules can be created to gather disease specific information, employ disease specific algorithms and deliver either optimized respiratory volume data or respiratory diagnostic data related to the specific disease. In a preferred embodiment of the invention, respiratory curve analysis is used to diagnose medical conditions. In one embodiment, the system utilizes provocative tests to determine measurements or estimates of one or more of the following: tidal volume, residual volume, expiratory reserve volume, inspiratory reserve volume, inspiratory capacity, inspiratory vital capacity, vital capacity, functional residual capacity, residual volume, forced vital capacity, forced expiratory volume, forced expiratory flow, forced inspiratory flow peak expiratory flow, and maximum voluntary ventilation. In this embodiment, diagnostic tools such as flow volume loops are generated by software running on the system for diagnosis of various cardiopulmonary or other disorders.

Respiratory curve analysis can also be used to assess cardiopulmonary or other disorders without provocative tests. In one embodiment, an algorithm monitors trends in TV, MV and RR to provide a metric of respiratory sufficiency or respiratory sufficiency index (RSI). In another embodiment, an algorithm analyzes individual breaths as an input to diagnose respiratory conditions. In this embodiment, one or more of the following parameters are calculated on a breath by breath basis: inspiratory time ($I_t$), expiratory time ($E_t$), $I_t$:$E_t$ ratio, percent inspiratory time, tidal impedance, tidal volume and area under the curve. In this embodiment, the various parameters are outputted through the system's user interface or printable report for the user to assess respiratory disease state. In a preferred embodiment, an algorithm analyzes the parameters to act as a diagnostic aid. In this embodiment, the system outputs an index of disease severity or a positive/negative reading for the disease.

In one embodiment, the device is implanted. In a preferred embodiment, the device is powered from a pacemaker-like battery. In one embodiment the device is combined with a pacemaker or defibrillator. In one embodiment the device is adjusted or calibrated or interrogated using an external component.

Figure 40:
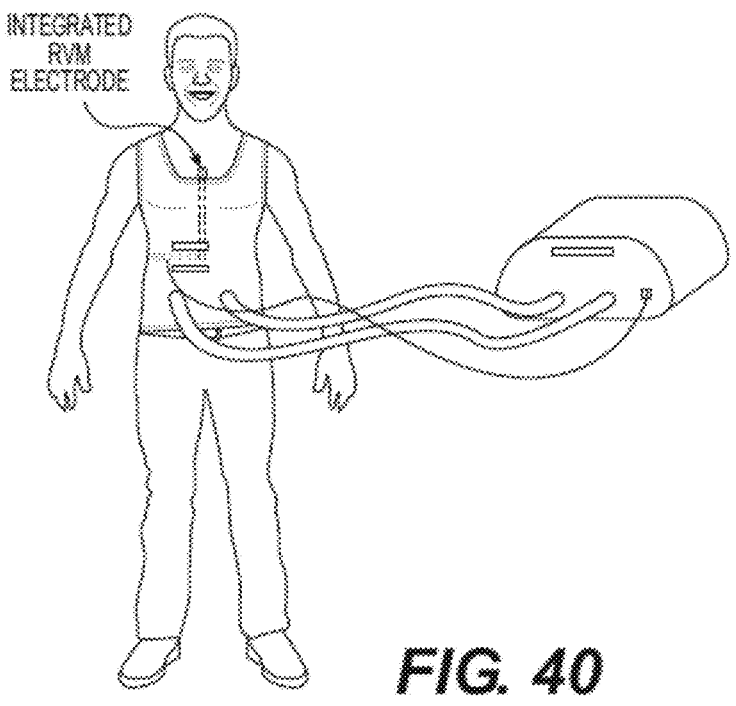
FIG. 40 depicts an embodiment of the invention wherein the impedance measuring device is in data communication with a HFCWO vest.

FIG. 40 depicts an embodiment of the invention wherein the impedance measuring device is in data communication with a High-Frequency Chest Wall Oscillation ("HFCWO") vest. It has recently been observed that during vest oscillation therapy, the Minute Ventilation of a patient is reduced by up to 50%. The improvement in efficiency may provide significant health benefits for a patient who is having difficulty providing oxygenation of their bloodstream during breathing. In a preferred embodiment, the HFCWO vest automatically provides therapy levels (frequency, intensity, length) which have been developed to optimize the O2 to CO2 transfer in the lungs. The goal is to optimize the oxygen and CO2 transfer by the use of the HFCWO vest. By increasing the turbulence in the lungs during inhalation and exhalation better oxygen and CO2 transfer can be achieved. Preferably, a decrease in work of breathing decreases the chance of respiratory failure. In addition, patients who are receiving oxygen therapy could combine the oxygen therapy with the HFCWO vest therapy to maximize oxygenation, improve CO2 removal and decrease work of breathing, thereby preferably extending life.

Typically, HFCWO vest therapy provides for a 10 min treatment to eliminate exudate. The use of this product preferably allows for better oxygenation. The use of the product could be continuously up to 24 hrs/day. The system could be customized to activate when the patient requires the additional oxygenation efficiency, e.g. during active times such as walking. As opposed to exudate removal the parameters of oscillation could be optimized to minimize patient discomfort while maximizing oxygen transfer in the lungs.

As shown in FIG. 40, a sensor for acquiring a physiological bioelectrical impedance signal from the patient is preferably functionally connected to a computing device. The computing device preferably analyzes the physiological bioelectrical impedance signal, and provides an assessment of minute ventilation and tidal volume of the patient based on the analyzed bioelectrical impedance signal. The computing device also preferably monitors the signal over time and provides a signal to the HFCWO vest.

Preferably, the HFCWO vest automatically adjusts therapy levels (frequency, intensity, length) based on the levels of physiologic parameters including tidal volume, minute ventilation, and respiratory rate during therapy as determined by the computing device. In addition, the general session-to-session lung performance can be tracked (TV, RR, MV) to demonstrate effectiveness of the therapy and the need to extend or modify the therapy levels. The goal is to optimize the oxygen and CO2 transfer by the use of the HFCWO vest to increase the turbulence in the lungs during inhalation and exhalation.

In addition, the shape of the bioimpedance exhalation/inhalation curve can be an indicator of the success of the therapy. Appropriate curves for maximizing oxygen transfer can be identified and the levels of the HFCWO vest (frequency, intensity, length of therapy, Baseline compression) can be adjusted to get the desired respiratory curve and necessary oxygenation and/or CO2 extraction and to minimize the work of breathing.

Additionally a pulse oximeter can be added to the system as an indicator of the success of the enhanced compression therapy and improved oxygenation. The levels of therapy can be optimized by watching the oxygenation response over time. CO2 monitoring can be added to the system with either end tidal or transcutaneous CO2 monitoring. In addition patients who are receiving oxygen therapy could combine the oxygen therapy with the HFCWO vest therapy to preferably maximize oxygenation, improve CO2 removal, decrease work of breathing, and extend life.

Figure 41:
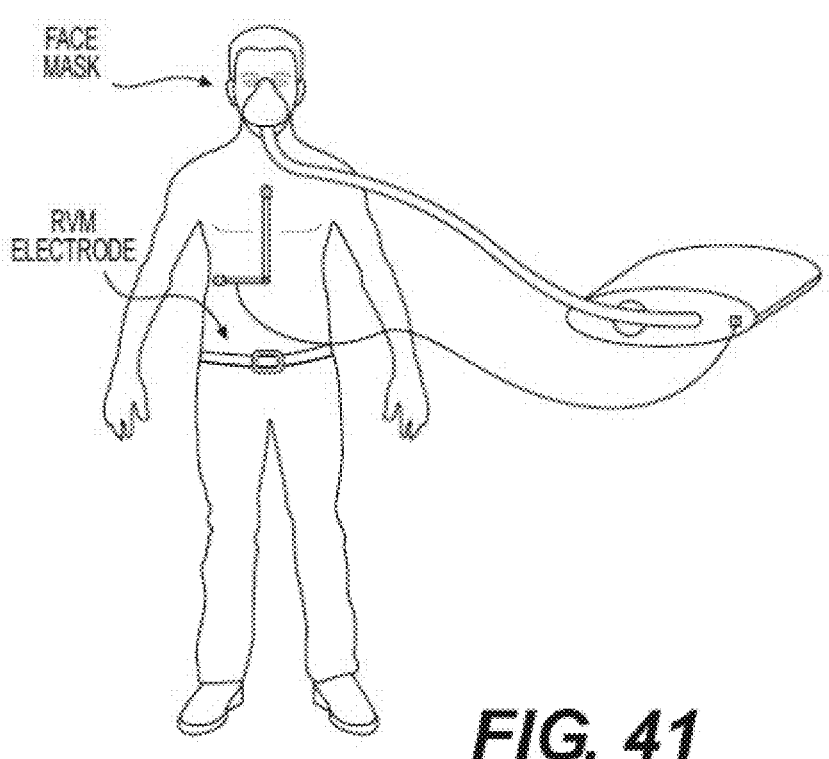
FIG. 41 depicts an embodiment of the invention wherein the impedance measuring device is in data communication with a mechanical ventilation therapy device.

FIG. 41 depicts an embodiment of the invention wherein the impedance measuring device is in data communication with a mechanical ventilation therapy device. The mechanical ventilation therapy device may be a CHFO system, a ventilator, a CPAP, a BiPAP, a CPEP (Continuous Positive Expiratory Pressure), High-flow O$_2$ device, or another non-invasive ventilation device. Preferably, the system includes a sensor for acquiring a physiological bioelectrical impedance signal from a patient and is functionally connected to a computing device. The computing device preferably analyzes the physiological bioelectrical impedance signal and outputs an assessment of minute ventilation and tidal volume of the patient based on the analyzed bioelectrical impedance signal. The system may also monitor the signal over time and provide a signal to the mechanical ventilation device. The mechanical ventilation device preferably causes better oxygenation efficiency in the lungs. The mechanical ventilation device preferably can adjust the frequency, intensity, of the oscillations and/or the base line inhalation and exhalation pressures.

A bioelectric feedback signal provides indication for the success of oxygenation. The characteristic values for tidal volume, minute volume, and respiratory rate will change. By monitoring the change, the system can automatically adjust the mechanical ventilation device's parameters to optimize physiological response and the efficiency of the system. Additionally a pulse oximeter can be added to the system as an indicator of the success of the mechanical ventilation therapy. Improved oxygenation and CO2 transfer can preferably be achieved or a decrease in work of breathing can preferably be achieved to decrease the chance of respiratory failure. The levels of therapy can be further optimized by watching the oxygenation response over time. In addition, the overall length of therapy can be adjusted. The general session-to-session lung performance can be tracked (TV, RR, MV) to demonstrate effectiveness of the ventilation and the need to extend or modify the therapy levels.

In addition, the characteristic shape of the bioimpedance inhalation and exhalation curve is an indicator of the success of the therapy. By tailoring the therapy to get the desired expulsion curve, the system can optimize oxygenation efficiency. Appropriate curves for maximizing ventilation can be determined and the adjustment levels of the Ventilator (frequency, intensity, length of therapy, Baseline Pressure) can be adjusted to get the desired respiratory curve. In addition, patients who are receiving oxygen therapy could combine oxygen therapy with mechanical ventilation therapy to maximize oxygenation and extend life. Additionally, the level of compliance to using the system and getting the adequate therapy can be monitored by analyzing the volume of air coming in and out of the lungs.

By using the Tidal Volume, MV, and RR the relative success of opening up the airways can be determined.

Mechanical ventilation therapy can be combined with aerosol delivery to provide an additional therapy regimen. As the aspiration of aerosol will inherently modify the impedance characteristic of the lung, the level of respiration and the effect of these two combined treatments can also be optimized. For example during the treatment the Tidal Volume and the characteristic inhalation and expulsion curves can be monitored before, during, and after treatment to ensure appropriate optimization of the positive expiratory pressure on expansion of the lung and airways or an adequately cleared lung.

Figure 42:
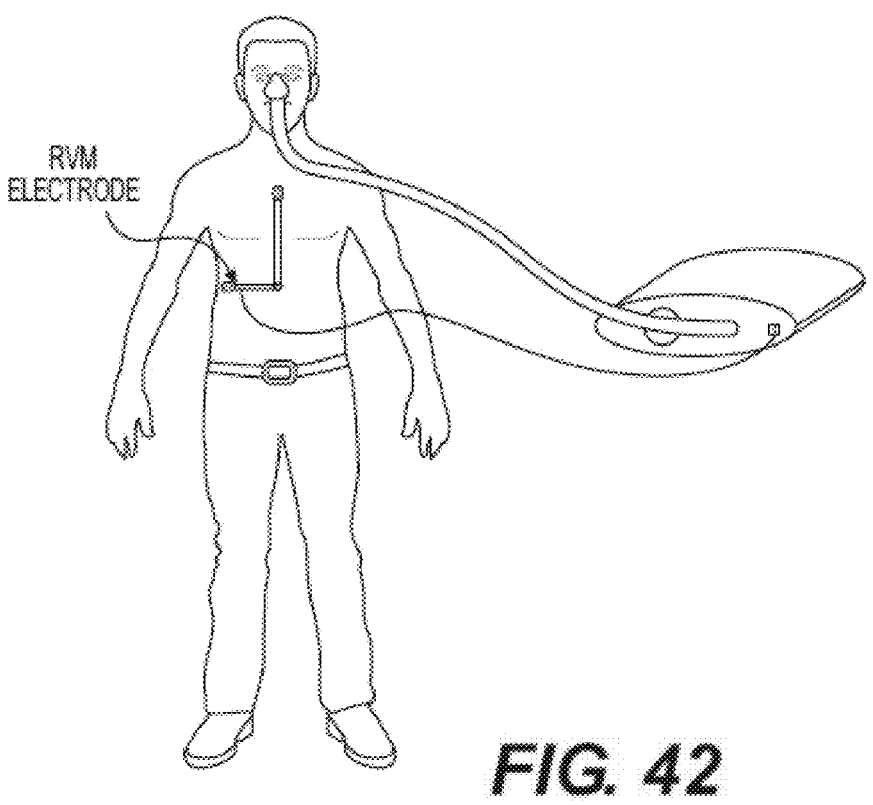
FIG. 42 depicts an embodiment of the invention wherein the impedance measuring device is in data communication with a oxygenation therapy device.

FIG. 42 depicts an embodiment of the invention wherein the impedance measuring device is in data communication with an oxygenation therapy device. The system preferably includes a sensor for acquiring a physiological bioelectrical impedance signal from a patient and is functionally connected to a computing device. The computing device preferably analyzes the physiological bioelectrical impedance signal and provides outputs an assessment of minute ventilation and tidal volume of the patient based on the analyzed bioelectrical impedance signal. The computing device additionally preferably monitors the signal over time and provides a signal to an oxygen therapy system. Preferably, the oxygen therapy provides oxygen via a mask or nose cannula. The bioelectric feedback signal provides indication for the success of the level of the expansion of the airways. The characteristic shape of the bioimpedance expansion curve is an indicator that the air is getting into the lungs.

By combining the pressure monitoring of the inhalation and exhalation with the impedance signal, the oxygenation therapy system can synchronize the delivery of oxygen to the cannula to ensure optimal oxygen uptake through the nose cannula.

For oxygen therapy using a mask, the feedback mechanism of the oxygen delivery can be optimized as well. In addition, by using both the impedance signal as well as the mask pressure, the oxygen system can more reliably determine how well the mask is applied to the patient and how well the circuit is maintained (kink free and leak free).

Figure 43:
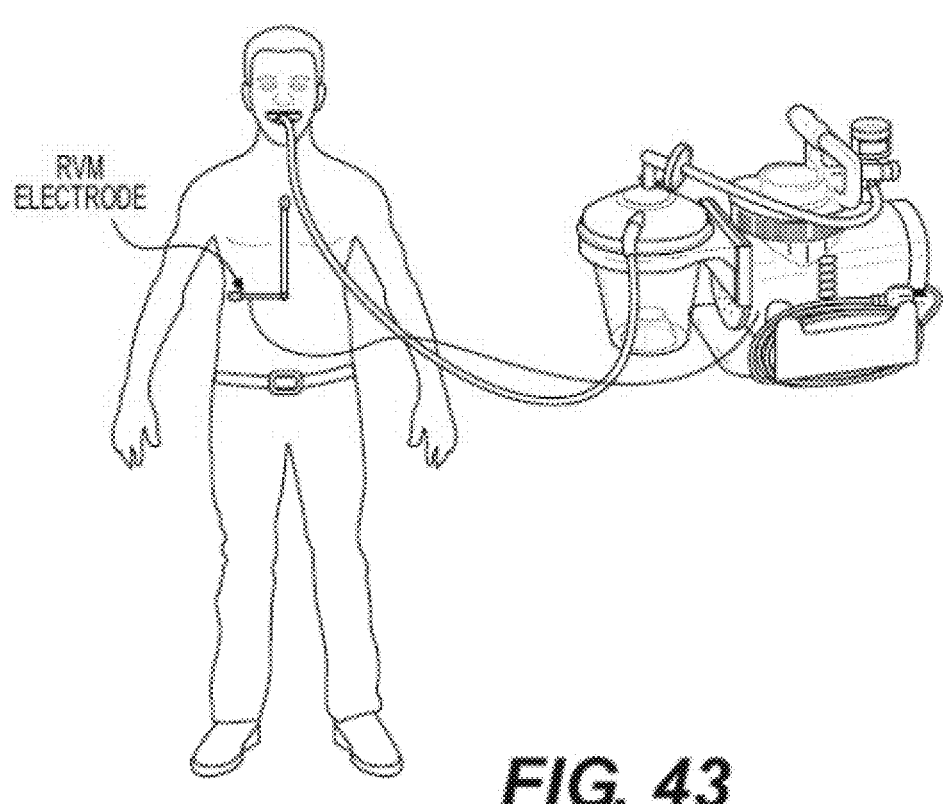
FIG. 43 depicts an embodiment of the invention wherein the impedance measuring device is in data communication with a suction therapy device.

FIG. 43 depicts an embodiment of the invention wherein the impedance measuring device is in data communication with a suction therapy device. The system preferably includes a sensor for acquiring a physiological bioelectrical impedance signal from a patient and is functionally connected to a computing device. The computing device preferably analyzes the physiological bioelectrical impedance signal and provides an output of an assessment of minute ventilation and tidal volume of the patient based on the analyzed bioelectrical impedance signal. The computing device preferably also monitors the signal over time and provides a signal to the suction therapy device.

Suction therapy preferably causes the mobilization of fluid in the lungs. The suction therapy can be adjusted for frequency and intensity of the oscillations. Also, the base line inhalation and exhalation pressures can be adjusted and the overall length of therapy can be adjusted.

The bioelectric feedback signal preferably provides an indication for the success of the mobilization of secretions. As the suction draws fluid, the characteristic values for tidal volume, minute volume, and respiratory rate will change. By monitoring the change, the system can preferably automatically adjust the suction parameters to optimize physiological response.

In addition the characteristic shape of the bioimpedance expulsion curve is an indicator of the success of the therapy.

By tailoring the therapy to get the desired expulsion curve the system can optimize the mobilization of fluid from the patient.

Fluid clearance can be combined with aerosol delivery to provide another therapy regimen. As the aspiration of aerosol will inherently modify the impedance characteristic of the lung, the level of respiration and the effect of these two combined treatments can also be optimized. For example during the treatment the tidal volume and the characteristic inhalation and expulsion curves can be monitored before, during, and after treatment to ensure appropriate outcome of an adequately cleared lung.

Figure 44:
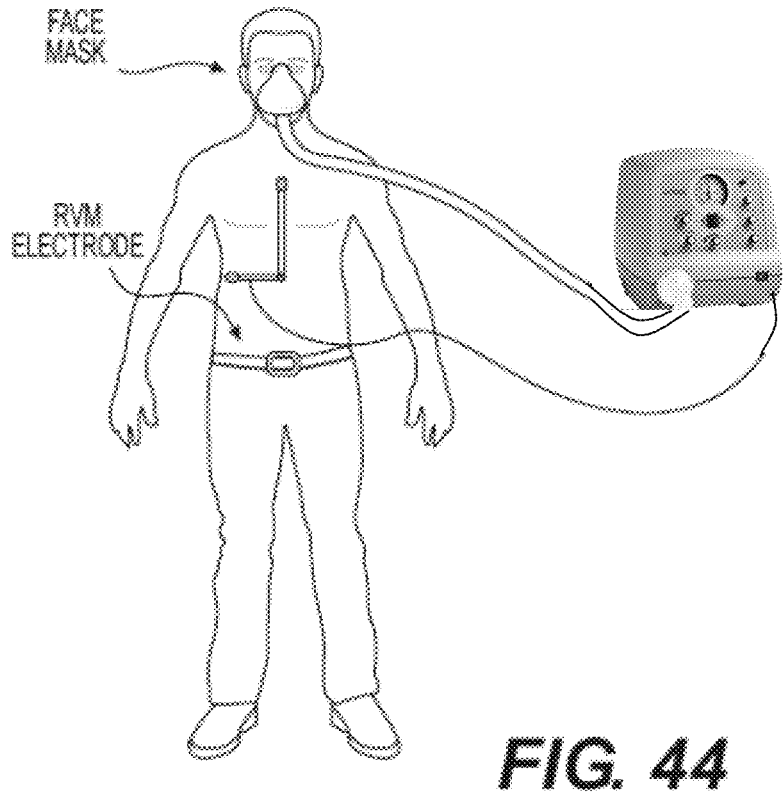
FIG. 44 depicts an embodiment of the invention wherein the impedance measuring device is in data communication with a cough assist device.

FIG. 44 depicts an embodiment of the invention wherein the impedance measuring device is in data communication with a cough assist device. The system preferably includes a sensor for acquiring a physiological bioelectrical impedance signal from a patient and is functionally connected to a computing device. The computing device preferably analyzes the physiological bioelectrical impedance signal and provides an output of an assessment of minute ventilation and tidal volume of the patient based on the analyzed bioelectrical impedance signal. The computing device preferably also monitors the signal over time and provides a signal to the cough assist device.

The cough assist device is preferably a non-invasive therapy that stimulates a cough to remove secretions in patients with compromised peak cough flow. It is designed to keep lungs clear of mucus. Retained secretions collect in the lungs, creating an environment for infection. Mechanical Insufflation/Ex-sufflation (MI/E) therapy products are important for patients who have weakened cough and are unable to remove secretions from the large airways without assistance. The system supplies positive pressure (inhale) to inflate the lungs, then quickly shifts to supply negative pressure (exhale), during this process secretions are sheared and can be expectorated or removed with suction. After the exhale, the system pauses and maintains a resting positive pressure flow to the patient. A facemask or mouthpiece can be used on endotracheal and tracheostomy (i.e. for patients with an appropriate adapter).

Preferably, the cough assist device automatically adjusts characteristic therapy levels (frequency, intensity, length of therapy, inhalation pressure, exhalation pressure) based on the levels of tidal volume, minute ventilation, and respiratory rate during therapy. In addition, the general within session and the session-to-session lung performance can be tracked to demonstrate effectiveness of the therapy (before, during, and after and across many sessions). Graphs could be provided to document breathing characteristics of the patient and to demonstrate improvement to the patient over time.

In addition, the characteristic shape of the bioimpedance expansion curve is an indicator of the success of each individual cough. Appropriate curves for maximizing exudate removal can be identified and the adjustment levels of the Cough assist System (frequency, intensity, length of therapy, inhalation pressure, and exhalation pressure) can be adjusted to get the desired cough expulsion curve. Characteristics of the cough assist can be adjusted to ensure the optimal results are provided for each individual patient.

Device and Method for Clinical Evaluation

Step 1: Most studies look at events over a given time period in total, i.e. events over a hospitalization or over 30 days and then look at what influences that overall event rate. It is important to look more closely to minimize the number of patients needed to study to get a meaningful result.

Step 2: To use a measurement or a group of measurements collected to stratify patients into who will have an event after the diagnosis or stratification is made, (diagnostic or stratification event) then instead of looking at an extended period of time, looking at small defined time segments can be helpful in understanding the impact of the event and importantly can help understand if the "event" is real or not.

In one embodiment, this is described as events/hour for every hour after the stratification event. Understanding the time interval for analysis can be decided based on standard medical/clinical principles or by querying the data with machine learning (AI) or other computerized techniques to determine the best interval for such analysis. The duration of the interval may also be varied according to time after a diagnostic or stratification event, either continuously or discontinuously. For example, if a patient has low blood pressure in the OR, the patient would have a higher likelihood of having positive troponins postoperatively. However, the positive troponins would mostly be soon after surgery and not 3 days later, as such positive troponins would likely not be related to the hypotension in the OR. Therefore, it is desirable to look at positive troponins at each hour after the episode of hypotension.

In another example, if a patient has low minute ventilation (hypoventilation, i.e. respiratory depression) the last half hour in the recovery room (PACU) then it is statistically more likely that the patient will have low minute ventilation (LowMV) postoperatively. In such as case, the LowMV postop is most prominent in the first 12 hours after surgery in a group that had LowMV the last half hour in the PACU, with some increased events extending until 48 hours, and rare LowMVs in groups that had no LowMV the last half hour of the PACU.

For pulse oximetry, the situation is different. For example, in a group that has LowMV the last half hour in the PACU, the rate of desaturation/hour occurs somewhat uniformly across the 48 hour period. Alternatively, for patients with no LowMV the last half hour in the PACU, there is almost no desaturation until the second day with a maximum desaturation around 30 hours. Because this seems unlikely, such a temporal division of the data in hourly increments over time after PACU discharge may be used to help validate or invalidate the recorded desaturation as being true. It would be unlikely that 12% of all patients would have desaturation at 30 hours. So the qualification of the desaturation as a true alarm can take into account the time passed since PACU discharge.

Pairing the two measurements may also help qualify the "true alarm" status of pulse oximetry with minimal possibility for the development of significant hypoxia over a short or moderate period of time (as opposed to baseline hypoxia from cardiac or pulmonary disease). It is highly unlikely that a patient would have significant hypoxia without a significant change in ventilation. If the patient has respiratory depression and hypoventilation, then desaturation will likely follow with a speed commensurate to the degree of hypoventilation. If the patient becomes hypoxic from a pulmonary embolus (very rapidly) or heart failure (more slowly) then the patient will likely try to compensate with hyperventilation. If the lungs are compliant, as in COPD, then the hyperventilation will likely be more related to increase in TV than RR. If the lungs are stiff, as with CHF, then the hyperventilation will likely be more related to an increase in RR than TV.

Step 3: Consider on a per patient basis over time.

In one embodiment, preferably one calculates the number of patients with x events per hour, as opposed to events per hour, and then uses the calculation either to qualify the data or to define the timeframe for patients having events after the stratifying event. For example, if there were 5 events in hour 2 it could be 5 events for one patient or 1 event for 5 patients, which would have a different impact for both the individual patient and also the way the measurement itself might be evaluated or qualified.

Step 4: Consider the time frames before and after the time frame of interest.

In one embodiment, if there are events the contiguous hours before and/or after the hour of interest, it is preferably considered that this is a prolonged episode versus if there are events in two separate hours during the overall course. Such consideration preferably has a different impact for both the individual patient and also the way the measurement itself might be evaluated or qualified. Understanding how long or how many timeframes (or hours) might be considered could be chosen by looking at the overall range of duration of an event. Understanding the "long duration" events and number of such events could be determined either by discontinuous clustering of time frames or by other means of separation. See, for example, the blobbiness index. The actual incidence of long duration events could be then looked at in terms of time since stratification event.

Step 5: The time course of each patient after the stratification event across the entire time frame could be used with the temporal component of the course used as a separate variable to assist in both analysis of the individual patient and a way to better qualify or understand the measurement itself.

Multiple variables and time of presentation of such variables from an initial stratification or diagnostic event may help define "true" vs "false" measurement status. Continuous or intermittent measurements can include minute ventilation (mV, TV, RR), temperature (peripheral, core), arterial blood pressure (systolic, diastolic, mean), cardiac output (Heart rate, stroke volume) oxygen saturation (oxyhb, deoxyhb, pulse rate), CO2 (end tidal, transcutaneous), EKG (heart rate, arrhythmia), and with a different time constant. The initial time point of stratification or diagnosis could, for example, be determined by presentation of a patient, change in patient location, values of any physiologic, clinical or laboratory parameter or test.

In some embodiments one looks at the variables as separate in certain measurements. Time and frequency domain analysis of these parameters' signals can be used to remove artifact and have more accurate measurements. Preferably, one looks at oxy and deoxy hemoglobin separately instead of combined in an oxygen saturation (oxy/oxy+deoxy) measurement. This has been problematic in terms of total hemoglobin in a given sample being detected and technologies that try to measure total hemoglobin have had issues doing so. However, looking at trending and changes in data has proven more useful. Evaluating the change of oxy and deoxy hemoglobin with respect to each other, the ratio of change and/or time frame in which the change occurs, will validate the "true" and "false" oxygen saturation and total hemoglobin measurements.

In qualifying any measurement as "true" preferably one looks at the measurement in the context of patient condition in general and in terms of the timeframe after a stratifying event in particular. In one embodiment, if one wants to qualify a pulse ox reading as true and not related to an artifact of motion or of lack of perfusion systemically or due to pressure on the probe or other issues, then the amount of total hemoglobin or using oxy and deoxyhemoglobin as independent variables can determine the appropriateness of the measurement. Over time, the time course of the change in total hemoglobin, or oxy hemoglobin or deoxyhemoglobin, either independently or in some combination, could help qualify a measurement as true or provide a level of confidence around the measurement. In another embodiment, or in combination with the above, in qualifying any measurement as "true" we can use the change or a change in the change (acceleration, second derivative) or variability or change in variability. Other measurements such as a change in minute ventilation, tidal volume and/or respiratory rate or end tidal CO2 or transcutaneous CO2 would be expected to be associated, either before or after a changed in oxygen saturation, and the timing of the change in the other parameters or the slope of the change or variability of those measurements or other features of the change in those measurements could be used to qualify the "true" nature of the pulse oximeter data. One would expect gradual or acute respiratory depression to cause a decrease in minute ventilation, tidal volume and/or respiratory rate in advance of pulse oximeter changes. One would expect a "true" change in oxygen saturation gradually with congestive heart failure or other diffusion gradient in the lungs from sepsis or renal failure or volume overload. This can be differentiated from other causes of hypoxia by any of the following—increased RR vs TV, increase in MV and time course of occurrence, time frame of occurrence since diagnostic or stratifying event, etc.

One would expect a "true" change in oxygen saturation gradually with COPD or other circumstance with compliant lungs with poor capacity to oxygenate to cause a decrease in minute ventilation, tidal volume and/or respiratory rate in advance of pulse oximeter changes. One would expect a "true" change in oxygen saturation gradually with COPD decompensation or other similar pathology in the lungs with compliant lungs to be differentiated from other causes of hypoxia by any of the following—increased TV vs RR, increase in MV and time course of occurrence, time frame of occurrence since diagnostic or stratifying event, etc.

A mixture of pathologies could lead to the above physiologic measurements that would carry features of both pathologies such as increases in both TV and RR with hyperventilation (increase in MV). While such determinations might be made with an unsupervised algorithm or AI system, by segmenting time and important variables along physiologic or clinical lines, fewer data points are required to evaluate a measurement or the effects of a therapeutic or other factor on a measurement.

In another embodiment, the adequacy of a sepsis score or indicator could be better evaluated by looking at the time course of the presentation of the sepsis vs the time that the stratification or diagnosis occurred. For example, if sepsis was determined to develop 48 hours after a "score" then it was less likely to be related to the score than if it developed 2 hours after the score.

Another embodiment of the invention is directed to systems and methods that diagnose and/or stratify patients by taking in data from various physiological parameters, demographics, clinical events, treatments, lab test results using supervised and unsupervised learning techniques including but not limited to machine learning, Bayesian inference networks, expert systems, principal component analysis, support vector machines, time series forecasting and analysis, fractal analysis, statistical techniques, heuristic algorithms, deep temporal continuous and discontinuous clustering that integrates dimensionality reduction and temporal clustering into a single end-to-end learning framework, maximum margin temporal clustering, fuzzy logic, and neural networks.

Inputs to this system and method can include, but are not limited to:

Minute ventilation (MV) and/or % of predicted MV

Tidal volume (TV)

Respiratory rate (RR)

Ventilation flow-volume relationship

Peripheral blood oxygen saturation (SpO2, hemoglobin, including oxyhemoglobin and deoxyhemoglobin)

Mixed venous oxygen saturation (SvO2)

End-tidal carbon dioxide (EtCO2)

Sublingual and/or transcutaneous CO2

Body temperature (including core and surface temperatures)

Cardiac Output (CO, including stroke volume and pulse rate)

Cardiac index

Perfusion

Blood pressure (BP, including both systolic, diastolic and mean)

Heart Rate (HR)

Electrocardiogram (ECG, heart rate variability, arrhythmia, heart rate)

Renal fluid volumes and rates

Pain level scores and locations

Medication information

Patient location (acuity of care)

Present and prior patient diagnoses and stratification of risk based on different clinical evaluation techniques Temporal and ratiometric relationships of parameter measurements with respect to patient locations Variation and rate of variation of any of the above parameters and/or their components Temporal and ratiometric relationships of all of the above parameters A heuristic algorithm can be developed based on human knowledge, studying clinical data, interactions with clinical staff, and iteration between these steps to make decisions for diagnosis and stratification of patients.

Another embodiment can be developed to learn from an existing database to build a-priori knowledge to make inference decisions to determine the stratification or diagnosis of the patient. The system will preferably continue to adapt its a-priori knowledge based on new patient data, for example from sources listed herein, to continually update the stratification and diagnosis decisions of the patient. Sensitivity analysis may be done to determine the inputs to the system to make decisions for each diagnosis or stratification type. A complete set or subset of inputs associated with each diagnosis or stratification type can be used to train the system and also be used in real-time to diagnose or stratify patients.

Moreover, another system can be developed that is a combination of the previously mentioned heuristic algorithms and machine learning systems in order to diagnose and stratify patients.

Decisions, diagnoses and stratifications include, but are not limited to:

Sepsis

Congestive heart failure

Hypovolemia

Hypertension (systemic and/or pulmonary)

COPD (emphysema, fibrosis)

Pulmonary embolism

Renal failure

Respiratory depression

Respiratory failure

Hypoxia

Changes in metabolism

Stratification of risk to develop the above conditions

Stratification of acuity of care necessary for each patient

Figure 45:
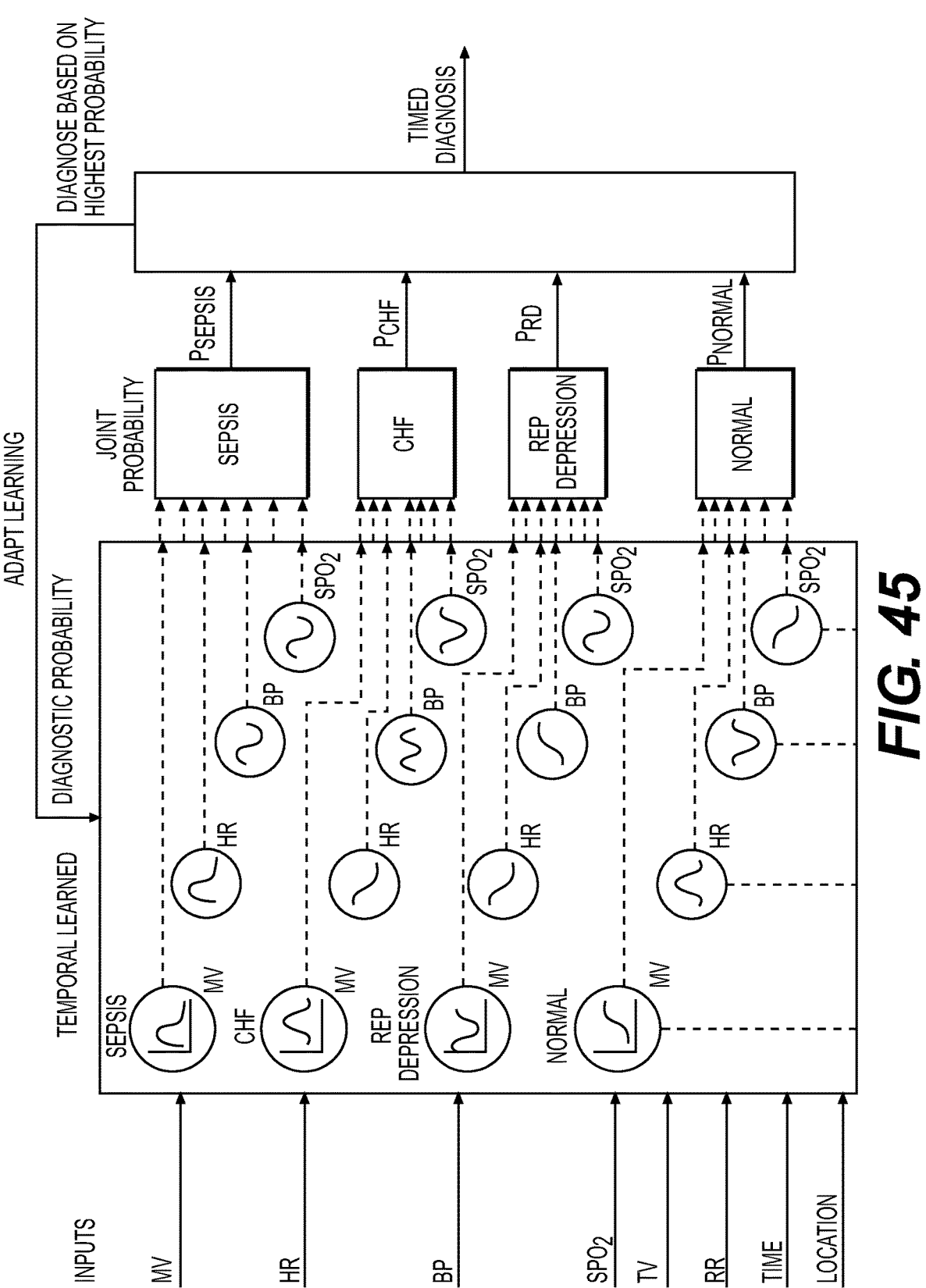
FIG. 45 depicts an example of a Bayesian inference system for a subset of inputs and a subset of diagnoses.

FIG. 45 depicts an example of a Bayesian inference system for a subset of inputs and a subset of diagnoses.

In another embodiment, systems and methods that take in data in the form of various physiological parameters, demographics, clinical events, treatments, lab test results using supervised and unsupervised learning techniques and methods (including but not limited to machine learning, Bayesian inference networks, expert systems, principal component analysis, support vector machine, time series forecasting and analysis, fractal analysis, statistical techniques, heuristic algorithms, deep temporal continuous and discontinuous clustering that integrates dimensionality reduction and temporal clustering into a single end-to-end learning framework, maximum margin temporal clustering, fuzzy logic, and neural networks) in order to qualify alarms from various monitoring technologies as "true" or "false". Rather than reporting all alarms from each monitor, the system's smart algorithm can label alarms as "false" so as to reduce the increasing number of false alarms sounded by individual monitors, while reinforcing "true" alarms using orthogonal monitoring data to confirm status of alarms.

Inputs can include, but are not limited to:

Minute ventilation (MV) and/or % of predicted MV

Tidal volume (TV)

Respiratory rate (RR)

Ventilation flow-volume relationship

Peripheral blood oxygen saturation (SpO2, hemoglobin, including oxyhemoglobin and deoxyhemoglobin)

Mixed venous oxygen saturation (SvO2)

End-tidal carbon dioxide (EtCO2)

Sublingual and/or transcutaneous CO2

Body temperature (including core and surface temperatures)

Cardiac Output (CO, including stroke volume and pulse rate)

Cardiac index

Perfusion

Blood pressure (BP, including both systolic, diastolic and mean)

Heart Rate (HR)

Electrocardiogram (ECG, heart rate variability, arrhythmia, heart rate)

Renal fluid volumes and rates

Pain level scores and locations

Medication

Patient location (acuity of care)

Present and prior patient diagnoses and stratification of risk based on different clinical evaluation techniques Temporal and ratiometric relationships of parameter measurements with respect to patient locations Variation and rate of variation of any of the above parameters and/or their components Temporal and ratiometric relationships of all of the above parameters Alarms can include but are not limited to:

High/Low minute ventilation as percentage of predicted MV

High/Low tidal volume

High/Low respiratory rate

Apnea

High/Low EtCO2

SpO2 desaturation, hemoglobin level

High/Low oxygen extraction

Respiratory depression and its progression

High/Low heart rate

High/Low cardiac output

High/Low cardiac index

Cardiac preload, afterload and contractility

High/Low blood pressure

Heart failure and its progression

Arrhythmia

Sudden cardiac arrest

Hypertension (systemic and/or pulmonary)

Changes in metabolism

In another embodiment the machine learning and a-priori knowledge is preferably learned from a database by considering both number of events per hour per patient and per population. The system will preferably continue to adapt its learning based on the per hour event per patient.

Figure 46:
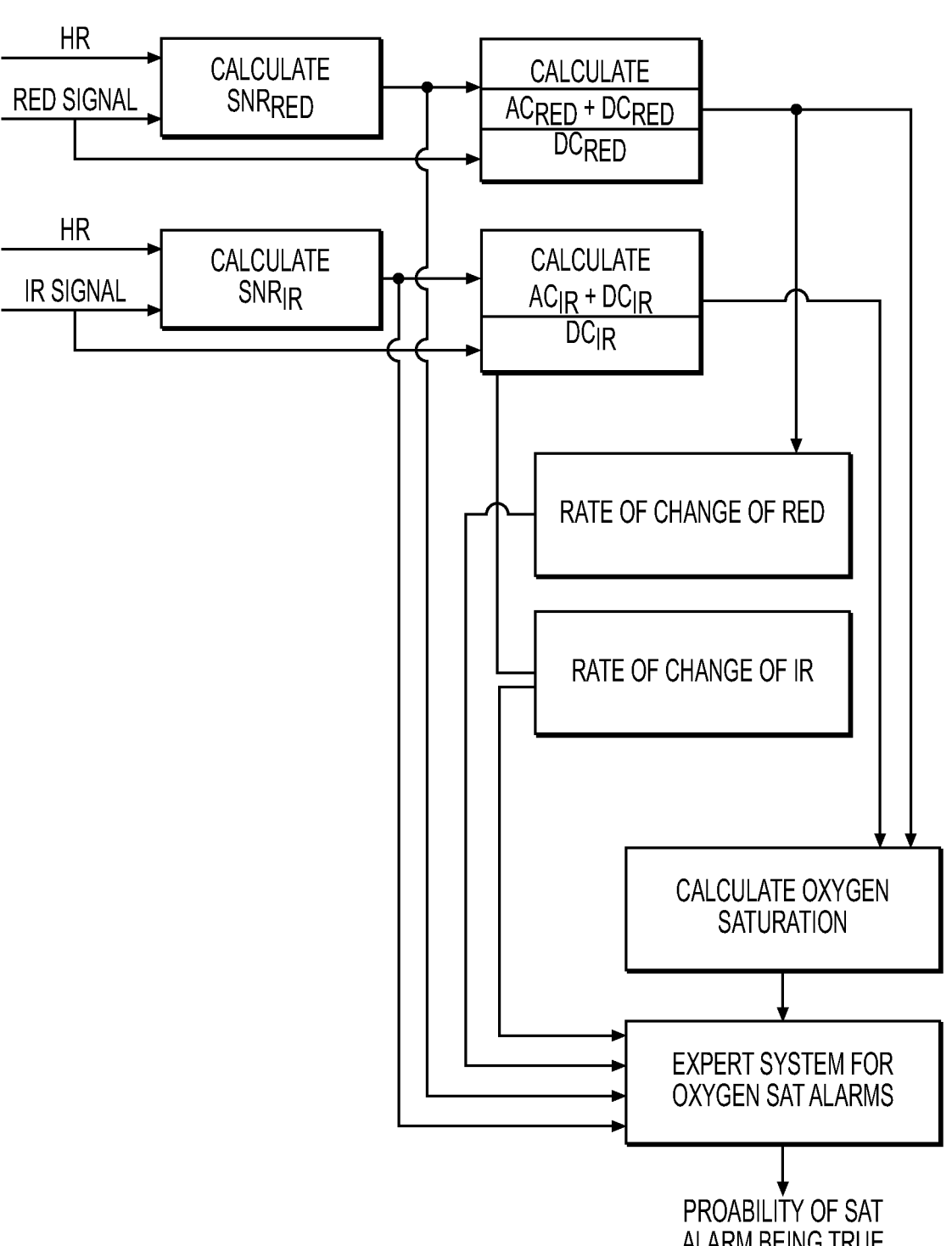
FIG. 46 depicts an example of a schematic of expert system as applied to true/false alarm qualification for SpO2 alarms.

Another embodiment is directed to, systems and/or methods that preferably evaluate components of certain physiological measurement "A" that may or may not consider other physiological measurements (B, C, etc) to validate measurement A. Time and frequency domain analysis of these parameters' signals can be used by the systems and methods to remove artifact and have more accurate measurements. For example, the oxy and deoxy hemoglobin signals are preferably analyzed separately instead of combined in an oxygen saturation (oxy/oxy+deoxy) measurement and may or may not use one or multiple of the inputs into the system as described in earlier embodiments to evaluate the validity of the oxygen saturation measurement. Evaluating the change of oxy and deoxy hemoglobin with respect to each other, the ratio of change and/or time frame in which the change occurs will preferably validate the "true" and "false" oxygen saturation and total hemoglobin measurements. FIG. 46 shows an illustration of a system and method that uses a subset of inputs using oxyhemoglobin, deoxyhemoglobin, and ECG to determine the validity of an oxygen saturation measurement and alarms.

Other embodiments and technical advantages of the invention are set forth herein and may be apparent from the drawings and the description of the invention, or may be learned from the practice of the invention. The various embodiments described herein can be combined. Furthermore, elements from one embodiment may be used in another embodiment.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A method of evaluating a patient after a medical event, comprising the steps of, on a patient monitoring device:

obtaining data for a plurality of patient parameters after the medical event, wherein the patient parameters include at least tidal volume (TV) and respiratory rate (RR) of the patient;

obtaining temporal data for each of the patient parameters after the medical event;

monitoring the temporal data for each patient parameter to identify a change of a state of the patient after the medical event;

evaluating the temporal data of the patient parameter corresponding to the change of the state of the patient and determining if the temporal data of the patient parameter is indicative of the change of the state of the patient being related to the medical event; and administering a treatment to the patient based on the change of the state of the patient, wherein the administered treatment is determined based on whether or not the change of the state of the patient is related to the medical event; and wherein the treatment is at least one of administering or adjusting a drug dosage and adjusting a ventilator.

2. The method of claim 1, wherein the temporal data is used for diagnosing and/or stratifying the patient based on the state of the patient and alerting medical staff of a diagnosis and/or stratification.

3. The method of claim 2, wherein the temporal data is used to qualify or weigh the data used in making the determination of patient state or in making a determination of a diagnosis and/or a stratification determination based on at least one of the amount of time after the event or the length of time elapsed monitoring the patient.

4. The method of claim 2, wherein the diagnosing and/or stratifying of the patient is based on at least one of supervised and unsupervised learning techniques, machine learning, Bayesian inference networks, expert systems, principal component analysis, support vector machines, time series forecasting and analysis, fractal analysis, statistical techniques, heuristic algorithms, deep temporal continuous and discontinuous clustering that integrates dimensionality reduction and temporal clustering into a single end-to-end learning framework, maximum margin temporal clustering, fuzzy logic, and neural networks.

5. The method of claim 2, wherein the diagnosis and/or stratifications are compared to a database of historic diagnosis and/or stratifications.

6. The method of claim 5, wherein feedback from caregivers is updated in the database for future diagnosis and/or stratifications.

7. The method of claim 1, wherein an event is at least one of a surgery, medication administration, intubation, extubation, lab tests, medical procedures, and patient care action.

8. The method of claim 1, wherein the parameters are at least one of physiological parameters, demographics, location, clinical events, treatments, physical state, and lab test results.

9. The method of claim 1, wherein the patient parameters are obtained from sensors or inputs that measure Minute ventilation (MV) and/or % of predicted MV, Tidal volume (TV), Respiratory rate (RR), Ventilation flow-volume relationship, Peripheral blood oxygen saturation (SpO2), Mixed venous oxygen saturation (SvO2), End-tidal carbon dioxide (EtCO2), Sublingual and/or transcutaneous CO2, temperature, Cardiac Output (CO), Cardiac index, Perfusion, Blood pressure (BP), Heart Rate (HR), Electrocardiogram (ECG), Renal fluid volumes and rates, Pain level scores and locations, Medication information, Patient location, Present and prior patient diagnoses and stratification of risk based on different clinical evaluation techniques, Temporal and ratiometric relationships of parameter measurements with respect to patient locations, Variation and rate of variation thereof, or Temporal and ratiometric relationships thereof.

10. The method of claim 1, wherein the TV and RR are indicative of a patient's status.

11. A system of evaluating a patient after a medical event, comprising:

a processor adapted to obtain temporal data of the patient after the medical event;

a plurality of input devices in communication with the processor adapted to monitor a plurality of patient parameters, wherein the patient parameters include at least tidal volume (TV) and respiratory rate (RR) of the patient; and wherein the processor:

compiles the temporal data of each of the monitored patient parameters;

identifies a change of a state of the patient based on the compiled temporal data;

evaluates the compiled temporal data to determine if the change of the state of the patient is indicative of the change of the state of the patient being related to the medical event; and administers a treatment to the patient based on the change of the state of the patient, wherein the administered treatment is determined based on whether or not the change of the state of the patient is related to the medical event; and wherein the treatment is at least one of administering or adjusting a drug dosage and adjusting a ventilator.

12. The system of claim 11, wherein the temporal data is used for diagnosing and/or stratifying the patient based on the state of the patient and alerting medical staff of a diagnosis and/or stratification.

13. The system of claim 12, wherein the temporal data is used to qualify or weigh the data used in making the determination of patient state or in making a determination of a diagnosis and/or a stratification determination based on at least one of the amount of time after the event or the length of time elapsed monitoring the patient.

14. The system of claim 12, wherein the diagnosing and/or stratifying of the patient is based on at least one of supervised and unsupervised learning techniques, machine learning, Bayesian inference networks, expert systems, principal component analysis, support vector machines, time series forecasting and analysis, fractal analysis, statistical techniques, heuristic algorithms, deep temporal continuous and discontinuous clustering that integrates dimensionality reduction and temporal clustering into a single end-to-end learning framework, maximum margin temporal clustering, fuzzy logic, and neural networks.

15. The system of claim 12, wherein the diagnosis and/or stratifications are compared to a database of historic diagnosis and/or stratifications.

16. The system of claim 15, wherein feedback from caregivers is updated in the database for future diagnosis and/or stratifications.

17. The system of claim 11, wherein an event is at least one of a surgery, medication administration, intubation, extubation, lab tests, medical procedures, and patient care action.

18. The system of claim 11, wherein the parameters are at least one of physiological parameters, demographics, location, clinical events, treatments, physical state, and lab test results.

19. The system of claim 11, wherein the parameters are obtained from sensors or inputs that measure Minute ventilation (MV) and/or % of predicted MV, Tidal volume (TV), Respiratory rate (RR), Ventilation flow-volume relationship, Peripheral blood oxygen saturation (SpO2), Mixed venous oxygen saturation (SvO2), End-tidal carbon dioxide (EtCO2), Sublingual and/or transcutaneous CO2, temperature, Cardiac Output (CO), Cardiac index, Perfusion, Blood pressure (BP), Heart Rate (HR), Electrocardiogram (ECG), Renal fluid volumes and rates, Pain level scores and locations, Medication information, Patient location, Present and prior patient diagnoses and stratification of risk based on different clinical evaluation techniques, Temporal and ratiometric relationships of parameter measurements with respect to patient locations, Variation and rate of variation thereof, or Temporal and ratiometric relationships thereof.

20. The system of claim 11, wherein the TV and RR are indicative of a patient's status.

21. A method of evaluating a patient after a medical event, comprising the steps of, on a bioimpedance measuring device:

obtaining data for a plurality of patient parameters after the medical event, wherein the patient parameters include at least tidal volume (TV) and respiratory rate (RR) of the patient obtained from the bioimpedance measuring device;

obtaining temporal data for each of the patient parameters after the medical event;

monitoring the temporal data for each patient parameter to determine a change of a state of the patient;

evaluating the temporal data of the patient parameter corresponding to the change of the state of the patient and determining if the temporal data of the patient parameter is indicative of the change of the state of the patient being related to the medical event; and administering a treatment to the patient based on the change of the state of the patient, wherein the administered treatment is determined based on whether or not the change of the state of the patient is related to the medical event; and wherein the treatment is at least one of administering or adjusting a drug dosage and adjusting a ventilator.

22. The method of claim 21, wherein the temporal data is used for diagnosing and/or stratifying the patient based on the state of the patient and alerting medical staff of a diagnosis and/or stratification.

23. The method of claim 22, wherein the temporal data is used to weight the diagnosis and/or stratification determination based on at least one of the amount of time after the event or the length of time elapsed monitoring the patient.

24. The method of claim 22, wherein the diagnosing and/or stratifying of the patient is based on at least one of supervised and unsupervised learning techniques, machine learning, Bayesian inference networks, expert systems, principal component analysis, support vector machines, time series forecasting and analysis, fractal analysis, statistical techniques, heuristic algorithms, deep temporal continuous and discontinuous clustering that integrates dimensionality reduction and temporal clustering into a single end-to-end learning framework, maximum margin temporal clustering, fuzzy logic, and neural networks.

25. The method of claim 22, wherein the diagnosis and/or stratifications are compared to a database of historic diagnosis and/or stratifications.

26. The method of claim 25, wherein feedback from caregivers is updated in the database for future diagnosis and/or stratifications.

27. The method of claim 21, wherein an event is at least one of a surgery, medication administration, intubation, extubation, lab tests, medical procedures, and patient care action.

28. A system of evaluating a patient, comprising:

a bioimpediance measuring device adapted to monitor a plurality of patient parameters, wherein the patient parameters include at least tidal volume (TV) and respiratory rate (RR) of the patient; and a processor coupled to the bioimpedance measuring device and adapted to:

obtain temporal data of the patient for of each of the monitored patient parameters;

identify a change of a state of the patient based on the temporal data;

evaluate the temporal data to determine if the change of the state of the patient is indicative of the change of the state of the patient being related to the medical event; and administers a treatment to the patient based on the change of the state of the patient, wherein the administered treatment is determined based on whether or not the change of the state of the patient is related to the medical event; and wherein the treatment is at least one of administering or adjusting a drug dosage and adjusting a ventilator.

29. The system of claim 28, wherein the temporal data is used for diagnosing and/or stratifying the patient based on the state of the patient and alerting medical staff of a diagnosis and/or stratification.

30. The system of claim 29, wherein the temporal data is used to weight the diagnosis and/or stratification determination based on at least one of the amount of time after the event or the length of time elapsed monitoring the patient.

31. The system of claim 28, wherein an event is at least one of a surgery, medication administration, intubation, extubation, lab tests, medical procedures, and patient care action.

32. The system of claim 28, wherein the diagnosing and/or stratifying of the patient is based on at least one of supervised and unsupervised learning techniques, machine learning, Bayesian inference networks, expert systems, principal component analysis, support vector machines, time series forecasting and analysis, fractal analysis, statistical techniques, heuristic algorithms, deep temporal continuous and discontinuous clustering that integrates dimensionality reduction and temporal clustering into a single end-to-end learning framework, maximum margin temporal clustering, fuzzy logic, and neural networks.

33. The system of claim 28, wherein the diagnosis and/or stratifications are compared to a database of historic diagnosis and/or stratifications.

34. The system of claim 33, wherein feedback from caregivers is updated in the database for future diagnosis and/or stratifications.

\* \* \* \* \*